United States Patent
Brameld et al.

(10) Patent No.: US 10,538,517 B2
(45) Date of Patent: Jan. 21, 2020

(54) QUINOLONE DERIVATIVES AS FGFR INHIBITORS

(71) Applicant: Principia Biopharma, Inc., South San Francisco, CA (US)

(72) Inventors: Kenneth Albert Brameld, Menlo Park, CA (US); Erik Verner, Belmont, CA (US)

(73) Assignee: Principia Biopharma, Inc., South San Francisco, CA (US)

( * ) Notice: Subject to any disclaimer, the term of this patent is extended or adjusted under 35 U.S.C. 154(b) by 0 days.

(21) Appl. No.: 15/575,448

(22) PCT Filed: May 18, 2016

(86) PCT No.: PCT/US2016/033065
§ 371 (c)(1),
(2) Date: Nov. 20, 2017

(87) PCT Pub. No.: WO2016/191172
PCT Pub. Date: Dec. 1, 2016

(65) Prior Publication Data
US 2018/0155340 A1     Jun. 7, 2018

Related U.S. Application Data

(60) Provisional application No. 62/165,526, filed on May 22, 2015.

(51) Int. Cl.
| | | |
|---|---|---|
| C07D 471/04 | (2006.01) | |
| A61K 31/519 | (2006.01) | |
| C07D 519/00 | (2006.01) | |
| A61K 45/06 | (2006.01) | |
| A61P 19/08 | (2006.01) | |
| A61P 35/00 | (2006.01) | |

(52) U.S. Cl.
CPC .......... *C07D 471/04* (2013.01); *A61K 31/519* (2013.01); *A61K 45/06* (2013.01); *A61P 19/08* (2018.01); *A61P 35/00* (2018.01); *C07D 519/00* (2013.01)

(58) Field of Classification Search
None
See application file for complete search history.

(56) References Cited

U.S. PATENT DOCUMENTS

| | | | |
|---|---|---|---|
| 5,620,981 | A | 4/1997 | Blankley et al. |
| 2009/0036472 | A1 | 2/2009 | Palle et al. |

FOREIGN PATENT DOCUMENTS

| | | |
|---|---|---|
| WO | 2005105097 | 11/2005 |
| WO | 2008150260 | 12/2008 |
| WO | 2012158843 | 11/2012 |
| WO | 2014011900 | 1/2014 |
| WO | 2014182829 | 11/2014 |

OTHER PUBLICATIONS

Patent Cooperation Treaty, International Search Report for PCT/US2016/033065, dated Jul. 27, 2016, 6 pages dated Jul. 26, 2016.
Bradshaw et al. Prolonged and tunable reisdence time using reversible covalent kinase inhibitors, Nature Chemical Biology, 2015, 11(7): 525-531 May 25, 2015.
Hamby et al., Structure-activity relationships for a novel series of pyrido[2,3-d]pyrimidine tyrosine kinase inhibitors. J Med Chem 40, 2296-303 (1997).
Tan et al., Development of covalent inhibitors that can overcome resistance to first-generation FGFR kinase inhibitors. Proc Natl Acad Sci U S A 111, E4869-E4877 (2014).
Thompson et al., 3-(3,5-Dimethoxyphenyl)-1,6-naphthyridine-2,7-diamines and related 2-urea derivatives are potent and selective inhibitors of the FGF receptor-1 tyrosine kinase. J Med Chem 43, 4200-11 (2000).
Thompson et al., Synthesis and structure-activity relationships of soluble 7-substituted 3-(3,5-dimethoxyphenyl)-1,6-naphthyridin-2-amines and related ureas as dual inhibitors of the fibroblast growth J Med Chem 48, 4628-53 (2005).
Zhou et al., A structure-guided approach to creating covalent FGFR inhibitors. Chem Biol 17, 285-95 (2010).

*Primary Examiner* — Zinna Northington Davis
(74) *Attorney, Agent, or Firm* — Bryan Cave Leighton Paisner LLP

(57) ABSTRACT

Compounds that are Fibroblast Growth Factor Inhibitors (FGFR) and are therefore useful for the treatment of diseases treatable by inhibition of FGFR are disclosed. Also disclosed are pharmaceutical compositions containing such compounds and processes for preparing such compounds.

23 Claims, No Drawings

QUINOLONE DERIVATIVES AS FGFR INHIBITORS

This application is a national phase application based on international application number PCT/US2016/033065 filed on May 18, 2016 which claims the benefit of U.S. Provisional Application Ser. No. 62/165,526 filed on May 22, 2015, which is incorporated by reference herein in its entirety.

FIELD OF THE DISCLOSURE

The present disclosure provides certain compounds that are Fibroblast Growth Factor Receptor Inhibitors (FGFR) and are therefore useful for the treatment of diseases treatable by inhibition of FGFR. Also provided are pharmaceutical compositions containing such compounds and processes for preparing such compounds.

BACKGROUND

Fibroblast growth factors (FGFs) and their receptors (FGFRs) play important roles in physiological processes relating to tissue repair, hematopoiesis, bone growth, angiogenesis and other aspects of embryonic development. Alterations in the FGF signaling pathway have also emerged as important drivers in human disease. FGF signaling can be deregulated through multiple mechanisms, including gene amplification, activating mutations and translocations, overexpression, altered FGFR gene splicing, and autocrine or paracrine overproduction of the ligands of FGFR. Deregulated FGF signaling has been documented in human tumors, including breast (see Ray, M. E., et. al., 2004. Genomic and expression analysis of the 8p11-12 amplicon in human breast cancer cell lines. Cancer Res 64:40-47), multiple myeloma (see Keats, J. J., et. al., 2006. Ten years and counting: so what do we know about t(4;14)(p16;q32) multiple myeloma. Leuk Lymphoma 47:2289-2300), non-invasive bladder (see Billerey, C., et al. 2001. Frequent FGFR3 mutations in papillary non-invasive bladder (pTa) tumors. Am J Pathol 158:1955-1959), endometrial (see Pollock, P. M., et al. 2007. Frequent activating FGFR2 mutations in endometrial carcinomas parallel germline mutations associated with craniosynostosis and skeletal dysplasia syndromes. Oncogene 26:7158-7162), gastric (see Jang, J. H., et. al., 2001. Mutations in fibroblast growth factor receptor 2 and fibroblast growth factor receptor 3 genes associated with human gastric and colorectal cancers. Cancer Res 61:3541-3543), prostate cancers (see Sahadevan, K., D et. al., 2007. Selective over-expression of fibroblast growth factor receptors 1 and 4 in clinical prostate cancer. J Pathol 213:82-90), lung (see Hammerman P, et al. Genomic characterization and targeted therapeutics in squamous cell lung cancer [abstract]; Proceedings of the 14th World Conference on Lung Cancer; 2011 3-7 Jul.; Aurora (Colo.); and International Association for the Study of Lung Cancer; 2011), esophageal (see Hanada K, et al., Identification of fibroblast growth factor-5 as an overexpressed anti-gen in multiple human adenocarcinomas. Cancer Res 2001; 61: 5511-6), cholangiocarcinoma (see Arai, Y., et al. 2014. Fibroblast growth factor receptor 2 tyrosine kinase fusions define a unique molecular subtype of cholangiocarcinoma. Hepatology 59, 1427-1434 and Borad, M. J., et al. 2014). Integrated genomic characterization reveals novel, therapeutically relevant drug targets in FGFR and EGFR pathways in sporadic intrahepatic cholangiocarcinoma. PLoS genetics 10, e1004135), glioblastoma (see Rand V., et. al. Sequence survey of receptor tyrosine kinases reveals mutations in glioblastomas. Proc Natl Acad Sci USA 2005; 102: 14344-9 and Parker, et. al. 2014. Emergence of FGFR family gene fusions as therapeutic targets in a wide spectrum of solid tumours. The Journal of pathology 232, 4-15). FGFR1 translocations and FGFR1 fusions are frequently observed in 8p11 myeloproliferative syndromes (Jackson, C. C., Medeiros, L. J., and Miranda, R. N. (2010). 8p11 myeloproliferative syndrome: a review. Human pathology 41, 461-476). Activating mutations in FGFR3 have been shown to cause a number of dwarf syndromes (see Harada, D., et. al., 2009. FGFR3-related dwarfism and cell signaling. J Bone Miner Metab 27:9-15) including achondroplasia (see Bellus, G. A., et. al., 1995. Achondroplasia is defined by recurrent G380R mutations of FGFR3. Am J Hum Genet 56:368-373; Bellus, G. A., et. al., 1995. A recurrent mutation in the tyrosine kinase domain of fibroblast growth factor receptor 3 causes hypochondroplasia. Nat Genet 10:357-359; and Rousseau, F., et. al., 1994. Mutations in the gene encoding fibroblast growth factor receptor-3 in achondroplasia. Nature 371:252-254), Crouzon dermoskeletal syndromes (see Robin, N. H., et. al., 1993. FGFR-Related Craniosynostosis Syndromes), hyopochondroplasia (see Prinos, P., et. al., 1995. A common FGFR3 gene mutation in hypochondroplasia. Hum Mol Genet 4:2097-2101), Muenke syndrome (see Muenke, M., et al. 1997. A unique point mutation in the fibroblast growth factor receptor 3 gene (FGFR3) defines a new craniosynostosis syndrome. Am J Hum Genet 60:555-564), SADDAN (severe achondroplasia with developmental delay and acanthosis nigricans) (see Bellus, G. A., et al. 1999. Severe achondroplasia with developmental delay and acanthosis nigricans (SADDAN): phenotypic analysis of a new skeletal dysplasia caused by a Lys650Met mutation in fibroblast growth factor receptor 3. Am J Med Genet 85:53-65; Tavormina, P. L., et al. 1999. A novel skeletal dysplasia with developmental delay and acanthosis nigricans is caused by a Lys650Met mutation in the fibroblast growth factor receptor 3 gene. Am J Hum Genet 64:722-731), thanatophoric dysplasia (see d'Avis, P. Y., et. al., 1998. Constitutive activation of fibroblast growth factor receptor 3 by mutations responsible for the lethal skeletal dysplasia thanatophoric dysplasia type I. Cell Growth Differ 9:71-78; Kitoh, H., et al., 1998. Lys650Met substitution in the tyrosine kinase domain of the fibroblast growth factor receptor gene causes thanatophoric dysplasia Type I. Mutations in brief no. 199. Online. Hum Mutat 12:362-363; and Tavormina, P. L., et. al., 1995. Thanatophoric dysplasia (types I and II) caused by distinct mutations in fibroblast growth factor receptor 3. Nat Genet 9:321-328), platyspondylic lethal skeletal dysplasia (see Brodie, S. G., et. al., 1999. Platyspondylic lethal skeletal dysplasia, San Diego type, is caused by FGFR3 mutations. Am J Med Genet 84:476-480), and cervical cancer (see Cappellen, D., et. al., 1999. Frequent activating mutations of FGFR3 in human bladder and cervix carcinomas. Nat Genet 23:18-20). Activating mutations in FGFR4 have been identified in rhabdomyosarcoma (see Shukla, N., et. al., Oncogene mutation profiling of pediatric solid tumors reveals significant subsets of embryonal rhabdomyosarcoma and neuroblastoma with mutated genes in growth signaling pathways. Clin Cancer Res 18:748-757 and Marshall, A. D., et. al., PAX3-FOXO1 and FGFR4 in alveolar rhabdomyosarcoma. Mol Carcinog 51:807-815). For these reasons, FGFRs are attractive therapeutic target for the treatment of diseases.

SUMMARY

In a first aspect, provided is a compound of Formula (I):

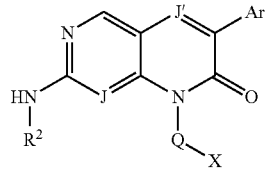

(I)

wherein:

J is N or CH;

J' is N or CR$^1$ where R$^1$ is hydrogen, halo, alkyl, or cycloalkyl;

Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;

R$^2$ is hydrogen, alkyl, alkynyl, acyl, alkoxycarbonyl, haloalkyl, cycloalkyl optionally substituted with amino, alkylamino, dialkylamino, or hydroxy, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, alkoxy, hydroxyalkyl, alkoxyalkyl, alkoxyalkyloxy, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, hydroxy, alkoxy, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl, phenyl ring in aralkyl, heteroaryl ring in heteroaralkyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, or optionally substituted heterocyclyl); and (i) Q is alkylene and X is —NR$^b$—Y—C(CN)=CHR$^c$; or (ii) Q is alkylene, substituted alkylene, heteroalkylene, substituted heteroalkylene, or alkylene-cycloalkylene-alkylene; and X is a group of formula (a), (b), (c), or (d):

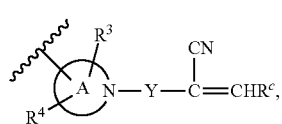

(a)

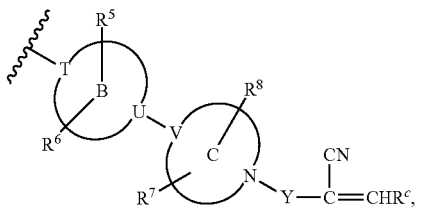

(b)

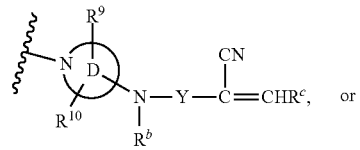

(c)

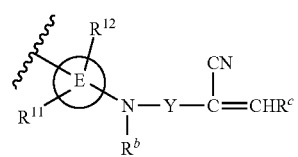

(d)

wherein:

T, U, and V, are independently N or CH provided that at least one of T and U is nitrogen;

ring A is heterocycloamino; bridged heterocycloamino, or spiroheterocycloamino;

rings B and C are independently azetidinyl, pyrrolidinyl, piperidinyl, homopiperidinyl, piperazinyl, or imidazolidine;

ring D is azetidinyl, pyrrolidinyl, piperidinyl, bridged heterocycloamino, or spiro heterocycloamino;

ring E is 5- or 6-membered cycloalkylene, phenylene, or 5- or 6-membered heteroarylene;

R$^3$, R$^4$, R$^5$, R$^6$, R$^7$, R$^8$, R$^9$, and R$^{10}$ are independently hydrogen, alkyl, hydroxy, alkoxy, or halo; and R$^{11}$ is hydrogen, alkyl, hydroxy, alkoxy, halo, haloalkyl, haloalkoxy, or cyano;

R$^{12}$ is hydrogen, alkyl, cycloalkyl, hydroxy, alkoxy, halo, haloalkyl, haloalkoxy, or cyano;

each Y is —CO— or —SO$_2$—;

each R$^b$ is hydrogen or alkyl; and each R$^c$ is alkyl, alkoxyalkyloxyalkyl, cycloalkyl optionally substituted with alkyl, 1-aminocycloalk-1-yl, substituted alkyl, heterocyclylalkyl, heterocyclyl (wherein the heterocyclyl in heterocyclylalkyl and heterocyclyl is optionally substituted with one, two, or three substituents where two of the optional substituents are independently selected from alkyl, alkoxy, hydroxy, halo, amino, and oxo, and one of the optional substituent is alkyl, hydroxyalkyl, alkoxyalkyl, acyl, haloalkyl, alkylsulfonyl, alkoxycarbonyl, or heterocyclyl wherein the heterocyclyl is optionally substituted with one or two substitutents independently selected from alkyl, halo, hydroxy, or alkoxy), heteroaralkyl (wherein the heteroaryl ring is optionally substituted with one or two substituents independently selected from alkyl, amino, alkylamino, or dialkylamino), bridged heterocycloaminoalkyl or spiroheterocycloaminoalkyl (wherein each of the aforementioned ring is optionally substituted with one or two alkyl and further wherein the alkylene chain in bridged heterocycloaminoalkyl or spiroheterocycloaminoalkyl is attached to the nitrogen atom of the bridged heterocycloamino and spiroheterocycloamino group), or -(alkylene)-NR$^{13}$R$^{14}$ where R$^{13}$ and R$^{14}$ together with the nitrogen atom to which they are attached form

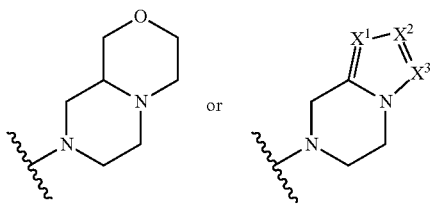

where one or two of X$^1$, X$^2$ and X$^3$ are nitrogen and the rest are carbon and the ring is optionally substituted with one or two substituents independently selected from alkyl, haloalkyl, and halo;
and/or a pharmaceutically acceptable salt thereof;
provided that: (1) when (i) ring E is 6-membered cycloalkylene, phenylene, or 6-membered heteroarylene or (ii) ring D is piperidinyl, then Q and —NR$^b$—Y—C(CN)=CHR$^c$ are meta or para to each other; (2) when ring A is piperidinyl, then Q and —Y—C(CN)=CR$^c$R$^d$ are meta or para to each other; (3) when ring A is piperazinyl, then Q and —Y—C(CN)=CHR$^c$ are para to each other; and (4) when rings A and D are pyrrolidinyl or azetidinyl, then Q and —NR$^b$—Y—C(CN)=CHR$^c$ or Q and —Y—C(CN)=CHR$^c$ are (1,3) to each other.

In one embodiment, the compounds of Formula (I) and/or a pharmaceutically acceptable salt thereof (and any embodiments thereof disclosed herein), the carbon atom attached to R$^1$ in —NR$^b$—Y—C(CN)=CHR$^c$ or —Y—C(CN)=CHR$^c$ group can form a reversible covalent bond with Cys488 of FGFR1, Cys491 of FGFR2, Cys482 of FGFR3, and/or Cys477 of FGFR4.

The reversibility of the covalent bond formed by a compound Formula (I) and/or a pharmaceutically acceptable salt thereof (and any embodiments thereof disclosed herein) with FGFR 1, 2, 3 and/or 4 can be determined by any of the methods described in Biological Examples 5, 6, or 7 below. In another embodiment, the formation of the covalent bond formed by a compound Formula (I) and/or a pharmaceutically acceptable salt thereof (and any embodiments thereof disclosed herein) with Cys488 of FGFR1, Cys491 of FGFR2, Cys482 of FGFR3, and/or Cys477 or Cys552 of FGFR4 is determined by cystallography.

In a second aspect, this disclosure is directed to a pharmaceutical composition comprising a compound, preferably a therapeutically effective amount of a compound, of the present disclosure, e.g., Formula (I) (or any of the embodiments thereof described herein), and/or a pharmaceutically acceptable salt thereof; and a pharmaceutically acceptable excipient.

In a third aspect, this disclosure is directed to a method of treating a disease treatable by inhibition of one or more FGFRs, in particular one or more of FGFR 1, 2, 3, and 4, in a patient in recognized need of such treatment which method comprises administering to the patient in recognized need thereof, a pharmaceutical composition comprising a compound, preferably a therapeutically effective amount of a compound, of the present disclosure, e.g., Formula (I) (or any of the embodiments thereof described herein) and/or a pharmaceutically acceptable salt thereof in a therapeutically effective amount, and a pharmaceutically acceptable excipient.

In one embodiment the disease is cancer such as breast cancer, multiple myeloma, bladder cancer, endometrial cancer, gastric cancer, cervical cancer, rhabdomyosarcoma, lung cancer including squamous cell lung cancer, lung adenocarcinoma, renal cell carcinoma, ovarian cancer, esophageal cancer, melanoma, colon cancer, hepatocellular carcinoma, head and neck squamous cell carcinoma, cholangiosarcoma, glioma, cholangiocarcinoma, 8,11 myeloproliferative syndrome, myeloproliferative disorders involving FGFR translocations/fusions, alveolar rhabdomyosarcoma, malignant rhabdoid tumors, and prostate cancers. In another embodiment, the disease includes dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia. In another embodiment, the cancer is glioblastoma, muscle invasive bladder or renal cancer.

In another embodiment, the compound of the present disclosure, e.g., Formula (I) (and any embodiments thereof described herein) and/or a pharmaceutically acceptable salt thereof is useful for the treatment of excessive FGF23 and hypophosphatemia as a consequence of autosomal dominant hypophosphatemic rickets (ADHR), autosomal recessive hypophosphatemic rickets (ARHR), X-linked hypophosphatemic rickets (XLH), tumor induced osteomalacia (TIO), renal transplantation, epidermal nevus syndrome, osteoglophonic dysplasia, and McCune-Albright syndrome.

In a fourth aspect, the disclosure is directed to a compound of the present disclosure, e.g., Formula (I) (or any embodiments thereof described herein) and/or a pharmaceutically acceptable salt thereof for use as a medicament. In one embodiment, the compound of the present disclosure, e.g., Formula (I) (and any embodiments thereof described herein) and/or a pharmaceutically acceptable salt thereof is useful for the treatment of cancer such as breast cancer, multiple myeloma, bladder cancer, endometrial cancer, gastric cancer, cervical cancer, rhabdomyosarcoma, lung cancer including squamous cell lung cancer, lung adenocarcinoma, renal cell carcinoma, ovarian cancer, esophageal cancer, melanoma, colon cancer, hepatocellular carcinoma, head and neck squamous cell carcinoma, cholioangiosarcoma, glioma, cholioangiocarcinoma, 8,11 myeloproliferative syndrome, myeloproliferative disorders involving FGFR translocations/fusions, alveolar rhabdomyosarcoma, malignant rhabdoid tumors, and prostate cancers.

In another embodiment, the compound of the present disclosure, e.g., Formula (I) (and any embodiments thereof described herein) and/or a pharmaceutically acceptable salt thereof is useful for the treatment of dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia. In another embodiment, the compound of the present disclosure, e.g., Formula (I) (and any embodiments thereof described herein) and/or a pharmaceutically acceptable salt thereof is useful for the treatment of excessive FGF23 and hypophosphatemia as a consequence of autosomal dominant hypophosphatemic rickets (ADHR), autosomal recessive hypophosphatemic rickets (ARHR), X-linked hypophosphatemic rickets (XLH), tumor induced osteomalacia (TIO), renal transplantation, epidermal nevus syndrome, osteoglophonic dysplasia, and McCune-Albright syndrome.

In a fifth aspect provided is the use of a compound of the present disclosure, e.g., Formula (I) and/or a pharmaceutically acceptable salt thereof (and any embodiments thereof disclosed herein) in the manufacture of a medicament for treating a disease in a patient in which the activity of FGFR contributes to the pathology and/or symptoms of the disease. In one embodiment the disease is cancer such as breast cancer, multiple myeloma, bladder cancer, endometrial cancer, gastric cancer, cervical cancer, rhabdomyosarcoma, lung cancer including squamous cell lung cancer, lung adenocarcinoma, renal cell carcinoma, ovarian cancer, esophageal cancer, melanoma, colon cancer, hepatocellular carcinoma, head and neck squamous cell carcinoma, cholioangiosarcoma, glioma, cholioangiocarcinoma, 8,11 myeloproliferative syndrome, myeloproliferative disorders involving FGFR translocations/fusions, alveolar rhabdomyosarcoma, malignant rhabdoid tumors, and prostate cancers.

In another embodiment the disease includes dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia. In another embodiment, the disease is hypophosphatemia as a consequence of autosomal dominant hypophosphatemic rickets (ADHR), autosomal recessive hypophosphatemic rickets (ARHR), X-linked hypophosphatemic rickets (XLH), tumor induced osteomalacia (TIO), renal transplantation, epidermal nevus syndrome, osteoglophonic dysplasia, and McCune-Albright syndrome.

In any of the aforementioned aspects involving the treatment of cancer, are further embodiments comprising administering the compound of the present disclosure, e.g., Formula (I) and/or a pharmaceutically acceptable salt thereof (or any embodiments thereof disclosed herein) in combination with at least one additional anticancer agent such as an EGFR inhibitor gefitinib, erlotinib, afatinib, icotinib, neratinib, rociletinib, cetuximab, panitumumab, zalutumumab, nimotuzumab, or matuzumab. In another embodiment, the compound of the present disclosure, e.g., Formula (I) (and any embodiments thereof described herein) and/or a pharmaceutically acceptable salt thereof is administered in combination with a HER2/neu inhibitor including lapatinib, trastuzumab, and pertuzumab. In another embodiment, the compound of the present disclosure, e.g., Formula (I) (and any embodiments thereof described herein) and/or a pharmaceutically acceptable salt thereof is administered in combination with a PI3k/mTOR inhibitor including idelalisib, buparlisib, BYL719, and LY3023414. When combination therapy is used, the agents can be administered simultaneously or sequentially.

In a sixth aspect, provided is a process of making a compound of Formula (I) as defined above, comprising:
(i) reacting a compound of formula (II):

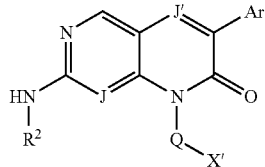

(II)

where J, J', Ar, $R^2$, and Q, are as defined for compound (I) above and and X' is

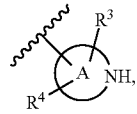

(a)

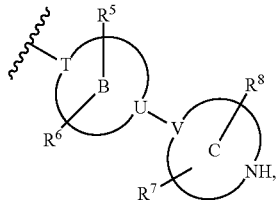

(b)

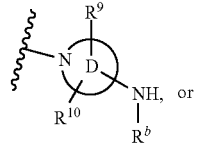

(c)

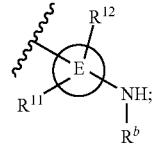

(d)

where $R^b$ as defined for Compound (I) above;

(a) with a compound of formula $R^cHC\!\!=\!\!C(CN)YLG$ where Y is —CO— or —SO$_2$—, $R^c$ is as defined in Formula (I) above, and LG is a leaving group under acylating reaction conditions, preferably halo such as fluoro or chloro; or (b) with a compound of formula $R^cHC\!\!=\!\!C(CN)COOH$ under amino acid reaction conditions; or (ii) reacting a compound of formula (III):

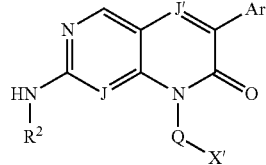

(II)

where J, J', Ar, $R^2$, and Q, are as defined for compound (I) above and X' is

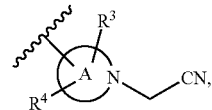

(a)

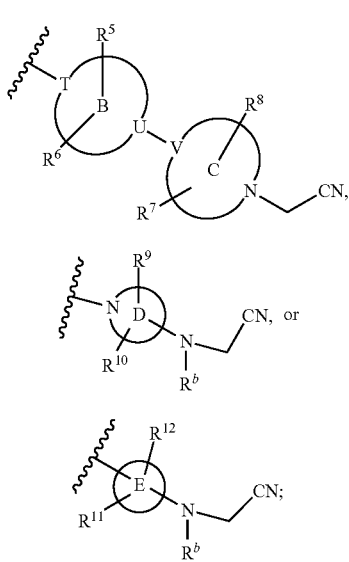

"1-aminocycloalk-1-yl" means

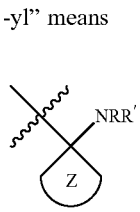

where R$^b$ as defined for Compound (I) above;

with a compound of formula R$^c$CHO where R$^c$ is as defined above;

(iii) optionally converting the compound of Formula (I) obtained from step (i) or (ii) to an acid addition salt; or (iv) optionally converting the compound of Formula (I) obtained from step (i) or (ii) to the free base.

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkynyl" means a linear monovalent hydrocarbon radical of two to six carbon atoms or a branched monovalent hydrocarbon radical of three to six carbon atoms containing a triple bond, e.g., propynyl, butynyl, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen or alkyl as defined above, e.g., aminomethyl, aminoethyl, methylaminomethyl, and the like.

where Z is cycloalkyl as defined above and R and R' are independently hydrogen or alkyl as defined above.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxyalkyloxyalkyl" means a -alkylene-(O)R radical where R is alkoxyalkyl as defined above, e.g., methoxyethoxymethyl, ethoxyethoxyethyl, and the like.

"Alkoxyalkyloxy" means a —(O)R radical where R is alkoxyalkyl as defined above, e.g., methoxyethoxy, ethoxyethoxy, and the like.

"Alkoxycarbonyl" means a —C(O)OR radical where R is alkyl as defined above, e.g., methoxycarbonyl, ethoxycarbonyl, and the like.

"Acyl" means a —C(O)R radical where R is alkyl as defined above, e.g., methylcarbonyl, ethylcarbonyl, and the like.

"Aralkyl" means a -(alkylene)-R radical where R is aryl as defined above, e.g., benzyl, phenethyl, and the like.

"Aryl" means a monovalent monocyclic or bicyclic aromatic hydrocarbon radical of 6 to 10 ring atoms e.g., phenyl or naphthyl.

"Bridged heterocycloamino" means a saturated bicyclic ring having 7 to 10 ring atoms with two or more atoms in common and in which one, two, or three ring atoms are heteroatom selected from N, O, or S(O)$_n$, where n is an integer from 0 to 2, the remaining ring atoms being C provided at least one ring atom are N and at least one ring atom is bonded to three or more ring atoms e.g., octahydropyrrolo[3,4-c]pyrrolyl, 2-azabicyclo[2.2.1]heptanyl, 7-azabicyclo[4.2.0]octane, octahydro-1H-pyrrolo[3,4-c]pyridine, or decahydro-2,6-naphthyridine, and the like.

"Bridged heterocycloaminoalkyl" means -(alkylene)-R where R is bridged heterocycloamino as defined above.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkylalkyl" means a -(alkylene)-R radical where R is cycloalkyl as defined above, e.g., cyclopropylmethyl, cyclohexylmethyl, and the like.

"Cycloalkylene" means a divalent cycloalkyl as defined above, unless stated otherwise.

"Carboxy" means —COOH.

"Dialkylamino" means a —NRR' radical where R and R' are alkyl as defined above, e.g., dimethylamino, methylethylamino, and the like.

"Halo" means fluoro, chloro, bromo, or iodo, preferably fluoro or chloro.

"Haloalkyl" means alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it can be referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or S(O)—, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylalkyl" or "heterocycloalkyl" means a -(alkylene)-R radical where R is heterocyclyl ring as defined above e.g., tetraydrofuranylmethyl, piperazinylmethyl, morpholinylethyl, and the like.

"Heterocycloamino" means a saturated or unsaturated monovalent monocyclic group of 4 to 8 ring atoms in which one or two ring atoms are heteroatom selected from N, O, or S(O)—, where n is an integer from 0 to 2, the remaining ring atoms being C provided that at least one of the ring atoms is N. Additionally, one or two ring carbon atoms in the heterocycloamino ring can optionally be replaced by a —CO— group. Unless otherwise stated, the heterocycloamino ring can optionally be substituted with one, two, or three substituents independently selected from alkyl, hydroxyl, alkoxy, amino, alkylamino, and dialkylamino.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroarylene" means a divalent heteroaryl radical.

"Heteroaralkyl" means a -(alkylene)-R radical where R is heteroaryl as defined above, e.g., pyridinylmethyl, and the like. When the heteroaryl ring in heteroaralkyl contains 5- or 6 ring atoms it is also referred to herein as 5- or 6-membered heteroaralkyl.

"Heteroalkylene" means alkylene as defined above wherein one, two, or three carbon atoms in the alkylene chain are independently replaced by a heteroatom selected from O, S, SO$_2$, and —NR— where R is hydrogen, alkyl, hydroxyalkyl, alkoxyalkyl, or alkoxyalkoxyalkyl, as defined above, e.g., —CH$_2$—CH$_2$—O—, —CH$_2$—CH$_2$—NH—, —CH$_2$—CH$_2$—N(CH$_3$)—, and the like.

The present disclosure also includes protected derivatives of compounds of the present disclosure (I). For example, when compounds of the present disclosure contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

The present disclosure also includes polymorphic forms and deuterated forms of the compound of the present disclosure and/or a pharmaceutically acceptable salt thereof.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diasteromeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity i.e., the (S) stereoisomer in less than about 5%, preferably 2% by wt and then it is denoted as a mixture of R and S isomers, the amounts of R or S isomer in the mixture is greater than about 5%, preferably 2% w/w.

Certain compounds of the present disclosure can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of the present disclosure are within the scope of this disclosure.

"Oxo" or "carbonyl" means =(O) group.

"Optionally substituted aryl" means aryl as defined above that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylthio, alkyl sulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylthio, alkyl sulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Phenylene" means a divalent phenyl group.

"Substituted alkyl" means alkyl group as defined herein which is substituted with one, two, or three substituents $R^a$, $R^b$, and $R^c$ independently selected from hydroxy, alkoxy, thiol, or —NRR$^1$ (where R is hydrogen, alkyl, cycloalkyl, hydroxyalkyl, alkoxyalkyl, or heterocyclyl optionally substituted with one or two groups independently selected from alkyl, hydroxyl, alkoxy, and halo and R' is hydrogen, alkyl, or cycloalkyl, each as defined herein.

"Substituted alkylene" means alkylene group as defined herein which is substituted with hydroxy, alkoxy, alkoxyalkyloxy, or —NRR' (where R is hydrogen, alkyl, hydroxyalkyl, alkoxyalkyl, and heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo.

"Substituted heteroalkylene" means heteroalkylene or group as defined herein which is substituted with hydroxy, alkoxy, alkoxyalkyloxy, or —NRR' (where R is hydrogen, alkyl, hydroxyalkyl, alkoxyalkyl, and heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo.

"Spiroheterocycloamino" means a saturated bicyclic ring having 6 to 10 ring atoms in which one, two, or three ring atoms are heteroatom selected from N, O, or S(O)—, where n is an integer from 0 to 2, the remaining ring atoms being C provided at least one ring atom is N and the rings are connected through only one atom, the connecting atom is also called the spiroatom, most often a quaternary carbon ("spiro carbon"). Representative examples include, but are not limited to, 2,6-diazaspiro[3.3]heptane, 2,6-diazaspiro[3.4]octane, 2-azaspiro[3.4]octane, 2-azaspiro[3.5]nonane, 2,7-diazaspiro[4.4]nonane, and the like.

"Spiroheterocycloaminoalkyl" means -(alkylene)-R where R is spiroheterocycloamino as defined above.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure and/or a pharmaceutically acceptable salt thereof that, when administered to a patient for treating a disease, is sufficient to effect such treatment for the disease. The "therapeutically effective amount" will vary depending on the compound, the disease and its severity and the age, weight, etc., of the mammal to be treated.

EMBODIMENTS

Embodiment A

In embodiment A, the compounds of Formula (I) and/or a pharmaceutically acceptable salt thereof as defined in the Summary above are those where J is CH.

Embodiment B

In embodiment B, the compounds of Formula (I) and/or a pharmaceutically acceptable salt thereof as defined in the Summary above are those where J is N.

Embodiment C

In embodiment C, the compounds of Formula (I) and/or a pharmaceutically acceptable salt thereof as defined in the Summary above are those where J' is N.

Embodiment D

In embodiment D, in one group of compounds, the compounds of Formula (I) and/or a pharmaceutically acceptable salt thereof as defined in the first aspect (i.e., in the Summary above) and in embodiments A and B are those where J' is —CR$^1$.

Within the groups of compounds in embodiment D, in one group of compounds and/or a pharmaceutically acceptable salt thereof R$^1$ is hydrogen. Within the groups of compounds in embodiment D, in another group of compounds and/or a pharmaceutically acceptable salt thereof R$^1$ is cyclopropyl. Within the groups of compounds in embodiment D, in yet another group of compounds and/or a pharmaceutically acceptable salt thereof where R$^1$ is methyl. Within the groups of compounds in embodiment D, in yet another group of compounds and/or a pharmaceutically acceptable salt thereof where R$^1$ is chloro or fluoro.

Embodiment E

In Embodiment E, the compounds of Formula (I) and/or a pharmaceutically acceptable salt thereof as defined in the first aspect in the Summary, in Embodiments A, B, C, and D above and groups contained therein, are those where Ar is phenyl optionally substituted with one, two, three, or four substituents independently selected from alkyl, hydroxy, alkoxy, halo, haloalkyl, haloalkoxy, and cyano.

(Ei) Within the groups of compounds in embodiment E and/or a pharmaceutically acceptable salt thereof, in one group of compounds and/or salts thereof, Ar is a phenyl ring optionally substituted with one, two, three, or four substituents independently selected from methyl, alkoxy, hydroxy, chloro, fluoro, trifluoromethyl, difluoromethyl, trifluoromethoxy, difluoromethoxy, and cyano.

(Eii) Within the groups of compounds in embodiment E and/or a pharmaceutically acceptable salt thereof, in another group of compounds and/or salts thereof, Ar is 3-methoxyphenyl, 2-halo-3-methoxyphenyl, 2-halo-5-methoxyphenyl, 2-halo-3,5-dimethoxyphenyl, 2,6-dihalo-3,5-dimethoxyphenyl, 3,5-dimethoxyphenyl, 2-halophenyl, or 2,6-dihalophenyl. Within these groups of compounds, in one group of compounds and/or salts thereof, Ar is 2-halo-3,5-dimethoxyphenyl, 2,6-dihalo-3,5-dimethoxyphenyl, 3,5-dimethoxyphenyl, or 2-halophenyl. Preferably, Ar is 2-halo-3,5-dimethoxyphenyl or 2,6-dihalo-3,5-dimethoxyphenyl.

Within the groups of compounds contained in embodiment E and/or a pharmaceutically acceptable salt thereof and groups contained therein i.e., (Ei)-(Eii) above, where Ar is a phenyl substituted with a halo group (e.g., 2-halo-3,5-dimethoxyphenyl or 2,6-di halo-3,5-dimethoxy-phenyl), in one group of compounds, halo is fluoro or chloro, preferably chloro.

Embodiment F

In Embodiment F, the compounds of Formula (I) and/or a pharmaceutically acceptable salt thereof as defined in the first aspect and/or the groups of compounds in Embodiments A, B, C, and D above and groups contained therein and/or a pharmaceutically acceptable salt thereof, are those wherein Ar is heteroaryl (such as pyridinyl or thienyl) ring optionally substituted with one, two, or three substituents independently selected from alkyl, hydroxy, alkoxy, halo, haloalkyl, haloalkoxy, and cyano.

(Fi) Within the groups of compounds in embodiment F and/or a pharmaceutically acceptable salt thereof, in one group of compounds and/or a pharmaceutically acceptable salt thereof, Ar is heteroaryl (such as pyridinyl or thienyl) ring optionally substituted with one, two, or three substituents independently selected from methyl, alkoxy, hydroxy, chloro, fluoro, trifluoromethyl, difluoromethyl, trifluoromethoxy, difluoromethoxy, and cyano.

Embodiment G

In Embodiment G, the compounds of Formula (I) and/or a pharmaceutically acceptable salt thereof as defined in first aspect above, the groups of compounds in Embodiments A, B, C, D, E, and F and/or a pharmaceutically acceptable salt thereof, and groups of contained therein, are those wherein X is a group of formula (a) or (b) and Q is as defined in the Summary.

G(i) Within the groups of compounds contained in embodiment G and/or a pharmaceutically acceptable salt thereof, in one group of compounds and/or a pharmaceutically acceptable salt, X is a group of formula (a) wherein ring A is piperazinyl, piperidinyl, pyrrolidinyl, or azetidinyl or X is a group of formula (b).

G(ii) Within the groups of compounds contained in embodiment G and G(i) and/or a pharmaceutically acceptable salt thereof, in one group of compounds and/or a pharmaceutically acceptable salt are those where Q is alkylene.

(a) Within the groups in G(ii), in one group of compounds and/or pharmaceutically acceptable salt thereof, X is a group of formula (a) where,

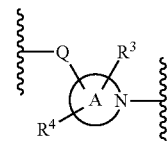

is:

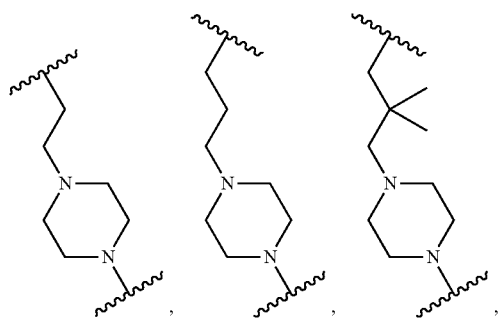

-continued

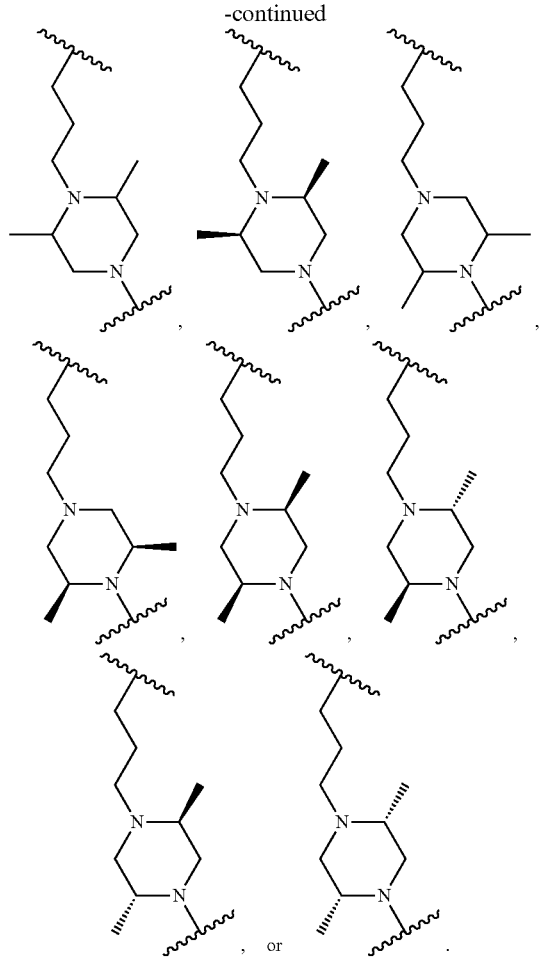

Preferably,

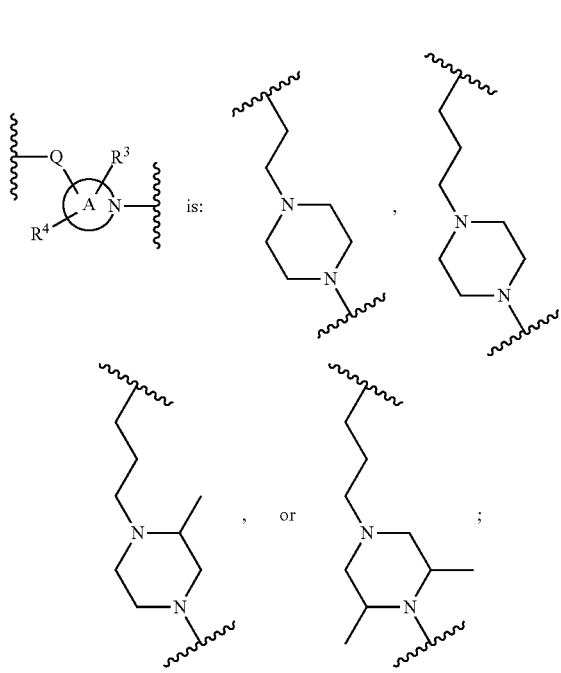

more preferably

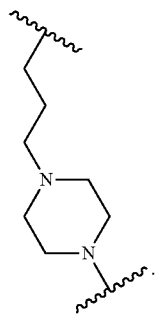

(b) Within the groups in G(ii), in another group of compounds and/or pharmaceutically acceptable salt thereof, X is a group of formula (a) where

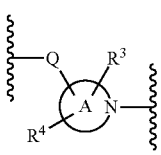

is:

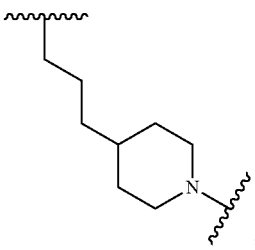

(Giii) Within the groups of compounds contained in embodiment G and G(i) and/or a pharmaceutically acceptable salt thereof, in yet another group of compounds and/or a pharmaceutically acceptable Q is heteroalkylene, preferably —(CH$_2$)$_2$O—, —(CH$_2$)$_2$S—, —(CH$_2$)$_2$NR where R is hydrogen alkyl, hydroxyalkyl, or alkoxyalkyl.

(a) Within the groups in (Giii), in one group of compounds, X is a group of formula (a) where,

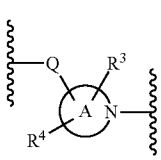

is:
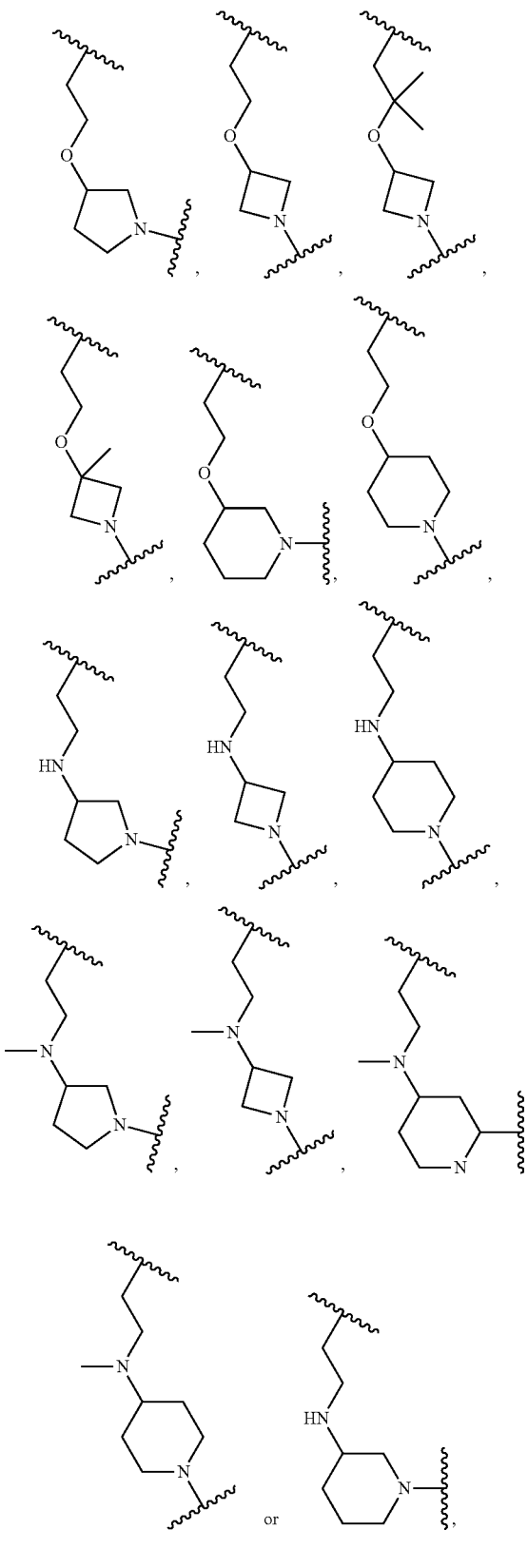
Preferably,
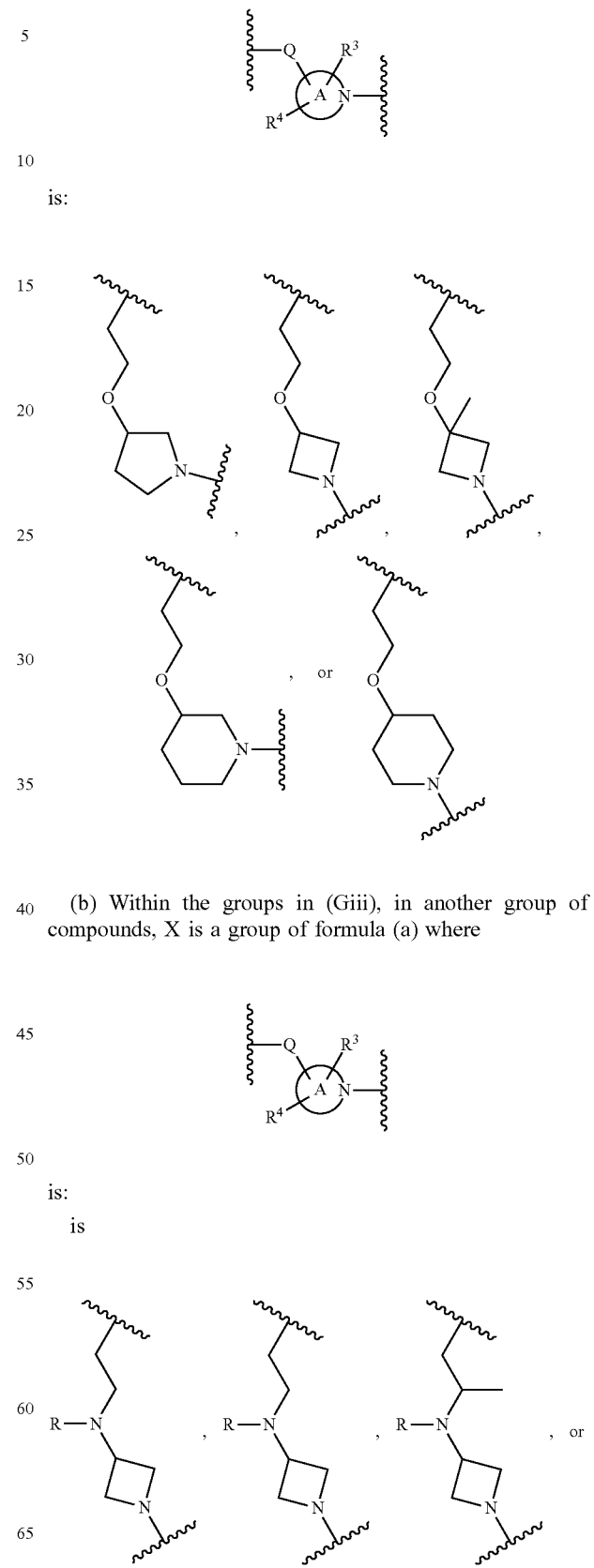
(b) Within the groups in (Giii), in another group of compounds, X is a group of formula (a) where
is:

-continued

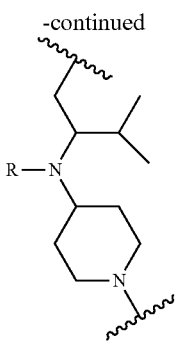

where R is methyl, ethyl, isopropyl, 2-hydroxyethyl, or 2-alkoxyethyl.

(Giv) Within the groups of compounds contained in embodiment G and (Gi) and/or a pharmaceutically acceptable salt thereof, in yet another group of compounds and/or a pharmaceutically acceptable salt, X is a group of formula (b). Preferably

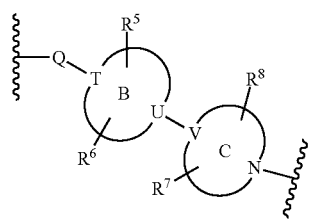

is:

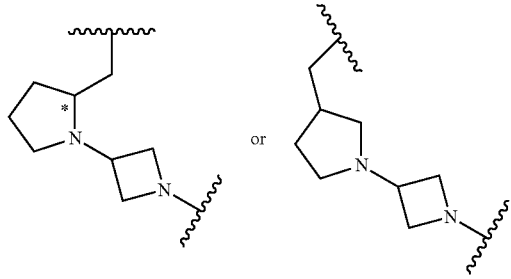

where stereochemistry at *C is R, S or RS.

Embodiment H

In Embodiment H, the compounds of Formula (I) and/or a pharmaceutically acceptable salt thereof as defined in first aspect above, the groups of compounds in Embodiments A, B, C, D, E, and F, and/or a pharmaceutically acceptable salt thereof, and groups of contained therein, are those wherein X is a group of formula (c) or (d) and Q is as defined in the Summary.

(Hi) Within the groups of compounds in (H) and/or a pharmaceutically acceptable salt thereof and groups of compounds and/or a pharmaceutically acceptable salt thereof contained therein, in one group of compounds and/or a pharmaceutically acceptable salt thereof, X is a group of formula (c).

(a) Within the groups of compounds in (Hi) and/or a pharmaceutically acceptable salt thereof, in one group of compounds and/or a pharmaceutically acceptable salt thereof, ring D is piperidin-1-yl, pyrrolidinyl, or azetidin-1-yl. Within the groups of compounds in (Hi) and/or a pharmaceutically acceptable salt thereof, in another group of compounds and/or salts thereof,

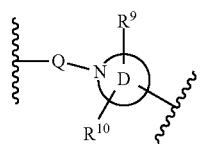

is:

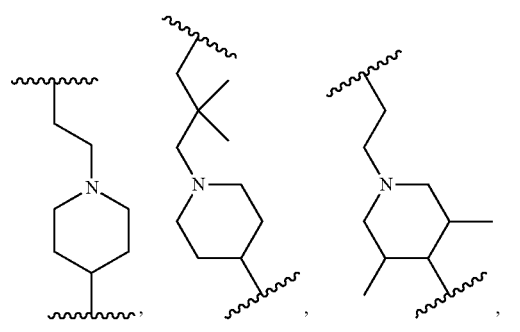

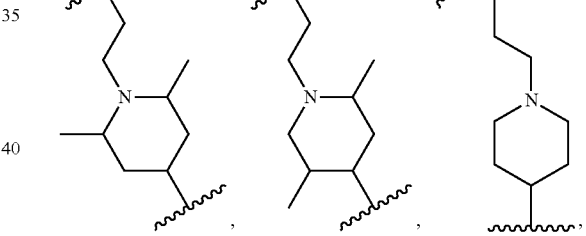

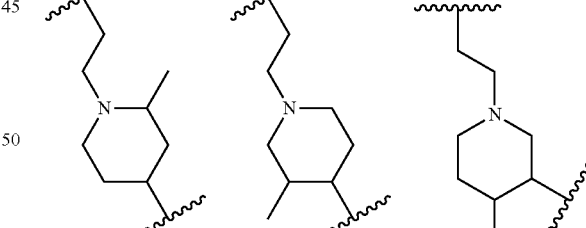

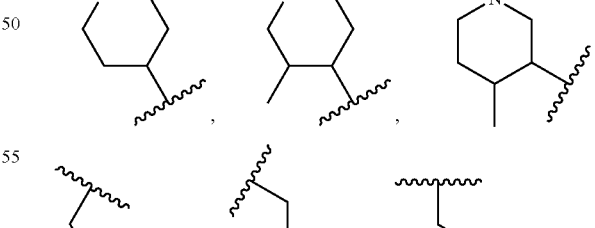

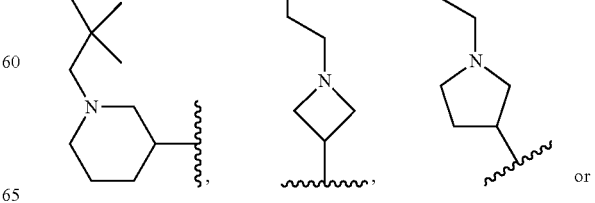

or

-continued

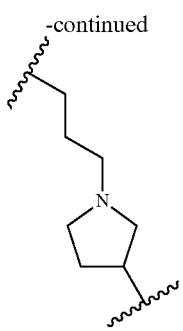

Preferably,

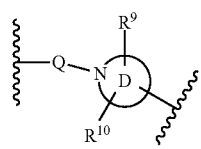

is:

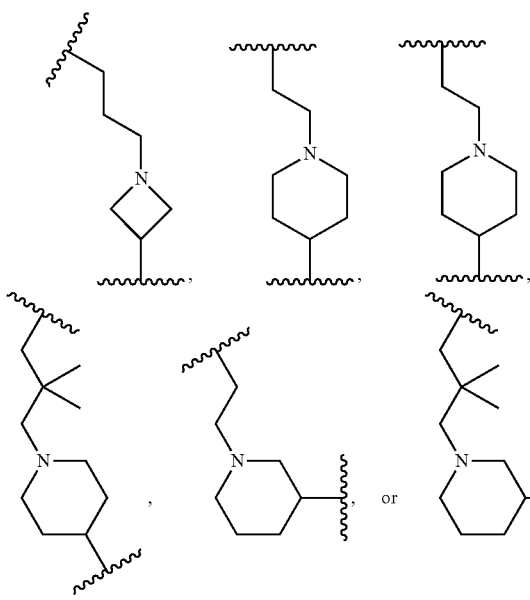

Within the groups of compounds in (Hi) and/or a pharmaceutically acceptable salt thereof and groups contained therein, in one group of compounds and/or a pharmaceutically acceptable salt thereof $R^b$ is hydrogen.

(b) Within the groups of compounds in (Hi) and/or a pharmaceutically acceptable salt thereof and groups of compounds and/or a pharmaceutically acceptable salt thereof contained therein, in yet another one group of compounds and/or a pharmaceutically acceptable salt thereof, X is a ring of formula (c) where ring D is bridged heterocycloamino.

(c) Within the groups of compounds in (Hi) and/or a pharmaceutically acceptable salt thereof and groups of compounds and/or a pharmaceutically acceptable salt thereof contained therein, in one group of compounds and/or a pharmaceutically acceptable salt thereof X is a ring of formula (c) where ring D is spiro heterocycloamino.

(Hii) Within the groups of compounds in (H) and/or a pharmaceutically acceptable salt thereof and groups of compounds and/or a pharmaceutically acceptable salt thereof contained therein, in one group of compounds and/or a pharmaceutically acceptable salt thereof, X is a group of formula (d). Within the groups of compounds in (Hii) and/or a pharmaceutically acceptable salt thereof, in one group of compounds and/or a pharmaceutically acceptable salt thereof, ring E is arylene or 5- or 6-membered heteroarylene.

(a) Within the groups of compounds in (Hii) and/or a pharmaceutically acceptable salt thereof, in one group of compounds and/or a pharmaceutically acceptable salt thereof, ring E is phenylene. Within groups of compounds in (Hii) and/or a pharmaceutically acceptable salt thereof, in yet another group of compounds and/or a pharmaceutically acceptable salt thereof, ring E is 5- or 6-membered heteroarylene ring. Within groups of compounds in (Hii) and/or a pharmaceutically acceptable salt thereof, in yet another group of compounds and/or a pharmaceutically acceptable salt thereof, ring E is pyridinyl, pyrimidinyl, pyridazinyl, thiazolyl, thienyl, oxazolyl, or imidazolyl. Within groups of compounds in (Hii) and/or a pharmaceutically acceptable salt thereof, in yet another group of compounds and/or a pharmaceutically acceptable salt thereof,

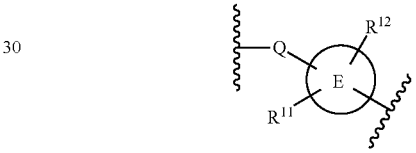

is:

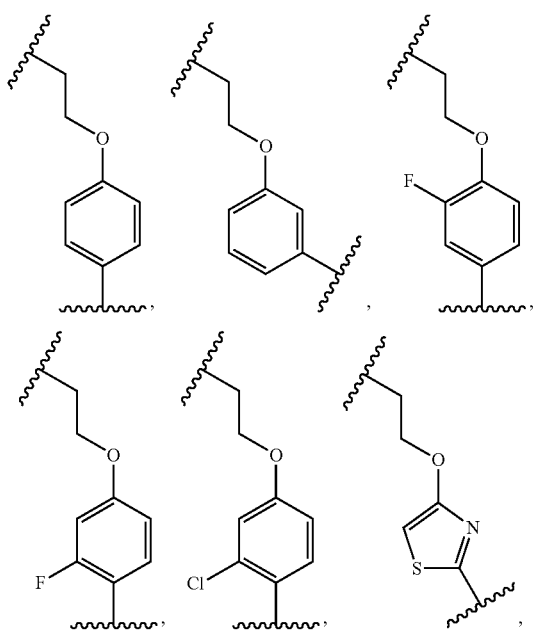

-continued

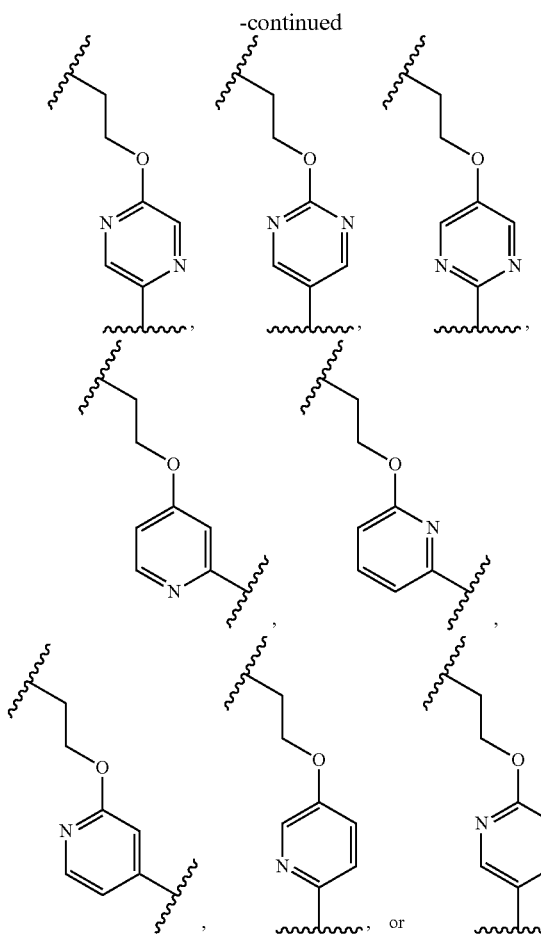

Preferably,

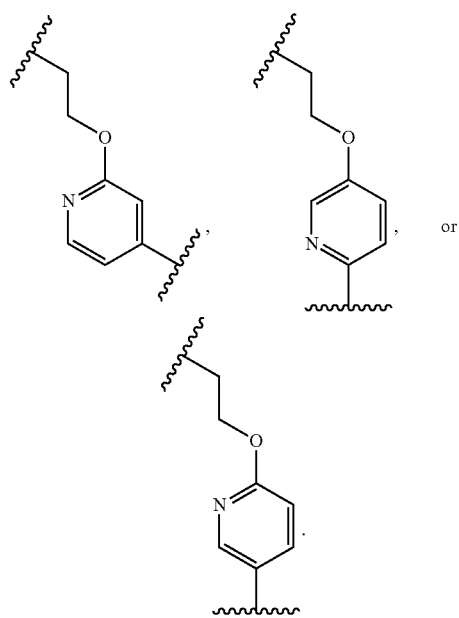

Within the groups of compounds in (Hii), subgroup (a), and/or a pharmaceutically acceptable salt thereof and groups of compounds or a pharmaceutically acceptable salt thereof contained therein, in one group of compounds and/or a pharmaceutically acceptable salt thereof, $R^b$ is hydrogen.

Embodiment I

In Embodiment I, the compounds of Formula (I) and/or a pharmaceutically acceptable salt thereof as defined in first aspect above, the groups of compounds in Embodiments A, B, C, D, E, and F, and/or a pharmaceutically acceptable salt thereof, and groups of contained therein, are those wherein wherein Q is -alkylene-cycloalkylene-alkylene-. Within these groups of compounds and/or a pharmaceutically acceptable salt thereof, in one group of compounds and/or salts thereof, Q is —(CH$_2$)-cyclopropylene-(CH$_2$)—.

Within the groups of compounds in (I) and/or a pharmaceutically acceptable salt thereof, in one group of compounds and/or a pharmaceutically acceptable salt thereof X is a group of formula (a), wherein

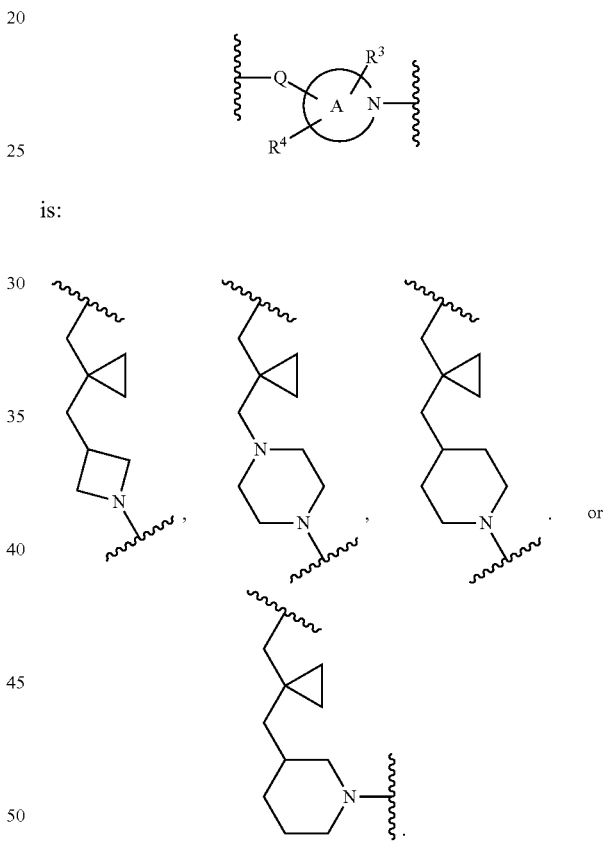

is:

Embodiment J

In embodiment J, the compounds of Formula (I) and/or a pharmaceutically acceptable salt thereof as defined in the first aspect above, the groups of compounds in embodiments A, B, C, D, E, F, G, H and/or I above and/or a pharmaceutically acceptable salt thereof, and groups of compounds and/or a pharmaceutically acceptable salt thereof contained therein are those wherein R$^2$ is hydrogen, alkyl, alkynyl, acyl, alkoxycarbonyl, haloalkyl, cycloalkyl optionally substituted with hydroxy, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where the phenyl ring in aralkyl, the heteroaryl ring in heteroaralkyl, phenyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl).

(Ji) Within the groups in embodiment J, in one group of compounds and/or salt thereof, $R^2$ is alkyl, alkynyl, acyl, alkoxycarbonyl, haloalkyl, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where the phenyl ring in aralkyl, the heteroaryl ring in heteroaralkyl, phenyl and heteroaryl are optionally substituted with one, two, or three substituents where two substituents are independently selected from alkyl, hydroxy, alkoxy, halo, haloalkyl, haloalkoxy, and cyano and the third substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl).

(Jii) Within the groups of compounds in J and/or a pharmaceutically acceptable salt thereof and group of compounds and/or salt thereof contained therein, in yet another group of compounds and/or a pharmaceutically acceptable salt thereof, $R^2$ is alkyl, preferably methyl, ethyl, isopropyl, or 2,2-dimethylpropyl.

(Jiii) Within the groups of compounds in J and/or a pharmaceutically acceptable salt thereof and group of compounds and/or salt thereof contained therein, in yet another group of compounds and/or a pharmaceutically acceptable salt thereof, $R^2$ is cycloalkylalkyl, preferably cyclopropylmethyl.

(Jiv) Within the groups of compounds in J and/or a pharmaceutically acceptable salt thereof and group of compounds and/or salt thereof contained therein, in yet another group of compounds and/or a pharmaceutically acceptable salt thereof, $R^2$ is hydroxyalkyl, preferably $R^2$ is 2-hydroxyethyl, 3-hydroxyprop-2-yl, 2,3-dihydroxypropyl, 2,2-dimethyl-3-hydroxypropyl, 2-hydroxy-2-methylpropyl, 2-methyl-3-hydroxyprop-2-yl, 3-hydroxy-2-hydroxymethylprop-2-yl, 1,3-dihydroxyprop-2-yl, or 1-hydroxy-2-hydroxymethylbut-2-yl.

(Jv) Within the groups of compounds in J and/or a pharmaceutically acceptable salt thereof and group of compounds and/or salt thereof contained therein, in yet another group of compounds and/or a pharmaceutically acceptable salt thereof, $R^2$ is alkoxyalkyl or alkoxyalkoxyalkyl, preferably $R^2$ is 2-isopropoxyethyl, 3-methoxyprop-2-yl, 2-ethoxyethyl, 1-3-dimethoxyprop-2-yl, 3-ethoxyprop-2-yl, 2-methoxyethyl, or 2-methoxyethoxyethyl.

(Jvi) Within the groups of compounds in J and/or a pharmaceutically acceptable salt thereof and group of compounds and/or salt thereof contained therein, in yet another group of compounds and/or a pharmaceutically acceptable salt thereof, $R^2$ is heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, aminoalkyl, optionally substituted aryl, optionally substituted heteroaryl, and optionally substituted heterocyclyl), preferably $R^2$ is 2-methyl-2-morpholin-4-ylpropyl, 2-(4-isopropylpiperazin-1-yl)ethyl, morpholin-4yl -ethyl, 2-(4-methylpiperazin-1-yl) ethyl, 3-morpholin-4-ylpropyl, 2,6-dimethylmorpholino-4-ethyl, 4,4-difluoropiperidin-1-ylethyl, tetrahydropyran-4-ylmethyl, 4-acetylpiperazin-1-ylethyl, 1,1-dimethyl-2-morpholin-4-ylethyl, 1,4-dimethylpiperidin-4-ylmethyl, 3-pyrrolidin-1-ylpropyl, (1-oxopyrrolidin-1-yl)ethyl, 3-(1-oxopyrrolidin-1-yl)propyl, (4-(2-hydroxy-2-methylpropyl) piperazin-1-ylethyl, 3-(4-methylpiperazin-1-yl)propyl, tetrahyrofuran-2-ylmethyl, 1-ethylpiperidin-4-ylmethyl, 2-(1, 1,-dioxothiomorpholin-4-yl)ethyl, 4-(oxetan-3-yl)piperazin-1-ylethyl, piperidin-1-ylethyl, 1-methylpiperidin-4-ylmethyl, 4-ethylpiperazin-1-ylethyl, pyrrolidin-1-ylethyl, 2,6-dimethylpiperazin-1-ylethyl, 3,5-dimethylpiperazin-1-ylethyl, 1-methyl-4-hydroxypiperidin-4-ylmethyl, or 3-(4-ethylpiperazin-1-yl)propyl.

(Jvii) Within the groups of compounds in J and/or a pharmaceutically acceptable salt thereof and group of compounds and/or salt thereof contained therein, in yet another group of compounds and/or a pharmaceutically acceptable salt thereof, $R^2$ is heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heteroaralkyl, phenyl, or heteroaryl where phenyl and heteroaryl are optionally substituted with one, two, or three substituents where two of the optional substituents are independently selected from alkyl, hydroxy, alkoxy, halo, haloalkyl, haloalkoxy, and cyano and the third optional substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl, preferably $R^2$ is pyridin-2-yl, imidazol-1-ylethyl, phenyl, oxetan-3-yl, 1-methylpiperidin-4-yl, 1-methylpiperazin-4-yl, tetrahydrofuran-3-yl or tetrahydropyran-4-yl.

(Jviii) Within the groups of compounds in H and/or a pharmaceutically acceptable salt thereof and group of compounds and/or salt thereof contained therein, in yet another group of compounds and/or a pharmaceutically acceptable salt thereof, $R^2$ is 2,2-difluoroethyl, 2,2,2-trifluoroethyl, propargyl, acetyl, or methoxycarbonyl.

(Jvix) Within the groups of compounds in J and/or a pharmaceutically acceptable salt thereof and group of compounds and/or salt thereof contained therein, in yet another group of compounds and/or a pharmaceutically acceptable salt thereof, $R^2$ is aminoalkyl, preferably $R^2$ is 3-dimethylaminopropyl, 4-diethylaminobutyl, 3-diethylaminopropyl, 2-diethylaminoethyl, or 2-dimethylaminoethyl.

(Jx) Within the groups of compounds in J and/or a pharmaceutically acceptable salt thereof and group of compounds and/or salt thereof contained therein, in yet another group of compounds and/or a pharmaceutically acceptable salt thereof, R² is:
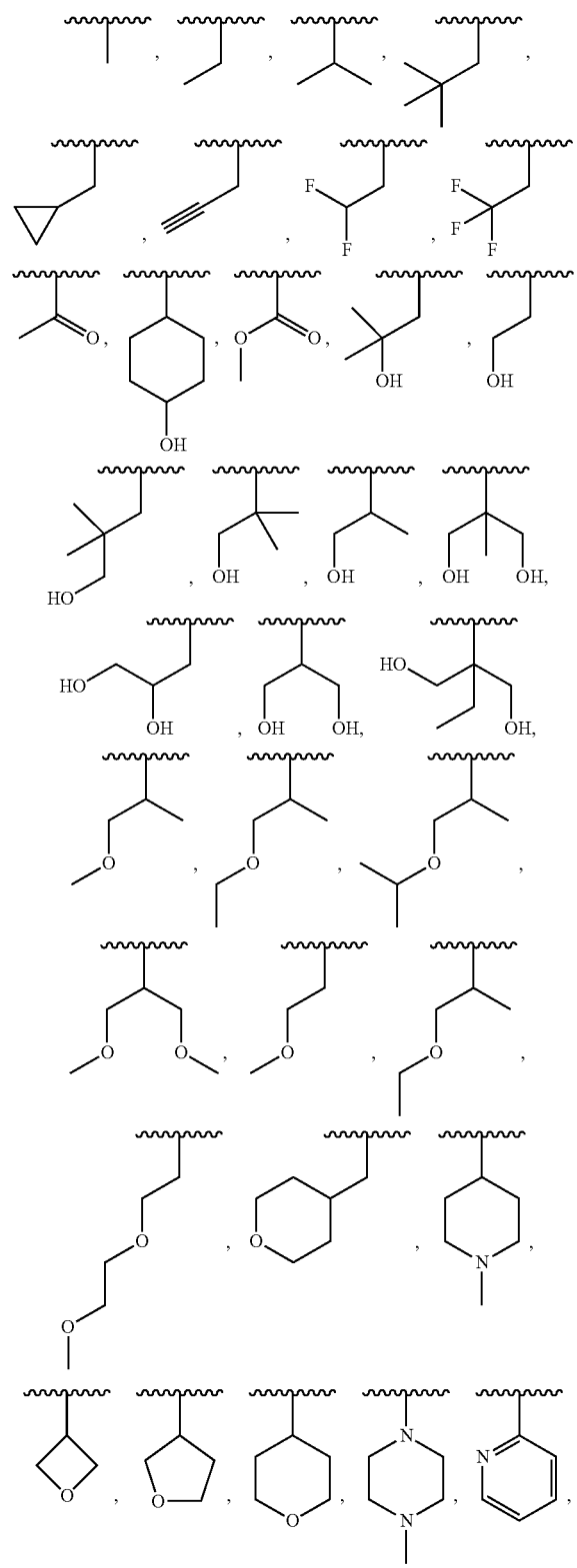
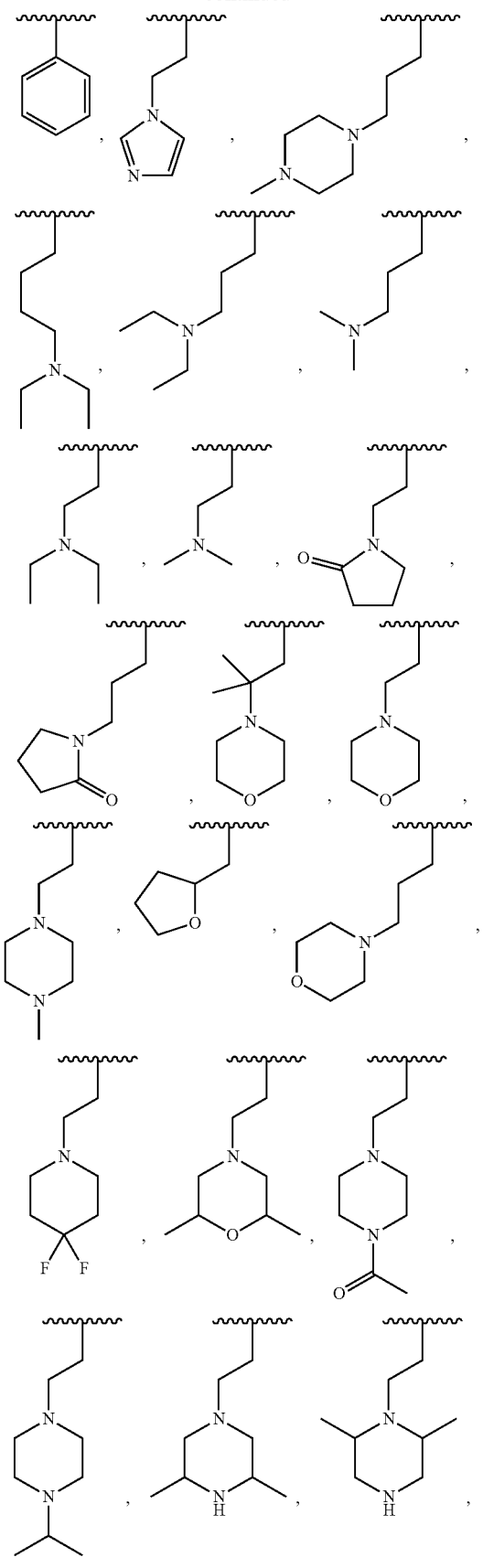

-continued

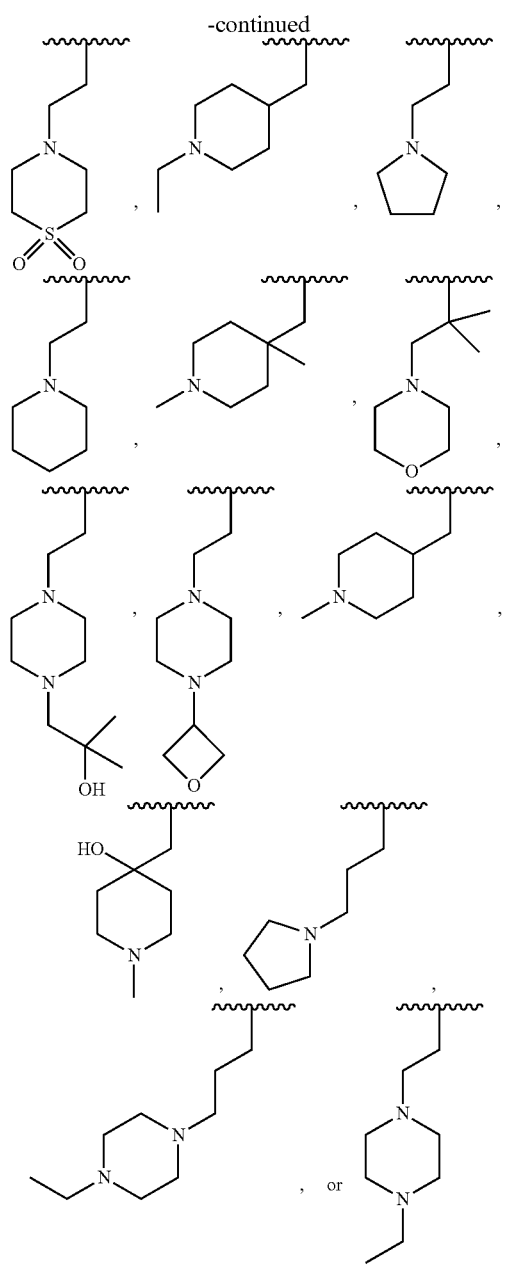

Embodiment K

In embodiment K, the compounds of Formula (I) and/or a pharmaceutically acceptable salt thereof as defined in the first aspect above, the groups of compounds in embodiments A, B, C, D, E, F, G, H, I, and/or J above and/or a pharmaceutically acceptable salt thereof, and groups of compounds and/or a pharmaceutically acceptable salt thereof contained within each of the groups therein are those wherein Y is —CO—.

Embodiment L

In embodiment L, the compounds of Formula (I) and/or a pharmaceutically acceptable salt thereof as defined in the first aspect above, the groups of compounds in embodiments A, B, C, D, E, F, G, H, I, J, and/or K above and/or a pharmaceutically acceptable salt thereof, and groups of compounds and/or a pharmaceutically acceptable salt thereof contained within each of the groups therein are those wherein $R^c$ is:

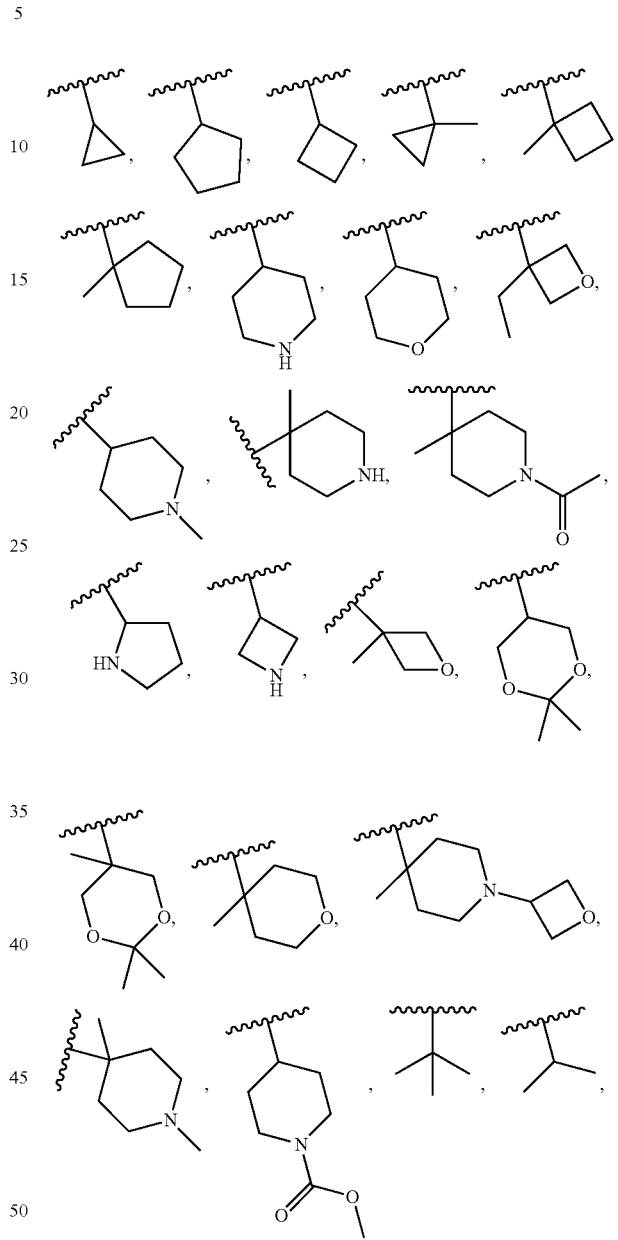

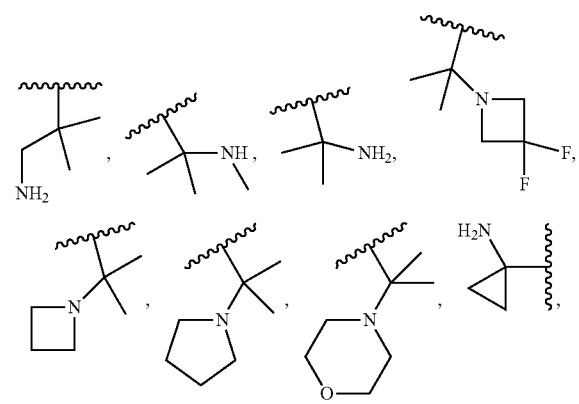

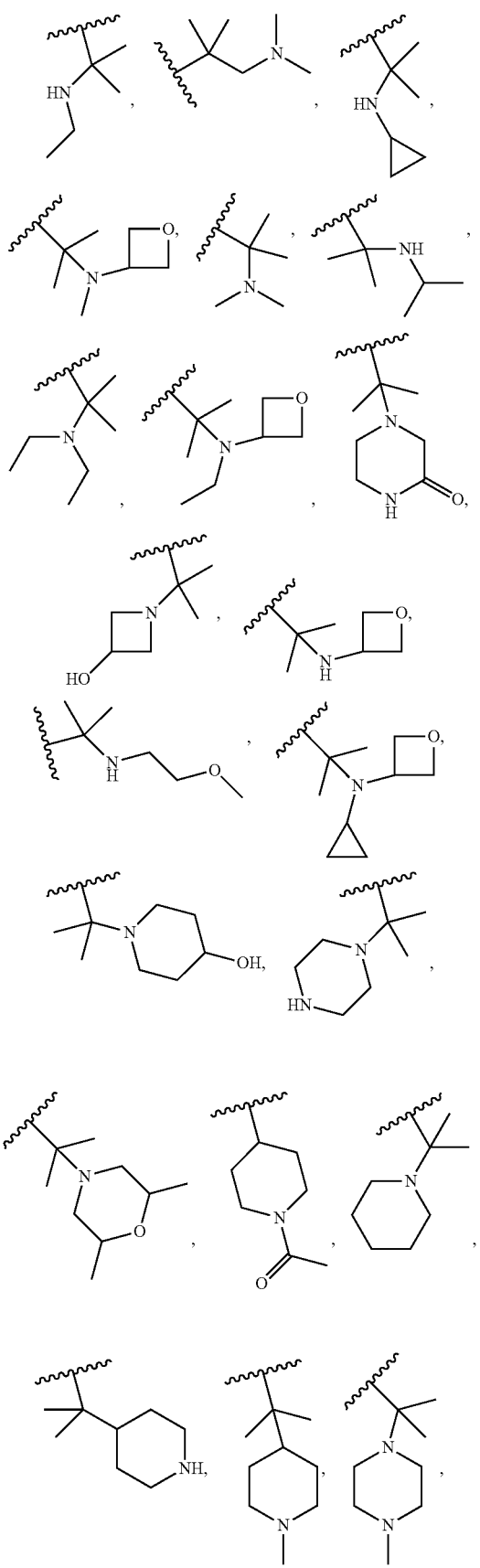
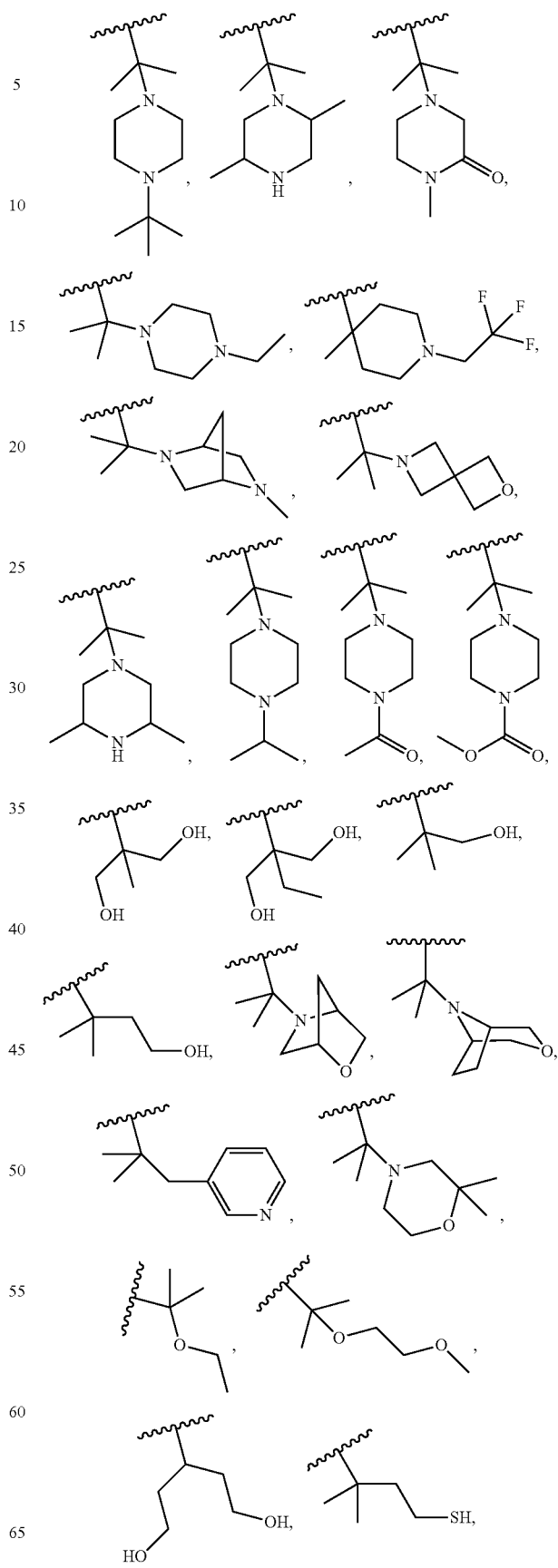

(Li) Within the groups of compounds in L and/or a pharmaceutically acceptable salt thereof and group of compounds and/or salt thereof contained therein, in one group of compounds and/or a pharmaceutically acceptable salt thereof, $R^c$ is alkyl, preferably isopropyl or tert-butyl.

(Lii) Within the groups of compounds in H and/or a pharmaceutically acceptable salt thereof and group of compounds and/or salt thereof contained therein, in another group of compounds and/or a pharmaceutically acceptable salt thereof, $R^2$ is cycloalkyl optionally substituted with alkyl, preferably cyclopropyl, cyclobutyl, cyclopentyl, 1-methylcyclopropylene, 1-methylcyclobutylene, or 1-methylcyclopentylene.

(Liii) Within the groups of compounds in H and/or a pharmaceutically acceptable salt thereof and group of compounds and/or salt thereof contained therein, in another group of compounds and/or a pharmaceutically acceptable salt thereof, $R^c$ is heterocyclyl optionally substituted as defined in the Summary. Preferably, $R^c$ is pyrrolidin-2-yl, 3-methyloxetan-3-yl,1-methoxycarbonylpiperidin-4-yl, 4-methylpiperidin-4-yl, 1-methycarbonyl-4-methylpiperidin-4-yl, 4-methyltetrahydropyran-4-yl, azetidin-3-yl, 1,4-dimethylpiperidin-4-yl, 1-methylpiperidin-4-yl, 4-methyl-1-(2,2,2-trifluoroethyl)piperidin-4-yl, 4-methyl-1-(2-methoxyethyl)piperidin-4-yl, 1-methylcarbonylpiperidin-4-yl, piperidin-4-yl, tetrahydropyran-4-yl, 1-methoxycarbonyl-4-methyl-piperidin-4-yl, 1-oxetan-3-yl-4-methylpiperidin-4-yl, or 3-ethyloxetan-3-yl.

(Liv) Within the groups of compounds in H and/or a pharmaceutically acceptable salt thereof and group of compounds and/or salt thereof contained therein, in another group of compounds and/or a pharmaceutically acceptable salt thereof, $R^c$ is heterocyclylalkyl optionally substituted as defined in the Summary. Preferably, $R^c$ is —C(CH$_3$)$_2$—R$^a$ where $R^a$ is pyrrolidin-1-yl, 4-methoxycarbonylpiperazin-1-yl, azetidin-1-yl, 1-methylpiperidin-4-yl, 4-(2-methoxyethyl)piperazin-1-yl, piperidin-4-yl, piperidin-1-yl, morpholino-4-yl, morpholino-4-ylmethyl, 2,2-dimethylmorpholin-4-yl, 3-hydroxyazetidin-1-yl, 4-hydroxypiperidin-1-yl, 3-oxopiperazin-1-yl, 4-methyl-3-oxopiperazin-1-yl, 4-ethyl-3-oxopiperazin-1-yl, 4-methyl-piperazin-1-yl, piperazin-1-yl, 3,5-dimethylpiperazin-1-yl, 2,6-dimethyl-morpholino-4-yl, 1,2,6-trimethylpiperazin-4-yl, 4-ethylpiperazin-1-yl, 4-isopropylpiperazin-1-yl, 4-tert-butylpiperazin-1-yl, 2,5-dimethylpiperazin-1-yl, 4-methylcarbonylpiperazin-1-yl, 1-oxetan-3-yl-piperazin-4-yl, or 3,3-difluoroazetidin-1-yl.

(Lv) Within the groups of compounds in H and/or a pharmaceutically acceptable salt thereof and group of compounds and/or salt thereof contained therein, in another group of compounds and/or a pharmaceutically acceptable salt thereof, $R^c$ is alkyl substituted with —NRR'. Preferably, $R^c$ is 2-methyl-3-amino-prop-2-yl, 2-methyl-3-dimethyl-amino-prop-2-yl, —C(CH$_3$)$_2$—NRR' where R is hydrogen, methyl, ethyl, or cyclopropyl and R' is hydrogen, methyl, ethyl, isopropyl, oxetan-3-yl, 2-ethoxyethyl, or cyclopropyl.

(Lvi) Within the groups of compounds in H and/or a pharmaceutically acceptable salt thereof and group of compounds and/or salt thereof contained therein, in another group of compounds and/or a pharmaceutically acceptable salt thereof, $R^c$ is alkyoxyalkyloxy or alkyl substituted with one to two hydroxy or alkoxy. Preferably, $R^c$ is 4-hydroxy-2-methylbut-2-yl, 1,5-dihydroxypent-3-yl, 2-ethoxyprop-2-yl, 1-hydroxy-2-hydroxymethylbut-2-yl, 1-hydroxy-2-hydroxymethylprop-2-yl, 2-hydroxymethylprop-2-yl, or 2-methoxyethyloxyprop-2-yl.

Representative compounds of the disclosure made are disclosed in Tables 1 and 2 below:

TABLE 1

| Compound No. | Names |
|---|---|
| 1 | 2-(3-(2-(6-(2-chlorophenyl)-2-((4-(diethylamino)butyl)amino)-7-oxopyrido[2,3-d]pyrimidin-8(7H)-yl)ethyl)piperidine-1-carbonyl)-4-methylpent-2-enenitrile |

TABLE 1-continued

| Compound No. | Names |
|---|---|
| 2 | 2-(4-(2-(6-(2-chloro-3,5-dimethoxyphenyl)-2-(methylamino)-7-oxopyrido[2,3-d]pyrimidin-8(7H)-yl)ethyl)piperazine-1-carbonyl)-4,4-dimethylpent-2-enenitrile |
| 3 | 2-(4-(2-(6-(2,6-dichloro-3,5-dimethoxyphenyl)-2-(methylamino)-7-oxopyrido[2,3-d]pyrimidin-8(7H)-yl)ethyl)piperazine-1-carbonyl)-4,4-dimethylpent-2-enenitrile |
| 4 | N-(1-(2-(6-(2-chloro-3,5-dimethoxyphenyl)-2-(methylamino)-7-oxopyrido[2,3-d]pyrimidin-8(7H)-yl)ethyl)piperidin-4-yl)-2-cyano-4,4-dimethylpent-2-enamide |
| 5 | 2-(4-(3-(6-(2-chloro-3,5-dimethoxyphenyl)-2-(methylamino)-7-oxopyrido[2,3-d]pyrimidin-8(7H)-yl)propyl)piperazine-1-carbonyl)-4,4-dimethylpent-2-enenitrile |
| 6 | 2-((3aR,6aS)-5-(2-(6-(2-chloro-3,5-dimethoxyphenyl)-2-(methylamino)-7-oxopyrido[2,3-d]pyrimidin-8(7H)-yl)ethyl)octahydropyrrolo[3,4-c]pyrrole-2-carbonyl)-4,4-dimethylpent-2-enenitrile |
| 7 | 2-(4-(3-(6-(2,6-dichloro-3,5-dimethoxyphenyl)-2-(methylamino)-7-oxopyrido[2,3-d]pyrimidin-8(7H)-yl)propyl)piperazine-1-carbonyl)-4,4-dimethylpent-2-enenitrile |
| 8 | 2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4,4-dimethylpent-2-enenitrile |
| 9 | 2-(3-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4,4-dimethylpent-2-enenitrile |
| 10 | 2-(3-(2-(6-(2,6-dichloro-3,5-dimethoxyphenyl)-2-(methylamino)-7-oxopyrido[2,3-d]pyrimidin-8(7H)-yl)ethoxy)pyrrolidine-1-carbonyl)-4,4-dimethylpent-2-enenitrile | or an individual (E) and (Z) isomers thereof;
or a pharmaceutically acceptable salt thereof of any of the above compounds including the individual (E) and (Z) isomers thereof.

TABLE 2

| Cpd. no | Name |
|---|---|
| 1 | N-(4-(2-(6-(2-chlorophenyl)-2-((4-(diethylamino)butyl)amino)-7-oxopyrido[2,3-d]pyrimidin-8(7H)-yl)ethyl)phenyl)-2-cyano-4-methylpent-2-enamide |
| 2 | 2-(3-(2-(6-(2-chlorophenyl)-2-((4-(diethylamino)butyl)amino)-7-oxopyrido[2,3-d]pyrimidin-8(7H)-yl)ethyl)piperidine-1-carbonyl)-4-methylpent-2-enenitrile |
| 3 | N-(3-(2-(6-(2-chlorophenyl)-2-((4-(diethylamino)butyl)amino)-7-oxopyrido[2,3-d]pyrimidin-8(7H)-yl)ethyl)phenyl)-2-cyano-4-methylpent-2-enamide |
| 4 | 2-cyano-N-(4-(2-(6-(2,6-dichloro-3,5-dimethoxyphenyl)-2-((4-(diethylamino)butyl)amino)-7-oxopyrido[2,3-d]pyrimidin-8(7H)-yl)ethyl)phenyl)-4-methylpent-2-enamide |
| 5 | 2-cyano-N-(3-((6-(2,6-dichloro-3,5-dimethoxyphenyl)-2-((4-(diethylamino)butyl)amino)-7-oxopyrido[2,3-d]pyrimidin-8(7H)-yl)methyl)phenyl)-4-methylpent-2-enamide |
| 6 | 2-cyano-N-(3-(2-(6-(2,6-dichloro-3,5-dimethoxyphenyl)-2-((4-(diethylamino)butyl)amino)-7-oxopyrido[2,3-d]pyrimidin-8(7H)-yl)ethyl)phenyl)-4-methylpent-2-enamide |
| 7 | 2-cyano-N-(3-(2-(6-(2,6-dichloro-3,5-dimethoxyphenyl)-2-(methylamino)-7-oxopyrido[2,3-d]pyrimidin-8(7H)-yl)ethyl)phenyl)-4-methylpent-2-enamide |
| 8 | 2-cyano-N-(4-(2-(6-(3,5-dimethoxyphenyl)-2-(methylamino)-7-oxopyrido[2,3-d]pyrimidin-8(7H)-yl)ethyl)phenyl)-4,4-dimethylpent-2-enamide |
| 9 | 4-amino-2-cyano-N-(4-(2-(6-(3,5-dimethoxyphenyl)-2-(methylamino)-7-oxopyrido[2,3-d]pyrimidin-8(7H)-yl)ethyl)phenyl)-4-methylpent-2-enamide |
| 10 | 2-cyano-N-(3-(2-(6-(3,5-dimethoxyphenyl)-2-(methylamino)-7-oxopyrido[2,3-d]pyrimidin-8(7H)-yl)ethyl)phenyl)-4,4-dimethylpent-2-enamide |
| 11 | 4-amino-2-cyano-N-(3-(2-(6-(3,5-dimethoxyphenyl)-2-(methylamino)-7-oxopyrido[2,3-d]pyrimidin-8(7H)-yl)ethyl)phenyl)-4-methylpent-2-enamide |
| 12 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4,4-dimethylpent-2-enamide |
| 13 | 4-amino-N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methylpent-2-enamide |
| 14 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4,4-dimethylpent-2-enamide |
| 15 | 4-amino-N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methylpent-2-enamide |
| 16 | N-(6-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4,4-dimethylpent-2-enamide |
| 17 | 4-amino-N-(6-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4-methylpent-2-enamide |
| 18 | 4-amino-2-cyano-N-(4-(2-(6-(3,5-dimethoxyphenyl)-2-(methylamino)-7-oxopyrido[2,3-d]pyrimidin-8(7H)-yl)pyridin-2-yl)-4-methylpent-2-enamide |
| 19 | 2-cyano-N-(6-(2-(6-(3,5-dimethoxyphenyl)-2-(methylamino)-7-oxopyrido[2,3-d]pyrimidin-8(7H)-yl)ethyl)pyridin-2-yl)-4,4-dimethylpent-2-enamide |
| 20 | 4-amino-N-(4-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4-methylpent-2-enamide |
| 21 | 4-amino-N-(5-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4-methylpent-2-enamide |

TABLE 2-continued

| Cpd. no | Name |
|---|---|
| 22 | 4-amino-2-cyano-N-(6-(2-(6-(3,5-dimethoxyphenyl)-2-(methylamino)-7-oxopyrido[2,3-d]pyrimidin-8(7H)-yl)ethyl)pyridin-2-yl)-4-methylpent-2-enamide |
| 23 | N-(4-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4,4-dimethylpent-2-enamide |
| 24 | 2-cyano-N-(4-(2-(6-(3,5-dimethoxyphenyl)-2-(methylamino)-7-oxopyrido[2,3-d]pyrimidin-8(7H)-yl)ethyl)pyridin-2-yl)-4,4-dimethylpent-2-enamide |
| 25 | 4-amino-2-cyano-N-(5-(2-(6-(3,5-dimethoxyphenyl)-2-(methylamino)-7-oxopyrido[2,3-d]pyrimidin-8(7H)-yl)ethyl)pyridin-2-yl)-4-methylpent-2-enamide |
| 26 | 4-amino-N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-N,4-dimethylpent-2-enamide |
| 27 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-ethoxy-4-methylpent-2-enamide |
| 28 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-morpholinopent-2-enamide |
| 29 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(methyl(oxetan-3-yl)amino)pent-2-enamide |
| 30 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(4-ethylpiperazin-1-yl)-4-methylpent-2-enamide |
| 31 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(2-oxa-6-azaspiro[3.3]heptan-6-yl)pent-2-enamide |
| 32 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(4-methylpiperazin-1-yl)pent-2-enamide |
| 33 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(methylamino)pent-2-enamide |
| 34 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(dimethylamino)-4-methylpent-2-enamide |
| 35 | 4-amino-N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-N,4-dimethylpent-2-enamide |
| 36 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-N,4-dimethyl-4-(methylamino)pent-2-enamide |
| 37 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(dimethylamino)-N,4-dimethylpent-2-enamide |
| 38 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-N,4-dimethyl-4-(methylamino)pent-2-enamide |
| 39 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(dimethylamino)-N,4-dimethylpent-2-enamide |
| 40 | 2-cyano-N-(5-(2-(6-(3,5-dimethoxyphenyl)-2-(methylamino)-7-oxopyrido[2,3-d]pyrimidin-8(7H)-yl)ethyl)pyridin-2-yl)-4,4-dimethylpent-2-enamide |
| 41 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-ethoxy-4-methylpent-2-enamide |
| 42 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-morpholinopent-2-enamide |
| 43 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(methyl(oxetan-3-yl)amino)pent-2-enamide |
| 44 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(2-oxa-6-azaspiro[3.3]heptan-6-yl)pent-2-enamide |
| 45 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(4-methylpiperazin-1-yl)pent-2-enamide |
| 46 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(4-ethylpiperazin-1-yl)-4-methylpent-2-enamide |
| 47 | N-(5-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4,4-dimethylpent-2-enamide |
| 48 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(methylamino)pent-2-enamide |
| 49 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(dimethylamino)-4-methylpent-2-enamide |
| 50 | N-(3-(2-(2-amino-6-(2-chloro-3,5-dimethoxyphenyl)-7-oxopyrido[2,3-d]pyrimidin-8(7H)-yl)ethyl)phenyl)-2-cyano-4,4-dimethylpent-2-enamide |
| 51 | N-(3-(2-(6-(2-chloro-3,5-dimethoxyphenyl)-2-(ethylamino)-7-oxopyrido[2,3-d]pyrimidin-8(7H)-yl)ethyl)phenyl)-2-cyano-4,4-dimethylpent-2-enamide |
| 52 | N-(3-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)phenyl)-2-cyano-4,4-dimethylpent-2-enamide |
| 53 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(4-hydroxypiperidin-1-yl)-4-methylpent-2-enamide |

TABLE 2-continued

| Cpd. no | Name |
|---|---|
| 54 | N-(3-((6-(2-chloro-3,5-dimethoxyphenyl)-2-(methylamino)-7-oxopyrido[2,3-d]pyrimidin-8(7H)-yl)methyl)phenyl)-2-cyano-4,4-dimethylpent-2-enamide |
| 55 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4,4-dimethylpentanamide |
| 56 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(4-hydroxypiperidin-1-yl)-4-methylpent-2-enamide |
| 57 | N-(3-(2-(6-(2-chloro-5-methoxyphenyl)-2-(methylamino)-7-oxopyrido[2,3-d]pyrimidin-8(7H)-yl)ethyl)phenyl)-2-cyano-4,4-dimethylpent-2-enamide |
| 58 | 2-cyano-N-(3-(2-(6-(2,4-dichlorophenyl)-2-(methylamino)-7-oxopyrido[2,3-d]pyrimidin-8(7H)-yl)ethyl)phenyl)-4,4-dimethylpent-2-enamide |
| 59 | 2-cyano-N-(3-(2-(6-(2,5-dimethylphenyl)-2-(methylamino)-7-oxopyrido[2,3-d]pyrimidin-8(7H)-yl)ethyl)phenyl)-4,4-dimethylpent-2-enamide |
| 60 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-((3S,5R)-3,4,5-trimethylpiperazin-1-yl)pent-2-enamide |
| 61 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(4-(oxetan-3-yl)piperazin-1-yl)pent-2-enamide |
| 62 | N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(4-(oxetan-3-yl)piperazin-1-yl)pent-2-enamide |
| 63 | N-(3-(2-(6-(5-chloro-2-methoxyphenyl)-2-(methylamino)-7-oxopyrido[2,3-d]pyrimidin-8(7H)-yl)ethyl)phenyl)-2-cyano-4,4-dimethylpent-2-enamide |
| 64 | 2-cyano-4,4-dimethyl-N-(3-(2-(2-(methylamino)-7-oxo-6-(o-tolyl)pyrido[2,3-d]pyrimidin-8(7H)-yl)ethyl)phenyl)pent-2-enamide |
| 65 | 2-cyano-N-(3-(2-(6-(2-fluoro-3-methoxyphenyl)-2-(methylamino)-7-oxopyrido[2,3-d]pyrimidin-8(7H)-yl)ethyl)phenyl)-4,4-dimethylpent-2-enamide |
| 66 | 2-cyano-N-(3-(2-(6-(2-fluoro-5-methoxyphenyl)-2-(methylamino)-7-oxopyrido[2,3-d]pyrimidin-8(7H)-yl)ethyl)phenyl)-4,4-dimethylpent-2-enamide |
| 67 | N-(4-(2-(6-(2-chloro-3,5-dimethoxyphenyl)-2-(methylamino)-7-oxopyrido[2,3-d]pyrimidin-8(7H)-yl)ethyl)thiazol-2-yl)-2-cyano-4,4-dimethylpent-2-enamide |
| 68 | N-(4-(2-(6-(2-chloro-3,5-dimethoxyphenyl)-2-((2-morpholinoethyl)amino)-7-oxopyrido[2,3-d]pyrimidin-8(7H)-yl)ethyl)phenyl)-2-cyano-4,4-dimethylpent-2-enamide |
| 69 | N-(6-(2-(6-(2-chloro-3,5-dimethoxyphenyl)-2-((2-morpholinoethyl)amino)-7-oxopyrido[2,3-d]pyrimidin-8(7H)-yl)ethyl)pyridin-3-yl)-2-cyano-4,4-dimethylpent-2-enamide |
| 70 | N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-3-methylbut-2-enamide |
| 71 | N-(5-(2-(6-(2-chloro-3,5-dimethoxyphenyl)-2-(methylamino)-7-oxopyrido[2,3-d]pyrimidin-8(7H)-yl)ethyl)pyrazin-2-yl)-2-cyano-4,4-dimethylpent-2-enamide |
| 72 | N-(tert-butyl)-3-(4-(2-(6-(2-chloro-3,5-dimethoxyphenyl)-2-(methylamino)-7-oxopyrido[2,3-d]pyrimidin-8(7H)-yl)ethyl)phenyl)-2-cyanoacrylamide |
| 73 | N-(tert-butyl)-3-(3-(2-(6-(2-chloro-3,5-dimethoxyphenyl)-2-(methylamino)-7-oxopyrido[2,3-d]pyrimidin-8(7H)-yl)ethyl)phenyl)-2-cyanoacrylamide |
| 74 | 2-cyano-N-(4-(2-(6-(2-fluoro-3,5-dimethoxyphenyl)-2-((2-morpholinoethyl)amino)-7-oxopyrido[2,3-d]pyrimidin-8(7H)-yl)ethyl)phenyl)-4,4-dimethylpent-2-enamide |
| 75 | N-(tert-butyl)-3-(4-(3-(6-(2-chloro-3,5-dimethoxyphenyl)-2-(methylamino)-7-oxopyrido[2,3-d]pyrimidin-8(7H)-yl)propyl)phenyl)-2-cyanoacrylamide |
| 76 | N-(tert-butyl)-3-(3-(3-(6-(2-chloro-3,5-dimethoxyphenyl)-2-(methylamino)-7-oxopyrido[2,3-d]pyrimidin-8(7H)-yl)propyl)phenyl)-2-cyanoacrylamide |
| 77 | N-(2-chloro-4-(2-(6-(2-chloro-3,5-dimethoxyphenyl)-2-((2-morpholinoethyl)amino)-7-oxopyrido[2,3-d]pyrimidin-8(7H)-yl)ethyl)phenyl)-2-cyano-4,4-dimethylpent-2-enamide |
| 78 | N-(4-(2-(6-(2-chloro-3,5-dimethoxyphenyl)-2-((2-morpholinoethyl)amino)-7-oxopyrido[2,3-d]pyrimidin-8(7H)-yl)ethyl)-3-fluorophenyl)-2-cyano-4,4-dimethylpent-2-enamide |
| 79 | N-(4-(2-(6-(2-chloro-3,5-dimethoxyphenyl)-2-((2-morpholinoethyl)amino)-7-oxopyrido[2,3-d]pyrimidin-8(7H)-yl)ethyl)-2-fluorophenyl)-2-cyano-4,4-dimethylpent-2-enamide | or an individual (E) and (Z) isomers thereof;
or a pharmaceutically acceptable salt thereof of any of the above compounds including the individual (E) and (Z) isomers thereof.

Other representative compounds of the invention are listed below:

2-(3-((2-(6-(2,6-dichloro-3,5-dimethoxyphenyl)-2-(methylamino)-7-oxopyrido[2,3-d]pyrimidin-8(7H)-yl)ethyl)amino)azetidine-1-carbonyl)-4,4-dimethylpent-2-enenitrile;

2-(3-((2-(6-(2,6-dichloro-3,5-dimethoxyphenyl)-2-(methylamino)-7-oxopyrido[2,3-d]pyrimidin-8(7H)-yl)ethyl)(methyl)amino)azetidine-1-carbonyl)-4,4-dimethylpent-2-enenitrile;

2-cyano-N-(1-(3-(6-(2,6-dichloro-3,5-dimethoxyphenyl)-2-(methylamino)-7-oxopyrido[2,3-d]pyrimidin-8(7H)-yl)propyl)piperidin-3-yl)-4,4-dimethylpent-2-enamide;

2-cyano-N-(1-(3-(6-(2,6-dichloro-3,5-dimethoxyphenyl)-2-(methylamino)-7-oxopyrido[2,3-d]pyrimidin-8(7H)-yl)propyl)pyrrolidin-3-yl)-4,4-dimethylpent-2-enamide;

2-(3-((2-(6-(2,6-dichloro-3,5-dimethoxyphenyl)-2-(methylamino)-7-oxopyrido[2,3-d]pyrimidin-8(7H)-yl)ethyl)(ethyl)amino)azetidine-1-carbonyl)-4,4-dimethylpent-2-enenitrile;

2-(4-((2-(6-(2,6-dichloro-3,5-dimethoxyphenyl)-2-(methylamino)-7-oxopyrido[2,3-d]pyrimidin-8(7H)-yl)ethyl)(methyl)amino)piperidine-1-carbonyl)-4,4-dimethylpent-2-enenitrile;

2-(4-((2-(6-(2,6-dichloro-3,5-dimethoxyphenyl)-2-(methylamino)-7-oxopyrido[2,3-d]pyrimidin-8(7H)-yl)ethyl)(ethyl)amino)piperidine-1-carbonyl)-4,4-dimethylpent-2-enenitrile;

2-(3-(2-((6-(2,6-dichloro-3,5-dimethoxyphenyl)-2-(methylamino)-7-oxopyrido[2,3-d]pyrimidin-8(7H)-yl)methyl)pyrrolidin-1-yl)azetidine-1-carbonyl)-4,4-dimethylpent-2-enenitrile;

2-(4-(3-(6-(2,6-dichloro-3,5-dimethoxyphenyl)-2-(methylamino)-7-oxopyrido[2,3-d]pyrimidin-8(7H)-yl)-2,2-dimethylpropyl)piperazine-1-carbonyl)-4,4-dimethylpent-2-enenitrile;

2-(4-((1-((6-(2,6-dichloro-3,5-dimethoxyphenyl)-2-(methylamino)-7-oxopyrido[2,3-d]pyrimidin-8(7H)-yl)methyl)cyclopropyl)methyl)piperazine-1-carbonyl)-4,4-dimethylpent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperazine-1-carbonyl)-4-methylpent-2-enenitrile;

2-(3-((2-(6-(2,6-dichloro-3,5-dimethoxyphenyl)-2-(methylamino)-7-oxopyrido[2,3-d]pyrimidin-8(7H)-yl)ethyl)amino)azetidine-1-carbonyl)-4-methylpent-2-enenitrile;

2-(3-((2-(6-(2,6-dichloro-3,5-dimethoxyphenyl)-2-(methylamino)-7-oxopyrido[2,3-d]pyrimidin-8(7H)-yl)ethyl)(methyl)amino)azetidine-1-carbonyl)-4-methylpent-2-enenitrile;

2-cyano-N-(1-(3-(6-(2,6-dichloro-3,5-dimethoxyphenyl)-2-(methylamino)-7-oxopyrido[2,3-d]pyrimidin-8(7H)-yl)propyl)piperidin-3-yl)-4-methylpent-2-enamide;

2-cyano-N-(1-(3-(6-(2,6-dichloro-3,5-dimethoxyphenyl)-2-(methylamino)-7-oxopyrido[2,3-d]pyrimidin-8(7H)-yl)propyl)pyrrolidin-3-yl)-4-methylpent-2-enamide;

2-(3-((2-(6-(2,6-dichloro-3,5-dimethoxyphenyl)-2-(methylamino)-7-oxopyrido[2,3-d]pyrimidin-8(7H)-yl)ethyl)(ethyl)amino)azetidine-1-carbonyl)-4-methylpent-2-enenitrile;

2-(4-((2-(6-(2,6-dichloro-3,5-dimethoxyphenyl)-2-(methylamino)-7-oxopyrido[2,3-d]pyrimidin-8(7H)-yl)ethyl)(methyl)amino)piperidine-1-carbonyl)-4-methylpent-2-enenitrile;

2-(4-((2-(6-(2,6-dichloro-3,5-dimethoxyphenyl)-2-(methylamino)-7-oxopyrido[2,3-d]pyrimidin-8(7H)-yl)ethyl)(ethyl)amino)piperidine-1-carbonyl)-4-methylpent-2-enenitrile;

2-(3-(2-((6-(2,6-dichloro-3,5-dimethoxyphenyl)-2-(methylamino)-7-oxopyrido[2,3-d]pyrimidin-8(7H)-yl)methyl)pyrrolidin-1-yl)azetidine-1-carbonyl)-4-methylpent-2-enenitrile;

2-(4-(3-(6-(2,6-dichloro-3,5-dimethoxyphenyl)-2-(methylamino)-7-oxopyrido[2,3-d]pyrimidin-8(7H)-yl)-2,2-dimethylpropyl)piperazine-1-carbonyl)-4-methylpent-2-enenitrile;

2-(4-((1-((6-(2,6-dichloro-3,5-dimethoxyphenyl)-2-(methylamino)-7-oxopyrido[2,3-d]pyrimidin-8(7H)-yl)methyl)cyclopropyl)methyl)piperazine-1-carbonyl)-4-methylpent-2-enenitrile;

2-(4-(3-(6-(2,6-dichloro-3,5-dimethoxyphenyl)-2-(ethylamino)-7-oxopyrido[2,3-d]pyrimidin-8(7H)-yl)propyl)piperazine-1-carbonyl)-4,4-dimethylpent-2-enenitrile;

2-(3-((2-(6-(2,6-dichloro-3,5-dimethoxyphenyl)-2-(ethylamino)-7-oxopyrido[2,3-d]pyrimidin-8(7H)-yl)ethyl)amino)azetidine-1-carbonyl)-4,4-dimethylpent-2-enenitrile;

2-(3-((2-(6-(2,6-dichloro-3,5-dimethoxyphenyl)-2-(ethylamino)-7-oxopyrido[2,3-d]pyrimidin-8(7H)-yl)ethyl)(methyl)amino)azetidine-1-carbonyl)-4,4-dimethylpent-2-enenitrile;

2-cyano-N-(1-(3-(6-(2,6-dichloro-3,5-dimethoxyphenyl)-2-(ethylamino)-7-oxopyrido[2,3-d]pyrimidin-8(7H)-yl)propyl)piperidin-3-yl)-4,4-dimethylpent-2-enamide;

2-cyano-N-(1-(3-(6-(2,6-dichloro-3,5-dimethoxyphenyl)-2-(ethylamino)-7-oxopyrido[2,3-d]pyrimidin-8(7H)-yl)propyl)pyrrolidin-3-yl)-4,4-dimethylpent-2-enamide;

2-(3-((2-(6-(2,6-dichloro-3,5-dimethoxyphenyl)-2-(ethylamino)-7-oxopyrido[2,3-d]pyrimidin-8(7H)-yl)ethyl)(ethyl)amino)azetidine-1-carbonyl)-4,4-dimethylpent-2-enenitrile;

2-(4-((2-(6-(2,6-dichloro-3,5-dimethoxyphenyl)-2-(ethylamino)-7-oxopyrido[2,3-d]pyrimidin-8(7H)-yl)ethyl)(methyl)amino)piperidine-1-carbonyl)-4,4-dimethylpent-2-enenitrile;

2-(4-((2-(6-(2,6-dichloro-3,5-dimethoxyphenyl)-2-(ethylamino)-7-oxopyrido[2,3-d]pyrimidin-8(7H)-yl)ethyl)(ethyl)amino)piperidine-1-carbonyl)-4,4-dimethylpent-2-enenitrile;

2-(3-(2-((6-(2,6-dichloro-3,5-dimethoxyphenyl)-2-(ethylamino)-7-oxopyrido[2,3-d]pyrimidin-8(7H)-yl)methyl)pyrrolidin-1-yl)azetidine-1-carbonyl)-4,4-dimethylpent-2-enenitrile;

2-(4-(3-(6-(2,6-dichloro-3,5-dimethoxyphenyl)-2-(ethylamino)-7-oxopyrido[2,3-d]pyrimidin-8(7H)-yl)-2,2-dimethylpropyl)piperazine-1-carbonyl)-4,4-dimethylpent-2-enenitrile;

2-(4-((1-((6-(2,6-dichloro-3,5-dimethoxyphenyl)-2-(ethylamino)-7-oxopyrido[2,3-d]pyrimidin-8(7H)-yl)methyl)cyclopropyl)methyl)piperazine-1-carbonyl)-4,4-dimethylpent-2-enenitrile;

4-amino-2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methylpent-2-enenitrile;

4-amino-2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methylpent-2-enenitrile;

4-amino-2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methylpent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methyl-4-(methylamino)pent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methyl-4-(methylamino)pent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methyl-4-(methylamino)pent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methyl-4-(methyl(oxetan-3-yl)amino)pent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methyl-4-(methyl(oxetan-3-yl)amino)pent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methyl-4-(methyl(oxetan-3-yl)amino)pent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methyl-4-morpholinopent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methyl-4-morpholinopent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methyl-4-morpholinopent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-(4-ethylpiperazin-1-yl)-4-methylpent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-(4-ethylpiperazin-1-yl)-4-methylpent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-(4-ethylpiperazin-1-yl)-4-methylpent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-(3,3-difluoroazetidin-1-yl)-4-methylpent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-(3,3-difluoroazetidin-1-yl)-4-methylpent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-(3,3-difluoroazetidin-1-yl)-4-methylpent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methyl-4-(4-methylpiperazin-1-yl)pent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methyl-4-(4-methylpiperazin-1-yl)pent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methyl-4-(4-methylpiperazin-1-yl)pent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methyl-4-(2-oxa-6-azaspiro[3.3]heptan-6-yl)pent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methyl-4-(2-oxa-6-azaspiro[3.3]heptan-6-yl)pent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methyl-4-(2-oxa-6-azaspiro[3.3]heptan-6-yl)pent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methyl-4-(4-(oxetan-3-yl)piperazin-1-yl)pent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methyl-4-(4-(oxetan-3-yl)piperazin-1-yl)pent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methyl-4-(4-(oxetan-3-yl)piperazin-1-yl)pent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methyl-4-(4-methyl-3-oxopiperazin-1-yl)pent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methyl-4-(4-methyl-3-oxopiperazin-1-yl)pent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methyl-4-(4-methyl-3-oxopiperazin-1-yl)pent-2-enenitrile;

2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4-methyl-4-(3,4,5-trimethylpiperazin-1-yl)pent-2-enenitrile;

2-(4-(3-(6-(2,6-dichloro-3,5-dimethoxyphenyl)-2-(methylamino)-7-oxopyrido[2,3-d]pyrimidin-8(7H)-yl)propyl)piperidine-1-carbonyl)-4-methyl-4-(3,4,5-trimethylpiperazin-1-yl)pent-2-enenitrile;

2-(4-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4-methyl-4-(3,4,5-trimethylpiperazin-1-yl)pent-2-enenitrile;

or an individual (E) and (Z) isomers thereof;
or a pharmaceutically acceptable salt thereof of any of the above compounds including the individual (E) and (Z) isomers thereof.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of the present disclosure such as compound of Formula (I) where Q is as defined above and X is a group of formula (a), Y is CO, J' is $CR^1$ and other groups are as defined in the Summary can be prepared as illustrated and described in Scheme 1 below.

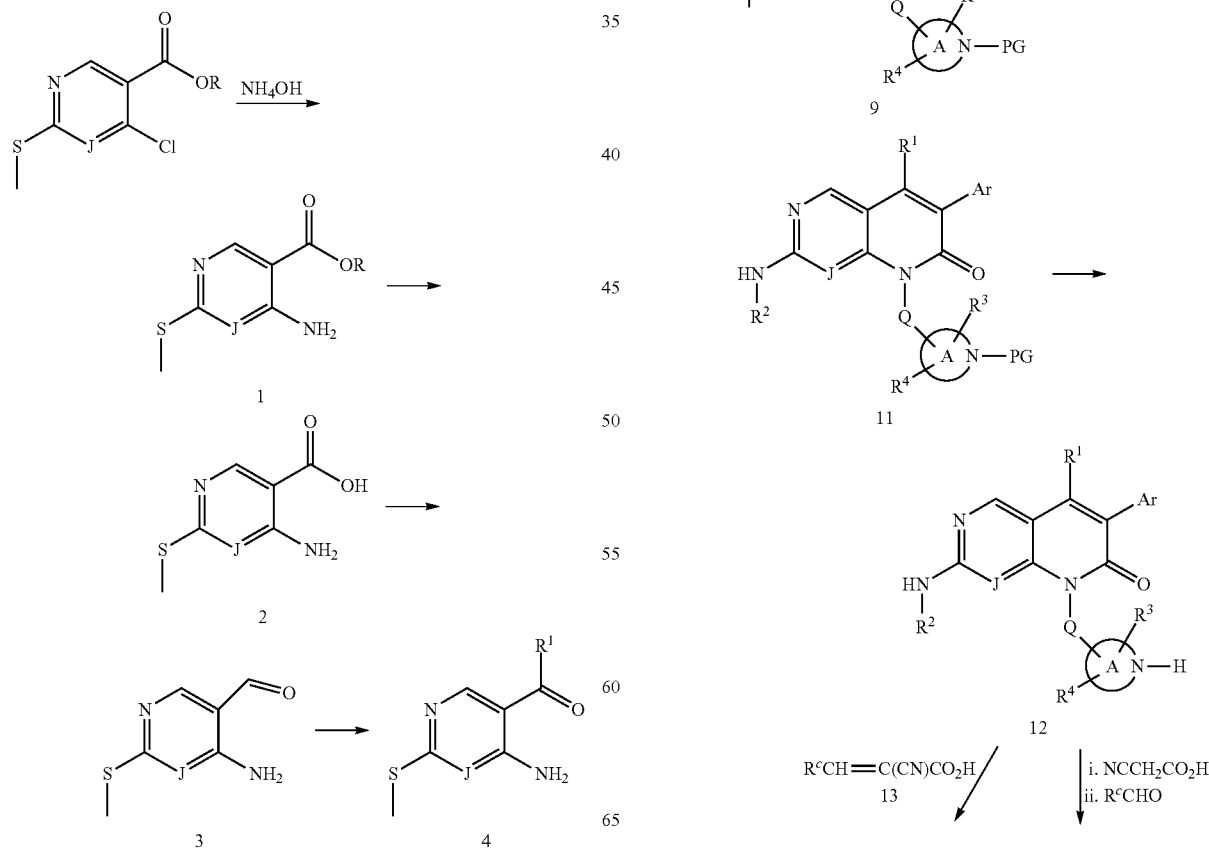

-continued

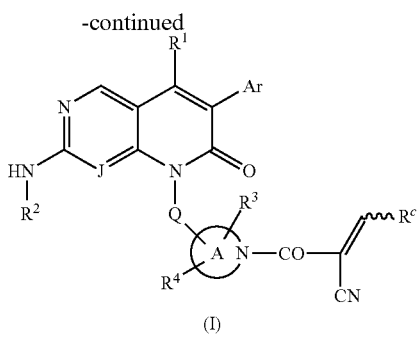

(I)

Substitution of the chlorine atom in ethyl 4-chloro-2-methylthiopyrimidine-5-carboxylate or ethyl 4-chloro-2-methylthiopyridin-5-carboxylate where (R is ethyl) with ammonia in an organic solvent such as dichloromethane, tetrahydrofuran (THF), N,N-dimethylformamide (DMF), N-methylpyrrolidine (NMP), methyl alcohol, and the like, provides an amino compound of formula 1. Reduction of the ester group in compound 1 to an alcohol with a reducing agent such as lithium aluminum hydride in a solvent such as THF or diethyl ether at 0° C. to room temperature provides a compound of formula 2.

Oxidation of the alcohol group in 2 provides an aldehyde of formula 3. The reaction is carried out under standard oxidation conditions well known in the art such as manganese dioxide (MnO$_2$) in solvents such as dichloromethane at 0° C. to 60° C. For compounds of Formula (I) where $R^1$ is alkyl, compound 3 can be treated with an alkyl lithium or alkyl magnesium halide in a solvent such as THF to generate a secondary alcohol which can then be oxidized under standard oxidation reaction conditions to provide a compound of formula 4.

Coupling of compound 3 or 4 with an ester compound of formula 5 where Ar is as defined in the first aspect above provides a quinolone compound of formula 6 where $R^1$ is hydrogen or alkyl, respectively. The coupling reaction is carried out in solvents such as N,N-dimethylformamide (DMF), N-methylpyrrolidine (NMP), and the like, using a base such as sodium hydride, sodium bicarbonate, lithium bicarbonate, potassium bicarbonate or triethylamine, and the like, at room temperature to 150° C. Compounds of formula 5 are either commercially available e.g. methyl 2-phenylacetate, methyl 2-(2-chlorophenyl)acetate, methyl 2-(2,4-dichlorophenyl)acetate, methyl 2-(2,6-dichlorophenyl)acetate, methyl 2-(3-methoxyphenyl)acetate and methyl 2-(3,5-dimethoxyphenyl)acetate are commercially available or can be readily prepared by methods well known in the art such as esterification of an aryl acetic acid to an aryl acetic ester under methanolic or ethanolic acidic (e.g. hydrogen chloride or sulfuric acid) conditions.

Reaction of a compound of formula 6 with a compound of formula 7 where Q, $R^3$, and $R^4$ are as defined in the first aspect above and PG is a suitable nitrogen protecting group under standard Mitsunobu reaction conditions (e.g. triphenylphosphine, diisopropylazo-dicarboxylate in solvents such as THF, DCM or DMF provides a compound of formula 8. Compounds of formula 7 are either commercially available e.g. tert-butyl 4-(3-hydroxypropyl)piperazine-1-carboxylate or can be readily prepared by methods well known in the art. Alternatively, the hydroxy group in 7 can be converted to a suitable leaving group such as tosylate, mesylate, or halo and then reacted with compound 6 in the presence of an organic base such as triethylamine, pyridine, and the like, to give a compound of formula 8. Such coversion methodology is well known in the art. Representative examples are provided in working examples below.

Oxidation of the methylthio group in compound 8 provides sulfone of formula 9, utilizing oxidizing agents such as 3-chloroperbenzoic acid (MCPBA) in dichloromethane or Oxone® in methanol, aqueous ethanol or aqueous tetrahydrofuran at 0° C. to room temperature. Alternatively, the oxidation may be carried out under catalytic conditions with rhenium/peroxide reagents, see ("Oxidation of Sulfoxides by Hydrogen Peroxide, Catalyzed by Methyltrioxorhenium (VII)", Lahi, David W.; Espenson, James H, Inorg. Chem (2000) 39(10) pp. 2164-2167; "Rhenium oxo complexes in catalytic oxidations, Catal. Today (2000) 55(4), pp 317-363 and "A Simple and Efficient Method for the Preparation of Pyridine N-Oxides", Coperet, Christophe; Adolfsson, Hans; Khuong, Tinh-Alfredo V.; Yudin, Andrei K.; Sharpless, K. Barry, J. Org. Chem. (1998) 63(5), pp 1740-1741).

Coupling of the sulfone compound 9 with an amine of formula 10 where $R^2$ is as defined in the first aspect above in a solvent such as DMF or NMP at temperatures of 80° C. to 150° C. provides a compound of formula 11. Compounds of formula 10 are either commercially available e.g., methylamine, $N^1,N^1$-diethylbutane-1,4-diamine, 2-aminoethanol, prop-2-yn-1-amine, 1-amino-2-methylpropan-2-ol, cyclopropylmethanamine, aniline, 2-ethoxyethanamine, pyridin-2-amine, 2,2-difluoroethanamine, tetrahydro-2H-pyran-4-amine, 1,3-dimethoxypropan-2-amine, (S)-1-methoxypropan-2-amine, 2-isopropoxyethanamine, (tetrahydrofuran-2-yl)methanamine, (R)-tetrahydrofuran-3-amine, 2-methoxyethanamine, 1-(3-aminopropyl)pyrrolidin-2-one, 2-(2-methoxyethoxy)ethanamine, (1r,4r)-4-aminocyclohexanol, oxetan-3-amine, 1-amino-2-methylpropan-2-ol, 2-morpholinoethanamine and 2-(4-methylpiperazin-1-yl)ethanamine or can be readily prepared by methods well known in the art.

Removal of the amino protecting group in compound 11 provides a compound of formula 12. The reaction conditions depend on nature of the amino protecting group. For example, when PG is Boc, it can be removed by treating a compound of formula 11 with an acid e.g. hydrogen chloride or trifluoroacetic acid in solvents such as DCM.

Compound 12 can be then converted to a compound of Formula (I) by methods well known in the art. For example, compounds of Formula (I) where Y is —CO— can be prepared by first condensing compound 12 with 2-cyanoacetic acid under standard amide coupling conditions such as carbon diimidazole (CDI), DCC, EDC or HATU and the like, or an acid derivative thereof in the presence of a base (e.g. TEA or DIEA) in solvents such as THF or DCM and reacting the resulting cyanoacetyl compound with an aldehyde of formula $R^c$CHO where $R^c$ is as defined in the Summary under standard condensation reaction conditions such as using a base such as piperidine and the like, in the presence or absence of acetic acid and the like, in solvents such as ethanol, dioxane, and the like at temperatures ranging from room temperature to reflux then provides a compound of Formula (I). Compounds of formula $R^c$CHO are commercially available or they can be prepared by methods well known in the art e.g. such as, e.g., acetaldehyde, cyclopropylaldehyde, isobutyraldehyde, 3-methyloxetane-3-carbaldehyde, 2-(dimethylamino)-2-methylpropanal, 2-methyl-2-(1-piperidyl)propanal, tert-butyl (2S)-2-formylpyrrolidine-1-carboxylate and 2-methyl-2-(morpholin-4-yl)propanal are commercially available. Ethoxy-2-methylpropanal was prepared from isobutyraldehyde as described in PCT Int. Appl., 2007142576.

Compound 12 can also be condensed with a precursor group of R$^c$CHO and then converted to a compound of Formula (I). For example, 12 can be condensed with tert-butyl (1-formylcyclopropyl)-carbamate (prepared by oxidation of tert-butyl (1-(hydroxymethyl)-cyclopropyl)carbamate see Bioorg. Med. Chem. Lett., 2008, 18(6), 2188, with Dess Martin periodinane) or tert-butyl 2-methyl-1-oxopropan-2-ylcarbamate following by removal of the amino protecting group to give a compound of Formula (I) where R$^1$ is 1-methylcycloprop-1-yl or 2-methypropan-2-yl. The condensation reaction can be also be carried out by adding the desired aldehyde with a base such as pyrrolidine or piperidine with or without chlorotrimethylsilane in dichloromethane or other suitable solvent (e.g. dioxane and ethanol).

Alternatively, compounds of Formula (I) where X is —CO— can be prepared by reacting compound 12 with an acid of formula 13 or an acid derivative thereof where R$^1$ is as defined in the Summary under amide coupling conditions.

It will be apparent to a person skilled in the art that compound of Formula (I) where X is a group of formula (b), (c) or (d) can be readily prepared by substituting compound 7 with a suitable starting material.

Testing

The FGFR kinase inhibitory activity of the compounds of the present disclosure can be tested using the in vitro and in vivo assays described in Biological Examples 1-4, 8, 10, 11 below and the residence time of the compound FGFR bound complex can be tested using the Biological Example 9 below. A determination of kinase inhibitory activity by any of those assays is considered to be kinase inhibitory activity within the scope of this disclosure even if any or all of the other assays do not result in a determination of kinase inhibitory activity. The ability of the compound of the disclosure to form reversible covalent bond with a cysteine residue of a kinase, in particular Cys488 of FGFR1 (UniprotKB Sequence ID P11362), Cys491 (UniprotKB Sequence ID P21802) of FGFR2, Cys482 (UniprotKB Sequence ID P22607) of FGFR3, and Cys477 (UniprotKB Sequence ID P22455) of FGFR4 can be determined by the assays described in Examples 5-7 below.

Without being bound to any specific mechanistic theory, it is believed that the cysteine sulfhydryl group and a carbon atom forming part of the carbon-carbon double bond in the group —N—Y—C(CN)=CHR$^c$ (see Formula I) of the compound of the present disclosure can form a reversible, i.e., labile, covalent bond, defined herein, such as wherein Cys488 of FGFR1, Cys491 of FGFR2, Cys482 of FGFR3, or Cys477 of FGFR4, attacks an electron deficient carbon atom of the carbon-carbon double bond in the group —N—Y—C(CN)=CHR$^c$ in the compound of present disclosure to form a thiol adduct.

In some embodiments, the electron deficient carbon atom of the olefin is distal to the carbon attached to the cyano group and to the electron withdrawing —N—Y— moiety (see Formula I) in the compounds of the present disclosure. Therefore, the combination of the cyano and the "—N—Y—" moieties and the olefinic moiety to which they are bonded in the compounds of the present disclosure can increase the reactivity of the olefin to form a thiol adduct with the active site cysteine residue in FGFR 1, 2, 3, and 4.

The compounds of the present disclosure bind with at least one of FGFR 1, 2, 3 and -4 in two different manners. In addition to the labile covalent binding, discussed above, they also form non-covalent binding (e.g., via van der Waals binding, hydrogen binding, hydrophobic binding, hydrophilic binding, and/or electrostatic charge binding) with FGFR 1, 2, 3 and -4, the non-covalent binding being sufficient to at least partially inhibit the kinase activity of the FGFR1, 2, 3 and 4, respectively.

As mentioned herein, the labile covalent binding between the the compound of the disclosure and at least one of FGFR1, 2, 3 and -4 occurs between the olefin carbon in the inhibitor and the thiol (sulfydryl) of cysteine 488 of FGFR1, 491 of FGFR2, 482 of FGFR3, and 477 of FGFR4 respectively, residue thiol side chain at or near the site where the compound has the aforementioned non-covalent binding with the FGFR1, 2, 3 and 4, respectively.

As is evident, the compounds of the present disclosure can have both a cysteine-mediated covalent binding and a non-covalent binding with at least one of FGFR1-4. This is in contrast with non-covalent reversible inhibitors which inhibit the FGFR1-4 only via non-covalent binding and lack the cysteine-mediated covalent binding.

The result of the binding of the compounds of the present disclosure with FGFR1-4 in the two different manners is a reversible covalent inhibitor having a slow off-rate and a protracted duration of action, in some instances comparable to an irreversible covalent inhibitor without forming permanent irreversible protein adducts. The difference between irreversible and reversible covalent inhibitors, particularly the compounds disclosed herein, can be ascertained utilizing assays disclosed herein.

In general, the binding involved in an inhibitor that forms a reversible covalent bond with FGFR1-4, i.e., the compounds disclosed herein, is stable when the FGFR1-4 is in certain configurations and susceptible to being broken when the FGFR1-4 is in different configurations (in both cases under physiologic conditions), whereas the interaction between an inhibitor that forms an irreversible covalent bond is stable under physiologic conditions even when the FGFR1-4 is in different configurations.

A reversible covalent bond often imparts unique properties related to the residence time of the compound within the cysteine-containing binding site. In this context, residence time refers to the temporal duration of the compound-target complex under different conditions (see Copeland R A, Pompliano D L, Meek T D. Drug-target residence time and its implications for lead optimization. Nat. Rev. Drug Discov. 5(9), 730-739 (2006)).

The formation of a reversible covalent bond in a compound as disclosed herein can lead to an extended residence time when compared to a compound that does not form a covalent bond with FGFR1-4. In one embodiment disclosed herein the compounds of the present disclosure that are reversible covalent inhibitors have a residence time of at least about 1 h, Residence time may be measured using an occupancy assay in a biochemical or cellular environment (see Biological Examples 9, 10 below). Additionally, residence time may be measured using a functional assay following a defined wash-out period.

Compounds that form an irreversible covalent bond in an irreversible covalent inhibitor share these extended residence time properties but may nonetheless be differentiated from reversible covalent inhibitor using a reversibility assay. The ability of the compound of the disclosure to form reversible covalent bond with Cys488 of FGFR1, Cys491 of FGFR2, Cys482 of FGFR3, and Cys477 of FGFR4 and the olefinic bond in the compound of the disclosure, can be determined by the assays described in Biological Examples 5-7 below. A determination of the binding reversibility of the covalent bond between the cysteine residue and the olefinic bond of the compound of the disclosure by any of Biological Examples 5-7 below is considered to be binding reversibility within the scope of this disclosure even if one or more of the other methods does not result in a determination of binding reversibility.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, axitinib; EGFR inhibitor such as afatinib, brivanib, carbozatinib, erlotinib, gefitinib, neratinib, lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, TG100-115; MTOR inhibitor such as rapamycin (sirolimus), temsirolimus, everolimus, XL388, XL765, AZD2013, PF04691502, PKI-587, BEZ235, GDC0349; MEK inhibitor such as AZD6244, trametinib, PD184352, pimasertinib, GDC-0973, AZD8330; and proteasome inhibitor such as carfilzomib, MLN9708, delanzomib, or bortezomib.

Other anti-cancer agents that can be employed in combination with a compound of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of the disclosure such as 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one used to determine the anti-tumor activity in HGS and RT4 tumor models (Example 4 below: In HGS model, vehicle dosed group reached tumor size 645 dosing at day 42 after inoculation whereas for animals treated with 20/kg of compound, the tumor size was 55 mm3 showing significant antitumor activity and induced tumor regression), include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine octfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+-53-iethylstilbe cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., cytarabine), purine analogs (e.g., mercaptopurine, thioguanine, pentostatin).

Examples of natural products useful in combination with a compound of this disclosure include but are not limited to vinca alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of this disclosure) include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, cytarabine), purine analogs (e.g., mercaptopurine, thioguanine, pentostatin.

Examples of hormones and antagonists useful in combination a compound of this disclosure include, but are not limited to, adrenocorticosteroids (e.g., prednisone), progestins (e.g., hydroxyprogesterone caproate, megestrol acetate, medroxyprogesterone acetate), estrogens (e.g., -55-iethyl-stilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HC1), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

EXAMPLES

The following preparations of compounds of Formula (III) and intermediates (References) are given to enable those skilled in the art to more clearly understand and to practice the present disclosure. They should not be considered as limiting the scope of the disclosure, but merely as being illustrative and representative thereof.

Reference 1

Synthesis of 6-(2-chlorophenyl)-2-(methylthio) pyrido[2,3-d]pyrimidin-7(8H)-one

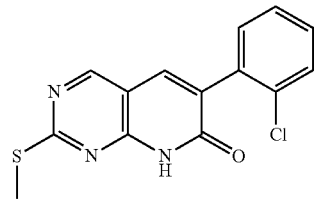

Step 1

To a solution of ethyl 4-chloro-2-(methylthio)pyrimidine-5-carboxylate (30 g, 129.3 mmol, 1.00 equiv) and Et₃N (51 mL) in THF (225 mL) was added NH₃.H₂O (300 mL). The resulting mixture was stirred at rt overnight. The mixture was concentrated and diluted with EtOAc. The organic phase was washed with sat. NaHCO₃ solution and brine, dried over anhydrous sodium sulfate. The solids were filtered and concentrated under vacuum to give 26.8 g (97%) of ethyl 4-amino-2-(methylthio)pyrimidine-5-carboxylate as a white solid.

Step 2

To a suspension of LiAlH₄ (10.53 g, 277.0 mmol, 2.2 equiv) in THF (500 mL) was added drop wise ethyl 4-amino-2-(methylthio)pyrimidine-5-carboxylate (26.8 g, 126.0 mmol, 1.0 equiv) in THF (500 mL) at 0° C. The resulting mixture was stirred at 0° C. for 5 h. The reaction was quenched with 15% NaOH solution. The mixture was stirred for 1 h. The white precipitate was removed by filtration, washing with EtOAc. The filtrate was concentrated under vacuum to give 22 g (crude) of (4-amino-2-(methylthio)pyrimidin-5-yl)methanol as a white solid.

Step 3

To a solution of (4-amino-2-(methylthio)pyrimidin-5-yl)methanol (11 g, 63 mmol, 1.0 equiv) in $CHCl_3$ (900 mL) was added $MnO_2$ (43.85 g, 504 mmol, 8.0 equiv). The suspension was stirred overnight at rt. The resulting mixture was filtration and washing with $CHCl_3$. The filtrate was concentrated under vacuum to give 10 g (94%) of 4-amino-2-(methylthio)pyrimidine-5-carbaldehyde as a white solid.

Step 4

A solution of 4-amino-2-(methylthio)pyrimidine-5-carbaldehyde (20 g, 119 mmol, 1.0 equiv), $K_2CO_3$ (49.26 g, 357 mmol, 3.0 equiv) and methyl 2-(2-chlorophenyl)acetate (32.84 g, 178.5 mmol, 1.5 equiv) in NMP (130 ml) was stirred at 110° C. overnight. The reaction was diluted with EtOAc and water and extracted with EtOAc. The organic phase washed with brine, dried and concentrated. The residue was purified by column chromatography using EtOAc/PE (1/3) to give. 19 g (53%) of 6-(2-chlorophenyl)-2-(methylthio)pyrido[2, 3-d]pyrimidin-7(8H)-one as a yellow solid.

Reference 2

Synthesis of 6-(2,6-dichloro-3,5-dimethoxy-phenyl)-2-(methylsulfanyl)-7H,8H-pyrido[2,3-d]pyrimidin-7-one

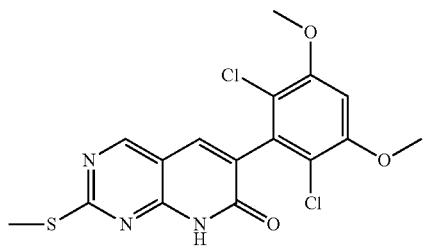

Step 1

Into a 500-mL 3-necked round-bottom flask, which was purged and maintained with an inert atmosphere of nitrogen, was placed a solution of 1,3-dimethoxy-5-methylbenzene (5 g, 32.85 mmol, 1.00 equiv) in dichloromethane (150 mL). This was followed by the addition of sulfuroyl dichloride (8.869 g, 65.71 mmol, 2.00 equiv) drop wise with stirring at 0° C. The resulting solution was stirred overnight at room temperature. The pH value of the solution was adjusted to 8 with sodium carbonate (sat. aq.). The resulting solution was extracted with dichloromethane, and the combined organic layers were concentrated under vacuum. The resulting mixture was washed with hexane to give 5.36 g (74%) of 2,4-dichloro-1,5-dimethoxy-3-methylbenzene as a white solid.

Step 2

Into a 1 L round-bottom flask, was placed a solution of 2,4-dichloro-1,5-dimethoxy-3-methylbenzene (35 g, 158.31 mmol, 1.00 equiv) in tetrachloromethane (600 mL). NBS (31 g, 174.18 mmol, 1.10 equiv) and AIBN (3.5 g, 21.31 mmol, 0.13 equiv) were added to the reaction mixture. The resulting solution was heated to reflux for 3 h. The reaction was then quenched by the addition of sodium carbonate (sat. aq.). The organic layer was washed with sodium chloride (sat.). The resulting mixture was concentrated under vacuum to give 38 g (80%) of 3-(bromo-methyl)-2,4-dichloro-1,5-dimethoxybenzene as a yellow solid.

Step 3

Into a 1 L round-bottom flask, was placed a solution of 3-(bromomethyl)-2,4-dichloro-1,5-dimethoxybenzene (47 g, 156.68 mmol, 1.00 equiv) in DMSO (500 mL). Sodium cyanide (8.445 g, 172.32 mmol, 1.10 equiv) was added to the reaction mixture. The resulting solution was stirred overnight at 35° C. The reaction was then quenched with sodium bicarbonate (sat. aq.). The resulting solution was extracted with ethyl acetate. The combined organic layers were washed with water and concentrated. The residue was applied onto a silica gel column with ethyl acetate/petroleum ether (1:10) as eluent to yield 20 g (52%) of 2-(2,6-dichloro-3,5-dimethoxy-phenyl)acetonitrile as a white solid.

Step 4

Into a 100-mL round-bottom flask, was placed a solution of 4-amino-2-(methylsulfanyl)-pyrimidine-5-carbaldehyde (2.0 g, 11.82 mmol, 1.00 equiv) in DMF (40 mL). 2-(2,6-Dichloro-3,5-dimethoxyphenyl)acetonitrile (4.08 g, 16.58 mmol, 1.40 equiv), and potassium carbonate (4.90 g, 35.20 mmol, 3.00 equiv) were added and the resulting solution was stirred for 12 h at 100° C. in an oil bath, and then it was quenched with water. The resulting solution was extracted with ethyl acetate, and the combined organic layers were dried over anhydrous sodium sulfate and concentrated under vacuum. The residue was applied onto a silica gel column with ethyl acetate/petroleum ether (1:2) as eluent to yield 1.65 g (35%) of 6-(2,6-dichloro-3,5-dimethoxy-phenyl)-2-(methylsulfanyl)-7H,8H-pyrido[2,3-d]pyrimidin-7-imine as a yellow solid.

Step 5

Into a 50-mL round-bottom flask, was placed a solution of 6-(2,6-dichloro-3,5-dimethoxy-phenyl)-2-(methylsulfanyl)-7H,8H-pyrido[2,3-d]pyrimidin-7-imine (1.60 g, 4.03 mmol, 1.00 equiv) in acetic acid (40 mL). $NaNO_2$ (1.50 g, 21.74 mmol, 5.00 equiv) was added to the reaction mixture. The resulting solution was stirred for 2 h at 70° C., and then it was quenched with water. The solids were collected by filtration to give 1.25 g (78%) of 6-(2,6-dichloro-3,5-dimethoxy-phenyl)-2-(methylsulfanyl)-7H,8H-pyrido[2,3-d]pyrimidin-7-one as a yellow solid.

Reference 3

Synthesis of 6-(3,5-dimethoxyphenyl)-2-(methylthio)pyrido[2,3-d]pyrimidin-7(8H)-one

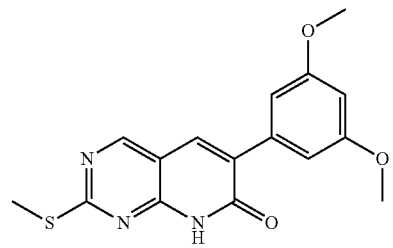

Step 1

To a solution of 2-(3,5-dimethoxyphenyl)acetic acid (7.5 g, 38.2 mmol) in MeOH (30 mL) was added $SOCl_2$ (1 mL) at 0° C. The mixture was stirred at room temperature for 2 h, and then it was concentrated under vacuum to give a residue. The residue was re-dissolved in EtOAc (100 mL), and the mixture was washed NaHCO₃, the organic layer was dried over Na₂SO₄, filtered and concentrated to give methyl 2-(3,5-dimethoxyphenyl)acetate (8.1 g, 100%) as a colorless oil.

Step 2

To a solution of methyl 2-(3,5-dimethoxyphenyl)acetate (3.38 g, 20 mmol), and 4-amino-2-(methylthio)pyrimidine-5-carbaldehyde (6.3 g, 30 mmol) in NMP (20 mL) was added K₂CO₃ (5.5 g, 40 mmol) and the mixture was stirred at 70° C. overnight. H₂O (50 mL) was added and the mixture was filtered, the filtered cake was washed with EtOAc and dried to give 6-(3,5-dimethoxyphenyl)-2-(methylthio)pyrido[2,3-d]pyrimidin-7(8H)-one (6.5 g, 99%) as a light yellow solid.

Reference 4

Synthesis of 6-(2-chloro-3,5-dimethoxyphenyl)-2-(methylthio)pyrido[2,3-d]pyrimidin-7(8H)-one

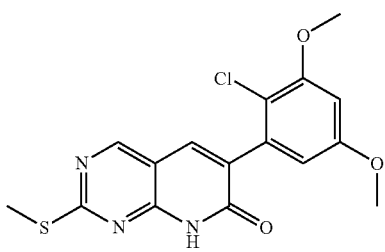

Step 1

To a solution of 2-(3,5-dimethoxyphenyl)acetic acid (25 g, 127.6 mmol) in H₂O/MeCN (200/200 mL) was added Oxone (78.5 g, 127.6 mmol) and KCl (9.5 g, 127.6 mmol), and the mixture was stirred at room temperature for 2 h. The mixture was filtered, EtOAc was added to the filtrate, and the H₂O layer was separated. The organic layer was concentrated to give a residue, which was dissolved in NaOH, washed with EtOAc, then the H₂O layer was adjusted to pH=5-6 with concentrated HCl (aq). The solid was filtered and the filtered cake was dried to give 2-(2-chloro-3,5-dimethoxyphenyl)acetic acid (26.5 g, 90%) as a light yellow solid.

Step 2

To a solution of 2-(2-chloro-3,5-dimethoxyphenyl)acetic acid (26.5 g, 114.9 mmol) in MeOH (100 mL) was added SOCl₂ (2 mL) at 0° C. The mixture was stirred at room temperature for 2 h, and then concentrated under vacuum to give a residue. The residue was re-dissolved in EtOAc, and the mixture was washed NaHCO₃. The organic layer was dried over Na₂SO₄, filtered and concentrated to give methyl 2-(2-chloro-3,5-dimethoxyphenyl)acetate (28.1 g, 100%) as a white solid.

Step 3

To a solution of 4-amino-2-(methylthio)pyrimidine-5-carbaldehyde (12.5 g, 74 mmol), and methyl 2-(2-chloro-3,5-dimethoxyphenyl)acetate (28 g, 114.5 mmol) in NMP (30 mL) was added K₂CO₃ (20.5 g, 148 mmol) and the mixture was stirred at 70° C. overnight. H₂O was added, the mixture was filtered and the filtered cake was washed with EtOAc. The filtered cake was dried to give 6-(2-chloro-3,5-dimethoxyphenyl)-2-(methylthio)pyrido[2,3-d]pyrimidin-7(8H)-one (14.8 g, 55%) as an off-white solid.

Reference 5

Synthesis of Tert-butyl 4-(2-iodoethoxy)piperidine-1-carboxylate

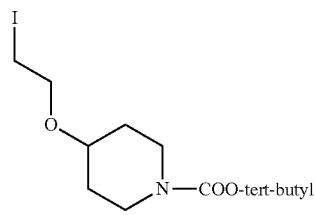

Step 1

To a mixture of NaH (1 g, 25.00 mmol, 1.00 equiv) in THF (100 mL) was added tert-butyl 4-hydroxypiperidine-1-carboxylate (5 g, 24.84 mmol, 1.00 equiv). The reaction mixture was stirred for 20 min at 0° C. and then methyl 2-bromoacetate (3.8 g, 24.84 mmol, 1.00 equiv) was added. The resulting solution was stirred overnight at room temperature and then quenched with H₂O. The resulting solution was extracted with ethyl acetate and the organic layers combined and washed with (sat.) NaCl. The mixture was dried over anhydrous sodium sulfate and concentrated. The residue was purified by chromatography (DCM/MeOH (10:1)) to give 3 g (44%) of tert-butyl 4-(2-methoxy-2-oxoethoxy)piperidine-1-carboxylate as a colorless oil.

Step 2

To a solution of LAH (500 mg, 13.18 mmol, 1.20 equiv) in THF (100 mL) at 0° C. was added tert-butyl 4-(2-methoxy-2-oxoethoxy)piperidine-1-carboxylate (3 g, 10.98 mmol, 1.00 equiv) in THF (50 mL) drop wise. The resulting solution was stirred for 2 h at room temperature and then quenched with 15% NaOH (2 mL). The resulting solution was extracted with ethyl acetate and the organic layers combined and washed with sat. NaCl. The mixture was dried over anhydrous sodium sulfate and concentrated to give 2 g (74%) of tert-butyl 4-(2-hydroxyethoxy)-piperidine-1-carboxylate as a colorless oil.

Step 3

To a solution of tert-butyl 4-(2-hydroxyethoxy)piperidine-1-carboxylate (2 g, 8.15 mmol, 1.00 equiv) in DCM (100 mL) was added I₂ (3.1 g, 1.50 equiv), imidazole (0.8 g, 1.50 equiv), and PPh₃ (3.2 g, 12.20 mmol, 1.50 equiv). The resulting solution was stirred for 2 h at room temperature and then concentrated. The residue was purified by chromatography (EtOAc/pet. ether (4:1)) to give 2 g (69%) of tert-butyl 4-(2-iodoethoxy)piperidine-1-carboxylate as a light yellow oil.

Reference 6

Synthesis of tert-butyl 3-(2-iodoethoxy)piperidine-1-carboxylate

Proceeding as described above but substituting tert-butyl 3-hydroxypiperidine-1-carboxylate for tert-butyl 4-hydroxypiperidine-1-carboxylate, 3-(2-iodoethoxy)piperidine-1-carboxylate was prepared.

Reference 7

Synthesis of (3R,5S)-tert-butyl 3,5-dimethyl-4-(3-((methylsulfonyl)oxy)propyl)piperazine-1-carboxylate

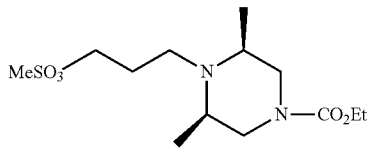

Step 1

A mixture of (3S,5R)-tert-butyl 3,5-dimethylpiperazine-1-carboxylate (2.14 g, 10.0 mmol), 3-bromopropan-1-ol (2.76 g, 20 mmol) and $K_2CO_3$ (2.76 g, 20 mmol) in DMF (5.0 mL) was heated to 90° C. for 2 h in a microwave. The reaction mixture was poured into water (30 mL) and extracted with EtOAc. The organic phase was separated, dried and concentrated. The residue was purified by chromatography (DCM:MeOH=30:1) to provide (3R,5S)-tert-butyl 4-(3-hydroxypropyl)-3,5-dimethylpiperazine-1-carboxylate as a yellow liquid (2.14 g, 50%).

Step 2

To a solution of (3R,5S)-tert-butyl 4-(3-hydroxypropyl)-3,5-dimethylpiperazine-1-carboxylate (680 mg, 5.0 mmol) and TEA (505 mg, 5.0 mmol) in DCM (30 mL) at room temperature was added drop wise MSCl (428 mg, 3.75 mmol). The reaction mixture was then washed with water and brine. The organic phase was dried, filtered and concentrated. The residue was purified by chromatography (DCM:MeOH=50:1) to provide (3R,5S)-tert-butyl 3,5-dimethyl-4-(3-((methylsulfonyl)oxy)propyl)piperazine-1-carboxylate as a yellow liquid (700 mg, 80%).

Reference 8

Synthesis of Tert-butyl 4-[[1-(iodomethyl)-cyclopropyl]methyl]piperazine-1-carboxylate

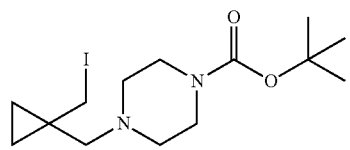

Step 1

Into a solution of [1-(hydroxymethyl)cyclopropyl]methanol (9.5 g, 93.02 mmol,) and $CCl_4$ (15.57 g, 102.43 mmol) in THF (50 mL) at 0° C. was added [bis(dimethylamino)phosphanyl]-dimethylamine (16.70 g, 102.33 mmol). The resulting solution was stirred overnight at room temperature and then quenched by the addition of water. The resulting solution was extracted with DCM and the organic layers combined. The resulting mixture was washed with sat. NaCl and dried over $Na_2SO_4$ and then concentrated. The residue was purified by chromatography (EtOAc/pet. ether (1:1) to afford 5.2 g (46%) of [1-(chloromethyl)cyclopropyl]methanol as yellow oil.

Step 2

A mixture of [1-(chloromethyl)cyclopropyl]methanol (5.2 g, 43.13 mmol), tert-butyl piperazine-1-carboxylate (8.87 g, 47.62 mmol), $K_2CO_3$ (17.94 g, 129.80 mmol) and KI (360 mg, 2.17 mmol) in acetone (100 mL) was stirred overnight at 60° C. The resulting mixture was then cooled and concentrated. The residue was purified by chromatography (EtOAc/pet. ether (2:1) to afford 4 g (34%) of tert-butyl 4-[[1-(hydroxymethyl)cyclopropyl]methyl]piperazine-1-carboxylate as light yellow oil.

Step 3

A solution of tert-butyl 4-[[1-(hydroxymethyl)cyclopropyl]methyl]piperazine-1-carboxylate (1 g, 3.70 mmol), PPh3 (2.91 g, 11.09 mmol), imidazole (760 mg, 11.18 mmol), and $I_2$ (2.82 g, 11.10 mmol, 3.00 equiv) in DCM (50 mL) was stirred for 2 h at room temperature. The solids were filtered and the resulting mixture was concentrated. The residue was purified by chromatography (DCM/EtOAc (10:1) to afford 800 mg (57%) of tert-butyl 4-[[1-(iodomethyl)cyclopropyl]methyl]piperazine-1-carboxylate as brown oil.

Reference 9

Synthesis of Tert-butyl 4-[3-(methanesulfonyloxy)-2,2-dimethylpropyl]piperazine-1-carboxylate

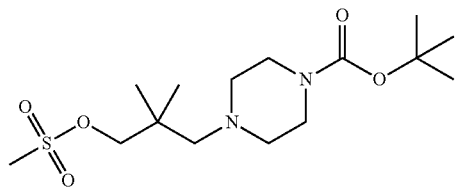

Step 1

To a solution of tert-butyl piperazine-1-carboxylate (2.9 g, 15.57 mmol) in AcOH (8 mL) was added formalin (35% wt. (1.5 mL)). The resulting solution was stirred at RT for 30 min and then 2-methylpropanal (1.5 mL) was added. The resulting solution was stirred for 12 h at 50° C. and then concentrated. The resulting solution was extracted with EtOAc and the organic layers combined. The organic layer was washed with sat. $NaHCO_3$ and then concentrated to afford 3.6 g (86%) of tert-butyl 4-(2,2-dimethyl-3-oxopropyl)piperazine-1-carboxylate as a colorless semi-solid.

Step 2

A solution of tert-butyl 4-(2,2-dimethyl-3-oxopropyl)piperazine-1-carboxylate (3.6 g, 13.32 mmol) and $NaBH_4$ (0.5 g) in isopropanol (10 mL) was stirred for 4 h at room temperature. The reaction was then quenched with water. The resulting mixture was concentrated and the residue was purified by chromatography (DCM/EtOAc (10:1) to afford 3 g (83%) of tert-butyl 4-(3-hydroxy-2,2-dimethylpropyl)piperazine-1-carboxylate as a white solid.

Step 3

To a solution of tert-butyl 4-(3-hydroxy-2,2-dimethylpropyl)piperazine-1-carboxylate (1.2 g, 4.41 mmol) and TEA (2 mL) in DCM (10 mL) was added MSCl (700 mg, 6.14 mmol) drop wise. The resulting solution was stirred for 3 h at room temperature and then concentrated. The residue was purified by chromatography (DCM/Acetone (1:50)) to afford 0.4 g (26%) of tert-butyl 4-[3-(methanesulfonyloxy)-2,2-dimethylpropyl]piperazine-1-carboxylate as a yellow oil.

Reference 10

Synthesis of 6-(2-chloro-6-fluoro-3,5-dimethoxyphenyl)-2-(methylsulfanyl)-7H,8H-pyrido[2,3-d]pyrimidin-7-one

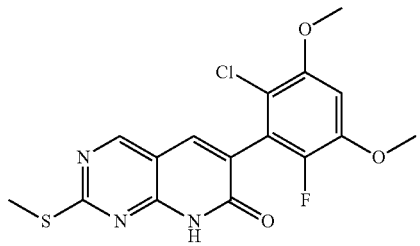

Step 1

To a solution of 1,3-dimethoxy-5-methylbenzene (4 g, 26.28 mmol) in ACN (60 mL) at 0° C. was added Selectfluor (8.4 g, 23.73 mmol) drop wise with stirring. The resulting solution was stirred overnight at room temperature and then quenched with water. The resulting solution was extracted with DCM and the organic layers combined and concentrated. The residue was purified by chromatography (ethyl acetate/pet. ether (1:20)) to afford 1.5 g (34%) of 2-fluoro-1,5-dimethoxy-3-methylbenzene as colorless oil.

Step 2

To a solution of 2-fluoro-1,5-dimethoxy-3-methylbenzene (1.5 g, 8.81 mmol) in DCM (30 mL) was added a solution of sulfuroyl dichloride (1.19 g, 8.82 mmol) in DCM (20 mL) drop wise with stirring at 0° C. The resulting solution was stirred for 1 h at room temperature. The pH value of the solution was adjusted to 9 with sat. NaHCO$_3$. The resulting solution was extracted with DCM and the organic layers were combined and concentrated. The residue was purified by chromatography (EtOAc/pet. ether (1:7)) to afford 1.2 g (67%) of 2-chloro-4-fluoro-1,5-dimethoxy-3-methylbenzene as a white solid.

Step 3

A solution of 2-chloro-4-fluoro-1,5-dimethoxy-3-methylbenzene (1.2 g, 5.86 mmol), NBS (1.04 g, 5.84 mmol) and AIBN (380 mg, 2.31 mmol) in CCl4 (40 mL) was heated to reflux for 4 hr. The reaction was quenched with sat. NaHCO$_3$ and extracted with DCM. The organic layers were combined and concentrated to afford 1.4 g (84%) of 3-(bromomethyl)-2-chloro-4-fluoro-1,5-dimethoxybenzene as a yellow solid.

Step 4

To a solution of 3-(bromomethyl)-2-chloro-4-fluoro-1,5-dimethoxybenzene (1.4 g, 4.94 mmol) in DMSO (30 mL) was added NaCN (240 mg, 4.90 mmol). The resulting solution was stirred overnight at 35° C. and then quenched with sat. NaHCO$_3$. The solution was extracted with DCM and the organic layers combined and washed with water and then concentrated. The residue was purified by chromatography (DCM/pet. ether (75:100)) to afford 510 mg (45%) of 2-(2-chloro-6-fluoro-3,5-dimethoxyphenyl)acetonitrile as a white solid.

Step 5

To a solution of 2-(2-chloro-6-fluoro-3,5-dimethoxyphenyl)acetonitrile (510 mg, 2.22 mmol) in DMF (40 mL) was added K$_2$CO$_3$ (920 mg, 6.66 mmol), Cs$_2$CO$_3$ (720 mg, 2.21 mmol) and 4-amino-2-(methylsulfanyl)pyrimidine-5-carbaldehyde (380 mg, 2.25 mmol). The resulting solution was stirred for 3 h at 85° C. and then diluted with water. The resulting solution was extracted with DCM and the organic layers combined, washed with sat. NaCl and then concentrated. The residue was purified by chromatography (EA/DCM (1:5)) to afford 500 mg (59%) of 6-(2-chloro-6-fluoro-3,5-dimethoxyphenyl)-2-(methylsulfanyl)-7H,8H-pyrido[2,3-d]pyrimidin-7-imine as a yellow solid.

Step 6

To a solution of 6-(2-chloro-6-fluoro-3,5-dimethoxyphenyl)-2-(methylsulfanyl)-7H,8H-pyrido[2,3-d]pyrimidin-7-imine (500 mg, 1.31 mmol) in AcOH (15 mL) was added NaNO$_2$ (450 mg, 6.52 mmol). The resulting solution was stirred for 2 h at 85° C. and then the pH was adjusted to 9 with sat. Na$_2$CO$_3$. The resulting solution was extracted with DCM and the organic layers were combined and concentrated to afford 410 mg (82%) of 6-(2-chloro-6-fluoro-3,5-dimethoxyphenyl)-2-(methylsulfanyl)-7H,8H-pyrido[2,3-d]pyrimidin-7-one as a yellow solid.

Reference 11

Synthesis of Tert-butyl 3-[(2-iodoethyl)(methyl)amino]azetidine-1-carboxylate

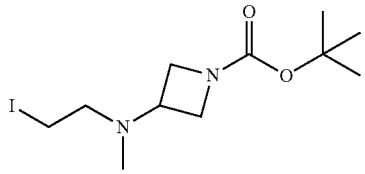

Step 1

To a solution of tert-butyl N-(2-hydroxyethyl)-N-methylcarbamate (2 g, 11.41 mmol) in THF (15 mL) at 0° C. was added NaH (450 mg, 18.75 mmol). The resulting solution was stirred for 2 h at 0° C. and then benzyl bromide (2 g, 11.69 mmo) was added dropwise with stirring at 0° C. The resulting solution was stirred for 4 h at room temperature and then quenched with sat. NH$_4$Cl. The resulting solution was extracted with ethyl acetate and the organic layers were combined, washed with sat. NaCl, dried over Na$_2$SO$_4$, filtered and concentrated. The residue was purified by chromatography (ethyl acetate/petroleum ether (1:10)) to afford 2.2 g (73%) of tert-butyl N-[2-(benzyloxy)ethyl]-N-methylcarbamate as a colorless oil.

Step 2

A solution of tert-butyl N-[2-(benzyloxy)ethyl]-N-methylcarbamate (2 g, 7.54 mmol), TFA (4 mL) and DCM (10 mL) was stirred for 4 h at room temperature and then sat. NaHCO$_3$ was added. The resulting solution was diluted with DCM, washed with sat. NaCl, dried over Na$_2$SO$_4$, filtered and concentrated to afford 1.5 g (crude) of [2-(benzyloxy)ethyl](methyl)amine as a colorless oil.

Step 3

A solution of [2-(benzyloxy)ethyl](methyl)amine (1.5 g, 9.08 mmol) and tert-butyl 3-oxoazetidine-1-carboxylate (1.7 g, 9.93 mmol) in DCM (20 mL) was stirred overnight at rt and then NaBH$_3$CN (800 mg, 12.73 mmol) was added. The resulting solution was stirred for 6 h at room temperature and then water was added. The resulting solution was diluted with DCM, washed with sat. NaCl, dried over Na$_2$SO$_4$, filtered and concentrated. The residue was purified by chromatography (ethyl acetate/petroleum ether (1:20-1:1)) to afford 1 g (34%) of tert-butyl 3-[[2-(benzyloxy)ethyl](methyl)amino]azetidine-1-carboxylate as a brown oil.

Step 4

A mixture of tert-butyl 3-[[2-(benzyloxy)ethyl](methyl)amino]azetidine-1-carboxylate (1.1 g, 1.00 equiv) and Pd on carbon (0.4 g) in MeOH (20 mL) was stirred overnight at room temperature under 1 atm of H$_2$. The solids were then filtered and the solvent was evaporated. The residue was purified by chromatography (DCM/MeOH (25:1)) to afford 0.5 g (63%) of tert-butyl 3-[(2-hydroxyethyl)(methyl)amino]azetidine-1-carboxylate as a light yellow oil.

Step 5

A solution of tert-butyl 3-[(2-hydroxyethyl)(methyl)amino]azetidine-1-carboxylate (310 mg, 1.35 mmol), PPh$_3$ (520 mg, 1.98 mmol), imidazole (135 mg) and I$_2$ (500 mg) in DCM (100 mL) was stirred for 4 h at room temperature. The resulting mixture was then concentrated and the residue was purified by chromatography (DCM/ethyl acetate (20:1)) to afford 430 mg (94%) of tert-butyl 3-[(2-iodoethyl)(methyl)amino]azetidine-1-carboxylate as a light yellow oil.

Reference 12

Synthesis of 6-(2-fluoro-3,5-dimethoxyphenyl)-2-(methylthio)pyrido[2,3-d]pyrimidin-7(8H)-one

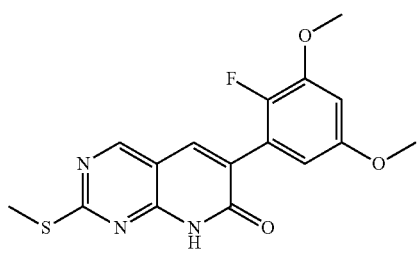

Step 1

To a solution of methyl 2-(3,5-dimethoxyphenyl)acetate (8.5 g, 40.5 mmol) in MeCN (200 mL) at 0° C. was added select-Fluor (20.1 g, 56.7 mmol). The reaction was stirred overnight at 0° C. and then warmed to rt. The reaction was poured into aq. NaHCO$_3$ and extracted with EtOAc. The organic layer was dried over Na$_2$SO$_4$, filtered and concentrated. The residue was purified by chromatography (silica gel, PE:EtOAc=10:1) to afford methyl 2-(2-fluoro-3,5-dimethoxyphenyl)acetate (3.9 g, 42%) as a yellow oil.

Step 2

A mixture of methyl 2-(2-fluoro-3,5-dimethoxyphenyl)acetate (1.8 g, 7.9 mmol), K$_2$CO$_3$ (2.3 g, 16.5 mmol) and 4-amino-2-(methylthio)pyrimidine-5-carbaldehyde (1.1 g, 6.6 mmol) in NMP (30 mL) was stirred overnight at 100° C. The reaction was cooled and then water was added and the mixture was filtered. The filtered cake was washed with EtOAc and dried to afford 6-(2-fluoro-3,5-dimethoxyphenyl)-2-(methylthio)pyrido[2,3-d]pyrimidin-7(8H)-one (650 mg, 28%) as a yellow solid which was converted to the title compounds as described in Reference 4 above. MS (ESI, pos. ion) m/z: 511.2 (M+1).

Reference 13

Synthesis of Tert-butyl 3-[(2-hydroxyethyl)(2-methoxyethyl)-amino]azetidine-1-carboxylate

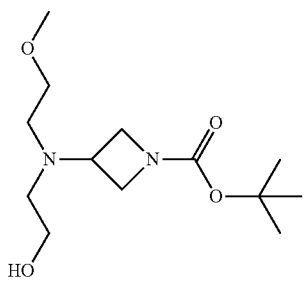

Step 1

A mixture of 2-methoxyethan-1-amine (880 mg, 11.72 mmol), tert-butyl 3-oxoazetidine-1-carboxylate (2 g, 11.68 mmol), AcOH (0.2 mL), Palladium on carbon (2 g) and MeOH (50 mL) was placed under an atmosphere of H$_2$. The resulting solution was stirred overnight at room temperature and then solids were filtered. The filtrate was concentrated and the residue was purified by chromatography (EtOAc/pet. ether (1:1)) to afford 1.29 g (48%) of tert-butyl 3-[(2-methoxyethyl)amino]azetidine-1-carboxylate as a yellow oil.

Step 2

A mixture of tert-butyl 3-[(2-methoxyethyl)amino]azetidine-1-carboxylate (1.19 g, 5.17 mmol), 2-bromoethan-1-ol (770 mg, 6.16 mmol), Na$_2$CO$_3$ (660 mg, 6.23 mmol) and MeCN (50 mL) was stirred overnight at 65° C. The reaction mixture was cooled and the solids were filtered. The resulting filtrate was concentrated and the residue was purified by chromatography (DCM/MeOH (5:1)) to afford 1.1 g (78%) of tert-butyl 3-[(2-hydroxyethyl)(2-methoxyethyl)-amino]azetidine-1-carboxylate as yellow oil.

Reference 14

Synthesis of Tert-butyl 3-[[(2S)-1-hydroxypropan-2-yl](methyl)amino]azetidine-1-carboxylate

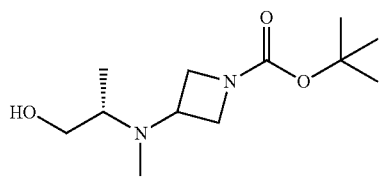

Step 1

A mixture of (2S)-2-(methylamino)propanoic acid (3.6 g, 34.91 mmol), NaBH$_3$CN (3 g, 47.62 mmol), tert-butyl 3-oxoazetidine-1-carboxylate (5 g, 29.21 mmol), MeOH (30 mL) and 4 A M.S. (2 g) was stirred overnight at room temperature. The solids were filtered and the resulting filtrate was concentrated and the residue was purified by chromatography (DCM/EtOAc (10:1)) to afford 3.5 g (39%) of (2S)-2-([1-[(tert-butoxy)carbonyl]azetidin-3-yl](methyl)amino)propanoic acid as a colorless oil.

Step 2

A solution of (2S)-2-([1-[(tert-butoxy)carbonyl]azetidin-3-yl](methyl)amino)propanoic acid (1 g, 3.87 mmol), BH$_3$/THF (7 mL, 1.50 equiv) and THF (10 mL) was stirred for 8 h at room temperature. The reaction mixture was then quenched with water and the resulting solution was diluted with EtOAc. The organic layer was separated and then concentrated. The residue was purified by chromatography (DCM/EtOAc (5:1)) to afford 0.3 g (32%) of tert-butyl 3-[[(2S)-1-hydroxypropan-2-yl](methyl)amino]azetidine-1-carboxylate as a colorless oil.

The title compound was prepared as described in Example 80 starting from Step 5. MS (ESI, pos. ion) m/z: 561.1 (M+1).

Reference 15

Synthesis of Tert-butyl 4-[(2-hydroxyethyl)(methyl)amino]-piperidine-1-carboxylate

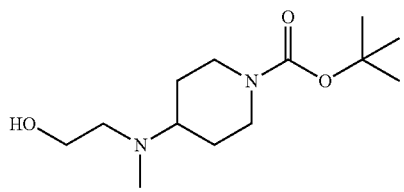

Step 1

A mixture of tert-butyl 4-(methylamino)piperidine-1-carboxylate (6 g, 28.00 mmol), K$_2$CO$_3$ (11.61 g, 84.00 mmol) and methyl 2-bromoacetate (4.69 g, 30.66 mmol) in acetone (100 mL) was stirred at 0° C. in a water/ice bath and then the resulting solution was stirred overnight at room temperature. The solids were filtered and the filtrate was concentrated. The residue was purified by chromatography (DCM/EtOAc (10:1)) to afford 7.4 g (92%) of tert-butyl 4-[(2-methoxy-2-oxoethyl)(methyl)amino]piperidine-1-carboxylate as a yellow oil.

Step 2

To a solution of tert-butyl 4-[(2-methoxy-2-oxoethyl)(methyl)amino]piperidine-1-carboxylate (5.94 g, 20.74 mmol) in THF (100 mL) at 0° C. was added LiAlH$_4$ (630 mg, 16.60 mmol). The resulting solution was stirred for 1 h at room temperature and then H$_2$O/NaOH(15%)/H$_2$O(0.6 ml/0.6 ml/1.8 ml) was added. The solids were filtered and the filtrate was concentrated to afford 4.64 g (87%) of tert-butyl 4-[(2-hydroxyethyl)(methyl)amino]-piperidine-1-carboxylate as a yellow oil.

Example 1

Synthesis of N-(4-(2-(6-(2-chlorophenyl)-2-(4-(diethylamino)butylamino)-7-oxopyrido[2,3-d]pyrimidin-8 (7H)-yl)ethyl)phenyl)-2-cyano-4-methylpent-2-enamide

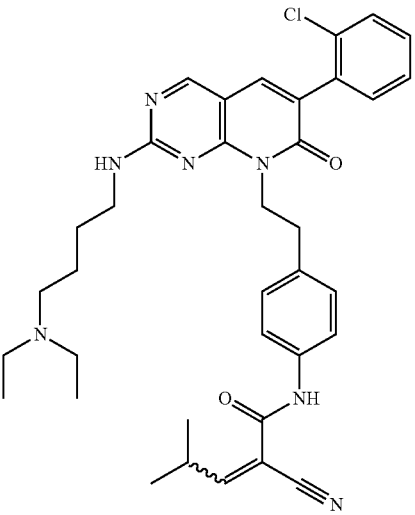

Step 1

Into a 100-mL 3-necked round-bottom flask, was placed 6-(2-chlorophenyl)-2-(methyl-sulfanyl)-7H,8H-pyrido[2,3-d]pyrimidin-7-one (3.03 g, 9.97 mmol, 1.00 equiv), tert-butyl N-[4-(2-hydroxyethyl)phenyl]carbamate (2.61 g, 10.99 mmol, 1.10 equiv), PPh$_3$ (5.24 g, 19.98 mmol, 2.00 equiv) and N,N-dimethylformamide (30 mL). After the mixture was stirred for 3 min, DIAD (4.04 g, 19.98 mmol, 2.00 equiv) was dropped into the solution with stirring at 0° C. under N$_2$. The resulting solution was stirred for 4 h at 0° C. and then diluted with H$_2$O. The resulting solution was extracted with ethyl acetate and the organic layers were combined and washed with water. The organic layer was dried over anhydrous sodium sulfate, filtered and concentrated. The resulting residue was purified by silica gel column with ethyl acetate/petroleum ether (1:10-1:5) to give 3.15 g (yield 60%) of tert-butylN-(4-[2-[6-(2-chlorophenyl)-2-(methylsulfanyl)-7-oxo-7H,8H-pyrido[2,3-d]pyrimidin-8-yl]ethyl]-phenyl)carbamate as an off-white solid.

Step 2

Into a 500-mL round-bottom flask, was placed tert-butyl N-(4-[2-[6-(2-chlorophenyl)-2-(methylsulfanyl)-7-oxo-7H,8H-pyrido[2,3-d]pyrimidin-8-yl]ethyl]phenyl)carbamate (2.85 g, 5.45 mmol, 1.00 equiv), chloroform (150 mL) and m-CPBA (85%, 2.82 g, 3.00 equiv). The resulting solution was stirred for 3 h at room temperature and then diluted with DCM. The resulting mixture was washed with saturated potassium carbonate solution and then brine. The mixture was dried over anhydrous sodium sulfate, filtered and then concentrated under vacuum to give 3.40 g (crude) of tert-butyl N-(4-[2-[6-(2-chlorophenyl)-2-methanesulfonyl-7-oxo-7H,8H-pyrido[2,3-d]-pyrimidin-8-yl]ethyl]phenyl)carbamate as a light brown solid.

Step 3

Into a 250-mL round-bottom flask, was placed tert-butyl N-(4-[2-[6-(2-chlorophenyl)-2-methanesulfonyl-7-oxo-7H,8H-pyrido[2,3-d]pyrimidin-8-yl]ethyl]phenyl)carbamate (3.20 g, 5.77 mmol, 1.00 equiv), (4-aminobutyl)diethylamine (1.67 g, 11.58 mmol, 2.00 equiv) and pyridine (40 mL). The resulting solution was stirred for 2 h at 80° C. and then concentrated under vacuum. The residue was purified by silica gel column with methanol:ethyl acetate (EA-1:30-1:20) to give 2.80 g (crude) of tert-butyl N-(4-[2-[6-(2-chlorophenyl)-2-[[4-(diethylamino)butyl]amino]-7-oxo-7H,8H-pyrido[2,3-d]pyrimidin-8-yl]ethyl]phenyl)-carbamate as a brown solid.

Step 4

Into a 250-mL round-bottom flask, was placed tert-butyl N-(4-[2-[6-(2-chlorophenyl)-2-[[4-(diethylamino)butyl]amino]-7-oxo-7H,8H-pyrido[2,3-d]pyrimidin-8-yl]ethyl]phenyl)-carbamate (1.00 g, 1.61 mmol, 1.00 equiv), dichloromethane (30 mL) and trifluoroacetic acid (8 mL). The resulting solution was stirred for 2 h at room temperature and then concentrated under vacuum. The residue was diluted with dichloromethane and washed with saturated potassium carbonate solution. The organic layer was dried over anhydrous sodium sulfate, filtered and then concentrated under vacuum to give 803 mg (96%) of 8-[2-(4-aminophenyl)ethyl]-6-(2-chlorophenyl)-2-[[4-(diethylamino)butyl]amino]-7H,8H-pyrido[2,3-d]pyrimidin-7-one as a brown solid.

Step 5

A solution of 8-(4-aminophenethyl)-6-(2-chlorophenyl)-2-(4-(diethylamino)butylamino)-pyrido[2,3-d]pyrimidin-7(8H)-one (1.25 g crude, 2.5 mmol, 1.0 equiv), 2-cyanoacetic acid (0.32 g, 3.75 mmol, 1.5 equiv), HATU (1.425 g, 3.75 mmol, 1.5 equiv) and Et$_3$N (1.262 g, 12.5 mmol, 5 equiv) in DMF (20 mL) was stirred at rt overnight. The mixture was poured into water and extracted with ethyl acetate. The organic layer was washed with brine, dried over anhydrous sodium sulfate, filtered and concentrated under vacuum to give 1.1 g (crude) of N-(4-(2-(6-(2-chlorophenyl)-2-(4-(diethylamino)butylamino)-7-oxopyrido[2,3-d]pyrimidin-8 (7H)-yl)ethyl) phenyl)-2-cyanoacetamide as a brown oil.

Step 6

A solution of N-(4-(2-(6-(2-chlorophenyl)-2-(4-(diethylamino)butylamino)-7-oxopyrido-[2, 3-d]pyrimidin-8 (7H)-yl)ethyl)phenyl)-2-cyanoacetamide (380 mg, 0.68 mmol, 1.0 equiv), isobutyraldehyde (246 mg, 7.41 mmol, 5.0 equiv) and piperidine (116 mg, 1.36 mmol, 2.0 equiv) in DCM/MeOH (10 mL/10 mL) was stirred at rt overnight. The mixture was concentrated and the crude product was purified by prep-HPLC with the following conditions (1#-Pre-HPLC-005(Waters)): Column, SunFire Prep C18 19*150 mm Sum; mobile phase, water with 0.05% trifluoroacetic acid and CH$_3$CN (10% CH$_3$CN up to 30% in 10 min); Detector, 254 nm. The resulting solution was diluted with sat.Na$_2$CO$_3$ solution and extracted with DCM. The organic layer was washed with brine, dried over anhydrous sodium sulfate, filtered and concentrated under vacuum to give 48.2 mg (12%) of N-(4-(2-(6-(2-chlorophenyl)-2-(4-(diethylamino)butylamino)-7-oxopyrido[2,3-d]pyrimidin-8 (7H)-yl)ethyl) phenyl)-2-cyano-4-methylpent-2-enamide as a white solid. LCMS (ESI, pos. ion) m/z: 640 (M+1).

Example 2

Synthesis of 2-(3-(2-(6-(2-chlorophenyl)-2-(4-(diethylamino)butylamino)-7-oxopyrido[2,3-d]pyrimidin-8(7H)-yl)ethyl)piperidine-1-carbonyl)-4-methylpent-2-enenitrile

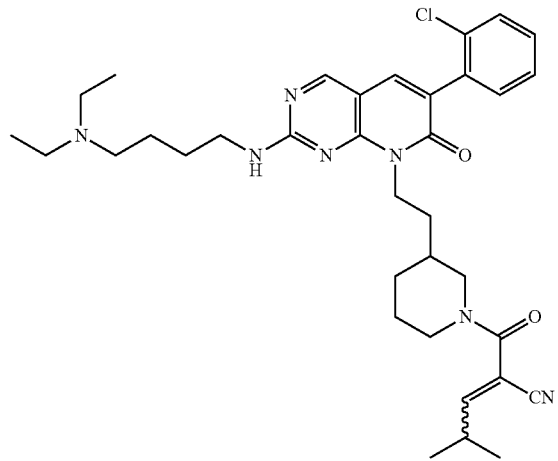

Step 1

To a mixture of 6-(2-chlorophenyl)-2-(methylthio)pyrido[2,3-d]pyrimidin-7(8H)-one (3.03 g, 10 mmol, 1.0 equiv), tert-butyl 3-(2-hydroxyethyl)piperidine-1-carboxylate (2.52 g, 11 mmol, 1.1 equiv) and PPh$_3$ (5.24 g, 20 mmol, 2.0 equiv) in DMF (30 mL) at 0° C. under N$_2$ was added DIAD (4.04 g, 20 mmol, 2.0 equiv) dropwise. The mixture was stirred at rt overnight and then poured into water and extracted with ethyl acetate. The organic layer was washed with water, dried over anhydrous sodium sulfate, filtered and concentrated under vacuum. The residue was purified by column chromatography using petroleum ether/ethyl acetate (10/1 to 3/1) to give 5.15 g (60%) of tert-butyl 3-(2-(6-(2-chlorophenyl)-2-(methylthio)-7-oxopyrido[2,3-d]pyrimidin-8(7H)-yl)ethyl)piperidine-1-carboxylate as a white solid.

Step 2

To a mixture of tert-butyl 3-(2-(6-(2-chlorophenyl)-2-(methylthio)-7-oxopyrido[2,3-d]-pyrimidin-8(7H)-yl)ethyl) piperidine-1-carboxylate (3.09 g, 6 mmol, 1 equiv) in CHCl$_3$ (150 mL) was slowly added mCPBA (85%, 3.65 g, 18 mmol, 3.0 equiv). The reaction was stirred at rt overnight and then washed with a sat. NaHCO$_3$ solution and brine, then dried over anhydrous sodium sulfate, filtered and concentrated under vacuum to give 4.1 g (crude) of tert-butyl 3-(2-(6-(2-chlorophenyl)-2-(methylsulfonyl)-7-oxopyrido[2,3-d]pyrimidin-8(7H)-yl)ethyl)piperidine-1-carboxylate as a brown oil.

Step 3

A solution of tert-butyl 3-(2-(6-(2-chlorophenyl)-2-(methylsulfonyl)-7-oxopyrido[2,3-d]-pyrimidin-8(7H)-yl) ethyl)piperidine-1-carboxylate (3.27 g, 6 mmol, 1.0 equiv) and N$^1$,N$^1$-diethylbutane-1,4-diamine (2.6 g, 18 mmol, 3.0 equiv) in pyridine (20 mL) was heated to 80° C. for 2 hours. The mixture was poured into water and extracted with ethyl acetate. The organic layer was washed with brine, dried over anhydrous sodium sulfate, filtered and concentrated under vacuum. The residue was purified by column chromatography using ethyl acetate/methanol (30/1 to 5/1) to give 2.2 g (60%) of tert-butyl 3-(2-(6-(2-chlorophenyl)-2-(4-(diethylamino)butylamino)-7-oxopyrido[2,3-d]pyrimidin-8(7H)-yl) ethyl)piperidine-1-carboxylate as a brown solid.

Step 4

To a mixture of tert-butyl 3-(2-(6-(2-chlorophenyl)-2-(4-(diethylamino)butylamino)-7-oxopyrido[2,3-d]pyrimidin-8

(7H)-yl)ethyl)piperidine-1-carboxylate (0.8 g, 1.3 mmol, 1.0 equiv) in DCM (8 mL) was added TFA (2 mL). The reaction was stirred overnight at rt and then concentrated. To the residue was added a sat. Na₂CO₃ solution and then extracted with ethyl acetate. The organic layer was washed with brine, dried over anhydrous sodium sulfate, filtered and concentrated under vacuum to give 0.62 g (93%) of 6-(2-chlorophenyl)-2-(4-(diethylamino)-butylamino)-8-(2-(piperidin-3-yl)ethyl)pyrido[2,3-d]pyrimidin-7(8H)-one as a brown solid.

Step 5

To a solution of 6-(2-chlorophenyl)-2-(4-(diethylamino)butylamino)-8-(2-(piperidin-3-yl)-ethyl)pyrido[2,3-d]pyrimidin-7(8H)-one (511 mg, 1 mmol, 1.0 eq) in DMF (20 mL) at room temperature was added 2-cyanoacetic acid (128 mg, 1.5 mmol, 1.5 eq), HATU (570 mg, 1.5 mmol, 1.5 eq), and Et₃N (505 mg, 5 mmol, 5 eq). The reaction was stirred overnight at room temperature and then quenched with H₂O and extracted with ethyl acetate. The organic layer was washed with brine, dried over Na₂SO₄, filtered concentrated. The residue was purified by silica gel column (ethyl acetate/methanol=20/1) to give 480 mg (83%) of 3-(3-(2-(2-(4-(diethylamino)-butylamino)-6-(2-chlorophenyl)-7-oxopyrido[2,3-d]pyrimidin-8(7H)-yl)ethyl)piperidin-1-yl)-3-oxopropanenitrile as a yellow solid.

Step 6

To a solution of 3-(3-(2-(2-(4-(diethylamino)butylamino)-6-(2-chlorophenyl)-7-oxo-pyrido[2,3-d]pyrimidin-8(7H)-yl)ethyl)piperidin-1-yl)-3-oxopropanenitrile (193 mg, 0.33 mmol, 1 eq) in EtOH at room temperature (15 mL) was added isobutyraldehyde (120 mg, 1.67 mmol, 5 eq) and piperidine (56 mg, 0.66 mmol, 2 eq). The reaction was stirred for 2 h at room temperature and then concentrated. The crude product was purified by prep-HPLC with the following conditions (IntelFlash-1): Column, C18 silica gel; mobile phase, CH₃CN/H₂O (0.05% TFA)=5/100 increasing to CH₃CN/H₂O (0.05% TFA)=20/100 within 30 min; Detector, UV 254 nm. After removing solvent, the pH of the aqueous phase was adjusted to 9, and then it was extracted with DCM (50 ml×3). The organic layers were combined, washed with brine, dried over sodium sulfate, filtrate and concentrated to give 20.0 mg (9.6%) of 2-(3-(2-(6-(2-chlorophenyl)-2-(4-(diethylamino)butylamino)-7-oxopyrido[2,3-d]pyrimidin-8(7H)-yl)ethyl)piperidine-1-carbonyl)-4-methylpent-2-enenitrile as a white solid. LCMS (ESI, pos. ion) m/z: 632 (M+1).

Example 3

Synthesis of N-(3-[2-[6-(2-chlorophenyl)-2-[[4-(diethylamino)butyl]amino]-7-oxo-7H,8H-pyrido[2,3-d]pyrimidin-8-yl]ethyl]phenyl)-2-cyano-4-methylpent-2-enamide

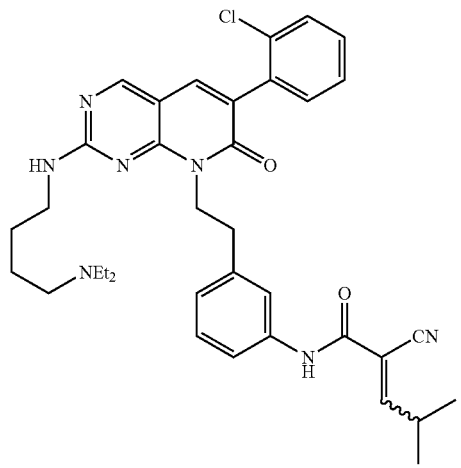

Proceeding as described in Example 1 above but substituting tert-butyl N-[4-(2-hydroxyethyl)phenyl]carbamate with tert-butyl N-[3-(2-hydroxyethyl)phenyl]carbamate and proceeding as described affords N-(3-[2-[6-(2-chlorophenyl)-2-[[4-(diethylamino)butyl]amino]-7-oxo-7H,8H-pyrido[2,3-d]pyrimidin-8-yl]ethyl]phenyl)-2-cyano-4-methylpent-2-enamide. (ES, m/z): [M+H]⁺640.

Example 4

Synthesis of 2-cyano-N-(4-(2-(6-(2,6-dichloro-3,5-dimethoxyphenyl)-2-(4-(diethylamino)-butylamino)-7-oxopyrido[2,3-d]pyrimidin-8(7H)-yl)ethyl)phenyl)-4-methylpent-2-enamide formate

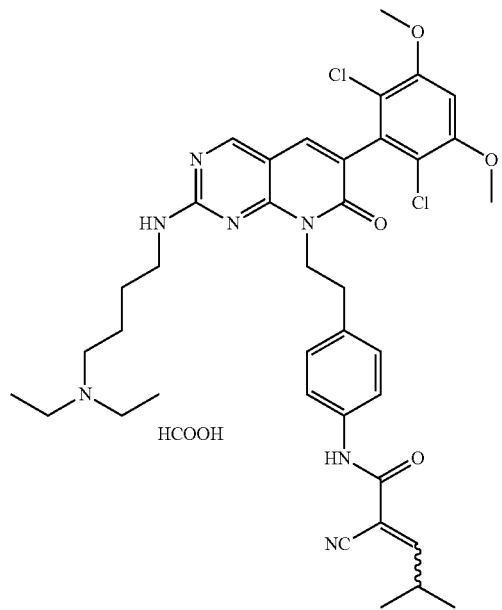

Step 1
Step 1

Into a 250-mL round-bottom flask, was placed a solution of 6-(2,6-dichloro-3,5-dimethoxyphenyl)-2-(methylsulfanyl)-7H,8H-pyrido[2,3-d]pyrimidin-7-one (1.5 g, 3.77 mmol, 1.00 equiv) in acetone (100 mL). Potassium carbonate (3.123 g, 22.43 mmol, 6.00 equiv), and tert-butyl N-[4-(2-iodoethyl)phenyl]carbamate (1.962 g, 5.65 mmol, 1.50 equiv) were added to the reaction mixture. The resulting solution was heated to reflux overnight, and then it was concentrated under vacuum. The reaction was then quenched with water. The resulting solution was extracted with ethyl acetate, and the combined organic layers were concentrated under vacuum. The residue was applied onto a silica gel column with ethyl acetate/petroleum ether (1:2) as eluent. The collected fractions were combined and concentrated under vacuum to yield 1.7 g (73%) of tert-butyl N-(4-[2-[6-(2,6-dichloro-3,5-dimethoxyphenyl)-2-(methylsulfanyl)-7-oxo-7H,8H-pyrido[2,3-d]pyrimidin-8-yl]ethyl]phenyl)carbamate as a yellow solid.

Step 2

Into a 500-mL round-bottom flask, was placed a solution of tert-butyl N-(4-[2-[6-(2,6-dichloro-3,5-dimethoxyphenyl)-2-(methylsulfanyl)-7-oxo-7H,8H-pyrido[2,3-d]pyrimidin-8-yl]ethyl]phenyl)carbamate (1.7 g, 2.75 mmol, 1.00 equiv) in chloroform (200 mL). 3-Chlorobenzene-1-carboperoxoic acid (1.187 g, 6.88 mmol, 2.50 equiv) was added to the reaction mixture. The resulting solution was stirred overnight at room temperature. The pH value of the solution was adjusted to 8 with sodium bicarbonate solution (sat.). The resulting solution was extracted with dichloromethane, and the combined organic layers were washed with brine, and concentrated under vacuum. The residue was applied onto a silica gel column with ethyl acetate/petroleum ether (1:1) as eluent. The collected fractions were combined and concentrated under vacuum to yield 1.49 g (83%) of tert-butyl N-(4-[2-[6-(2,6-dichloro-3,5-dimethoxyphenyl)-2-methanesulfonyl-7-oxo-7H,8H-pyrido[2,3-d]pyrimidin-8-yl]ethyl]-phenyl)carbamate as a light yellow solid.
Step 3

Into a 100-mL round-bottom flask, was placed a solution of tert-butyl N-(4-[2-[6-(2,6-dichloro-3,5-dimethoxyphenyl)-2-methanesulfonyl-7-oxo-7H,8H-pyrido[2,3-d]pyrimidin-8-yl]-ethyl]phenyl)carbamate (1.02 g, 1.57 mmol, 1.00 equiv) in DMSO (30 mL). TEA (477 mg, 4.71 mmol, 3.00 equiv) and (4-aminobutyl)diethylamine (340 mg, 2.36 mmol, 1.50 equiv) were added to the reaction mixture. The resulting solution was stirred for 4 h at 50° C., and then it was diluted with water. The resulting solution was extracted with ethyl acetate, and the combined organic layers were washed with brine and concentrated under vacuum. This resulted in 1.1 g (98%) of tert-butyl N-(4-[2-[6-(2,6-dichloro-3,5-dimethoxy-phenyl)-2-[[4-(diethylamino)butyl]amino]-7-oxo-7H,8H-pyrido[2,3-d]pyrimidin-8-yl]ethyl]-phenyl)carbamate as a brown solid.
Step 4

Into a 50-mL round-bottom flask, was placed a solution of tert-butyl N-(4-[2-[6-(2,6-dichloro-3,5-dimethoxyphenyl)-2-[[4-(diethylamino)butyl]amino]-7-oxo-7H,8H-pyrido[2,3-d]-pyrimidin-8-yl]ethyl]phenyl)carbamate (1.1 g, 1.54 mmol, 1.00 equiv) in dichloromethane (10 mL) and trifluoroacetic acid (5 mL). The resulting solution was stirred overnight at room temperature, and then it was concentrated under vacuum. The pH value of the solution was adjusted to 8 with sodium bicarbonate (sat.). The resulting solution was extracted with DCM/MeOH (10:1) and the combined organic layers were concentrated under vacuum. This resulted in 890 mg (94%) of 8-[2-(4-aminophenyl)ethyl]-6-(2,6-dichloro-3,5-dimethoxyphenyl)-2-[[4-(diethylamino)butyl]amino]-7H,8H-pyrido[2,3-d]pyrimidin-7-one as a brown solid.
Step 5

Into a 25-mL round-bottom flask, was placed a solution of 8-[2-(4-aminophenyl)ethyl]-6-(2,6-dichloro-3,5-dimethoxyphenyl)-2-[[4-(diethylamino)butyl]amino]-7H,8H-pyrido[2,3-d]-pyrimidin-7-one (300 mg, 0.49 mmol, 1.00 equiv) in N,N-dimethylformamide (7 mL). 2-Cyano-4-methylpent-2-enoic acid (74.8 mg, 0.54 mmol, 1.10 equiv), HATU (278.9 mg, 0.73 mmol, 3.00 equiv), and TEA (148.4 mg, 1.47 mmol, 3.00 equiv) were added to the reaction mixture. The resulting solution was stirred overnight at room temperature, and then it was diluted with water. The resulting solution was extracted with DCM/MeOH(10:1) and the organic layers combined, and concentrated under vacuum. The crude product (300 mg) was purified by Prep-HPLC with the following conditions (2#-AnalyseHPLC-SHIMADZU (HPLC-10)): Column, SunFire Prep C18 OBD Column, 5 um, 19*150 mm; mobile phase, water with 0.1% HCOOH and MeCN (22.0% MeCN up to 36.0% in 10 min, up to 100.0% in 2 min, down to 22.0% in 1 min); Detector, Waters2545 UvDector 254&220 nm. This resulted in 37 mg (10%) of 2-cyano-N-(4-[2-[6-(2,6-dichloro-3,5-dimethoxyphenyl)-2-[[4-(diethylamino)butyl]amino]-7-oxo-7H,8H-pyrido[2,3-d]pyrimidin-8-yl]ethyl]phenyl)-4-methylpent-2-enamide; formic acid as a gray solid. LC-MS m/z: 736 [M+1-HCOOH]+.

Example 5

Synthesis of 2-cyano-N-(3-[[3-(2,6-dichloro-3,5-dimethoxyphenyl)-2-[[4-(diethylamino)butyl]-amino]-7-oxo-7H,8H-pyrido[2,3-d]pyrimidin-8-yl]thyl]phenyl)-4-methylpent-2-enamide

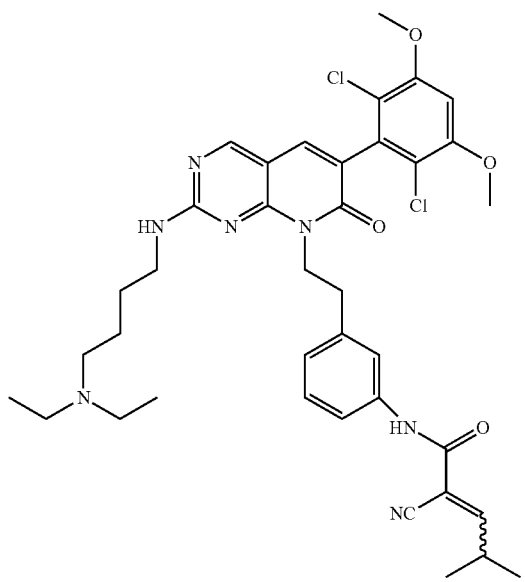

Step 1

Into a 250-mL round-bottom flask, was placed a solution of (3-aminophenyl)methanol (5 g, 40.60 mmol, 1.00 equiv) and di-tert-butyl dicarbonate (9.60 g, 43.99 mmol, 1.08 equiv) in tetrahydrofuran (150 mL). The resulting solution was stirred overnight at room temperature. The resulting mixture was concentrated under vacuum. The residue was applied onto a silica gel column with ethyl acetate/petroleum ether (1:10) to yield 8.92 g (98%) of tert-butyl N-[3-(hydroxymethyl)phenyl]carbamate as a white solid.
Step 2

Into a 250-mL round-bottom flask, was placed a solution of tert-butyl N-[3-(hydroxy-methyl)phenyl]carbamate (4.46 g, 19.98 mmol, 1.00 equiv) in dichloromethane (150 mL). Triphenylphosphine (6.70 g, 25.54 mmol, 1.28 equiv), 1H-imidazole (2.244 g, 32.96 mmol, 1.65 equiv), and iodine (6.10 g, 24.03 mmol, 1.20 equiv) were added to the reaction mixture. The resulting solution was stirred for 1.5 h at room temperature, and then it was quenched by the addition of water. The resulting solution was extracted with dichloromethane, and the combined organic layers were dried over anhydrous sodium sulfate and concentrated under vacuum. The residue was applied onto a silica gel column with ethyl acetate/petroleum ether (1:50) as eluent. This resulted in 4.7 g (71%) of tert-butyl N-[3-(iodomethyl)phenyl]carbamate as a white solid.
Step 3 tert-Butyl N-[3-(iodomethyl)-phenyl]carbamate was reacted with 6-(2,6-dichloro-3,5-dimethoxyphenyl)-2-(methylsulfanyl)-7H,8H-pyrido[2,3-d]pyrimidin-7-one to provide tert-butyl N-(3-[[6-(2,6-dichloro-3,5-dimethoxyphenyl)-2-(methylsulfanyl)-7-oxo-7H,8H-pyrido[2,3-d]pyrimidin-8-yl]methyl]phenyl)carbamate and converted to the title compound as described in Example 4 above as a light yellow solid. LC-MS (m/z): 720.3 [M+1].

Example 6

Synthesis of 2-cyano-N-(3-(2-(6-(2,6-dichloro-3,5-dimethoxyphenyl)-2-(4-(ethyl(methyl)amino)-butylamino)-7-oxopyrido[2,3-d]pyrimidin-8(7H)-yl)ethyl)phenyl)-4-methylpent-2-enamide Hydrochloride

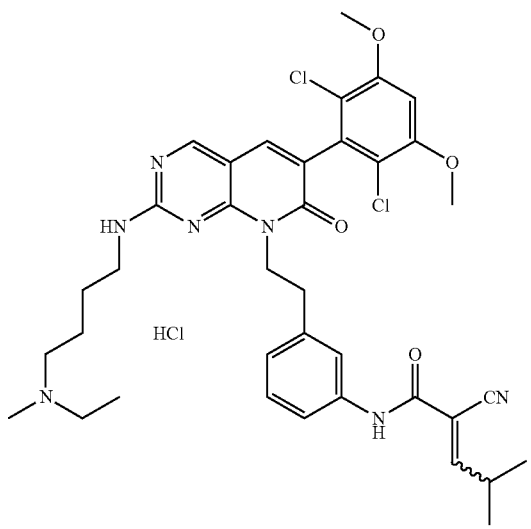

Step 1
Into a 50-mL round-bottom flask, was placed a mixture of 2-(3-nitrophenyl)acetonitrile (4 g, 24.67 mmol, 1.00 equiv), water (8 mL), sulfuric acid (8 mL), and acetic acid (8 mL). The resulting solution was stirred overnight at 110° C., and then it was diluted with water. The resulting solution was extracted with ethyl acetate, and the combined organic layers were concentrated under vacuum to yield 4.2 g (94%) of 2-(3-nitrophenyl)acetic acid as a yellow solid.
Step 2
Into a 500-mL three neck round-bottom flask, was placed a solution of 2-(3-nitrophenyl)-acetic acid (2 g, 11.04 mmol, 1.00 equiv) in tetrahydrofuran (150 mL). This was followed by the addition of BH$_3$.SMe$_2$ (10M, 1.2 mL, 12.15 mmol, 1.10 equiv) drop wise with stirring, while the temperature was maintained at reflux over 10 min. The resulting solution was heated to reflux overnight. The pH value of the solution was adjusted to 8 with sodium bicarbonate (aq). The resulting solution was extracted with DCM/MeOH (10:1) and the combined organic layers were concentrated under vacuum. The residue was applied onto a silica gel column with ethyl acetate/petroleum ether (1:2) as eluent to yield 1.1 g (60%) of 2-(3-nitrophenyl)ethan-1-ol as a brown oil.
Step 3
Into a 250-mL round-bottom flask, was placed a solution of 2-(3-nitrophenyl)ethan-1-ol (1.1 g, 6.58 mmol, 1.00 equiv) in ethanol (100 mL). 10% Palladium on carbon (500 mg) was added to the reaction mixture. The resulting solution was stirred overnight at room temperature under hydrogen atmosphere. The solids were filtered out. The filtrate was concentrated under vacuum to yield 800 mg (89%) of 2-(3-aminophenyl)ethan-1-ol as a brown oil.
Step 4
Into a 100-mL round-bottom flask, was placed a solution of 2-(3-aminophenyl)ethan-1-ol (800 mg, 5.83 mmol, 1.00 equiv) in a solvent mixture of water (15 mL) and 1,4-dioxane (30 mL). Sodium hydroxide (240 mg, 6.00 mmol, 1.00 equiv) and di-tert-butyl dicarbonate (1.4 g, 6.41 mmol, 1.10 equiv) were added to the reaction mixture. The resulting solution was stirred overnight at room temperature, and then it was diluted with water. The resulting solution was extracted with ethyl acetate and the combined organic layers were concentrated under vacuum. The residue was applied onto a silica gel column with ethyl acetate/petroleum ether (1:3) as eluent to yield 1.1 g (79%) of tert-butyl N-[3-(2-hydroxyethyl)phenyl]carbamate as a light yellow solid.
Step 5
Into a 100-mL round-bottom flask, was placed a solution of tert-butyl N-[3-(2-hydroxyethyl)phenyl]carbamate (1.1 g, 4.64 mmol, 1.00 equiv) in dichloromethane (40 mL). Imidazole (0.505 g), I$_2$ (1.412 g, 5.56 mmol, 1.20 equiv), and triphenylphosphane (1.459 g, 5.56 mmol, 1.20 equiv) were added to the reaction solution. The resulting solution was stirred overnight at room temperature, and then it was diluted with water. The resulting solution was extracted with dichloromethane and the combined organic layers were applied onto a silica gel column with ethyl acetate/petroleum ether (1:20) as eluent to yield 1.48 g (92%) of tert-butyl N-[3-(2-iodoethyl)phenyl]carbamate as a white solid. The title compound was prepared as described in Example 5 above but substituting (4-aminobutyl)diethylamine with N1-ethyl-N1-methylbutane-1,4-diamine and [3-(2-iodoethyl)phenyl]carbamate instead of tert-butyl-N-[3-(2-iodomethyl)-phenyl]carbamate. LC-MS m/z: 734.5 [M+1]$^+$.

Example 7

Synthesis of 2-cyano-N-(3-(2-(6-(2,6-dichloro-3,5-dimethoxyphenyl)-2-(methylamino)-7-oxopyrido[2,3-d]pyrimidin-8(7H)-yl)ethyl)phenyl)-4-methylpent-2-enamide

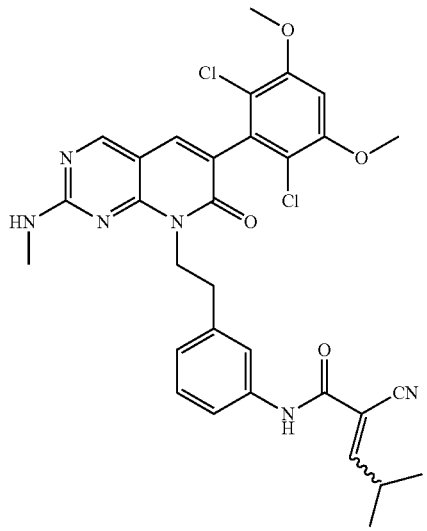

Into a 50-mL round-bottom flask, was placed a solution of tert-butyl N-(3-[2-[6-(2,6-dichloro-3,5-dimethoxyphenyl)-2-methanesulfonyl-7-oxo-7H,8H-pyrido[2,3-d]pyrimidin-8-yl]-ethyl]phenyl)carbamate (85.5 mg, 0.13 mmol, 1.00 equiv) in DMSO (5 mL). TEA (60.1 mg, 0.59 mmol, 5.00 equiv) and methanamine hydrochloride (13.4 mg, 0.20 mmol, 1.50 equiv) were added to the reaction mixture. The resulting solution was stirred for 12 h at 50° C., and then it was quenched with water. The resulting solution was extracted with dichloromethane and the combined organic layers were dried over anhydrous sodium sulfate and concentrated under vacuum. This resulted in 75 mg (95%) of tert-butyl N-(3-[2-[6-(2,6-dichloro-3,5-dimethoxy-phenyl)-2-(methylamino)-7-oxo-7H,8H-pyrido[2,3-d]pyrimidin-8-yl]ethyl]phenyl)carbamate as a yellow solid which was converted to the title compound as described in Example 4 above. LC-MS m/z: 623.3 [M+1]⁺.

Example 8

Synthesis of 2-(4-(2-(6-(2-chloro-3,5-dimethoxyphenyl)-2-(methylamino)-7-oxopyrido[2,3-d]pyrimidin-8(7H)-yl)ethyl)piperazine-1-carbonyl)-4,4-dimethylpent-2-enenitrile

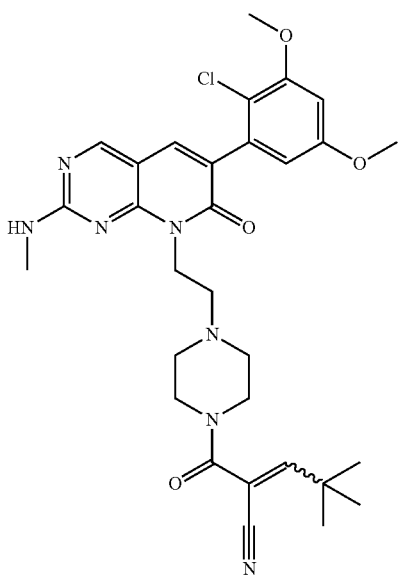

Step 1

To a solution of tert-butyl 4-(2-hydroxyethyl)piperazine-1-carboxylate (2.30 g, 10 mmol) in dichloromethane (100 mL) was added DIPEA (2.58 g, 20 mmol) and MSCl (1.72 g, 15 mmol) at 0° dropwise, the mixture was stirred at ambient temperature for 1 h before quenching with water (50 mL). The mixture was extracted with dichloromethane, washed with brine and the organic layer was dried over anhydrous sodium sulfate, filtered, and evaporated under vacuum to get tert-butyl 4-(2-((methylsulfonyl)oxy)ethyl)piperazine-1-carboxylate as a colorless oil (3.08 g) which was used without further purification.

Step 2

To a solution of 6-(2-chloro-3,5-dimethoxyphenyl)-2-(methylthio)pyrido[2,3-d]pyrimidin-7(8H)-one (1.5 g, 4.3 mmol) in DMF (10 mL) was added potassium carbonate (1.79 g, 13 mmol). Then tert-butyl 4-(2-((methylsulfonyl)oxy)-ethyl)piperazine-1-carboxylate (2 g, 6.5 mmol) was added and the mixture was stirred at 75° C. for 1 h. The mixture was poured into water (50 mL), extracted with ethyl acetate, washed with brine, and the organic layer was dried over anhydrous sodium sulfate, filtered, evaporated under vacuum to get tert-butyl 4-(2-(6-(2-chloro-3,5-dimethoxyphenyl)-2-(methylthio)-7-oxopyrido[2,3-d]pyrimidin-8(7H)-yl)ethyl)piperazine-1-carboxylate as a white solid (2.5 g) which was used without further purification.

Step 3

To a solution of tert-butyl 4-(2-(6-(2-chloro-3,5-dimethoxyphenyl)-2-(methylthio)-7-oxopyrido[2,3-d]pyrimidin-8(7H)-yl)ethyl)piperazine-1-carboxylate (2.30 g, 4.3 mmol) in dichloromethane (30 mL) was added m-CPBA (1.50 g, 8.6 mmol), and the resulting mixture was stirred at ambient temperature for 1 h before diluting with dichloromethane (60 mL). The mixture was washed with sat. sodium bicarbonate aqueous solution (50 mL), the organic layer was dried over anhydrous sodium sulfate, filtered, evaporated under vacuum to get tert-butyl 4-(2-(6-(2-chloro-3,5-dimethoxyphenyl)-2-(methylsulfinyl)-7-oxopyrido[2,3-d]pyrimidin-8(7H)-yl)ethyl)piperazine-1-carboxylate as a white solid (2.50 g) which was used for the next step without additional purification.

Step 4

To a solution of tert-butyl 4-(2-(6-(2-chloro-3,5-dimethoxyphenyl)-2-(methylsulfinyl)-7-oxopyrido[2,3-d]pyrimidin-8(7H)-yl)ethyl)piperazine-1-carboxylate (2.50 g, 4.3 mmol) in DMSO (10 mL) was added DIPEA (1.66 g, 17.2 mmol), methylamine hydrochloride (0.58 g, 8.6 mmol), the mixture was stirred at 85° C. for 1 h. The mixture was poured into water, extracted with ethyl acetate and washed with brine. The organic layer was dried over anhydrous sodium sulfate, filtered, evaporated under vacuum to obtain tert-butyl 4-(2-(6-(2-chloro-3,5-dimethoxyphenyl)-2-(methylamino)-7-oxopyrido[2,3-d]pyrimidin-8(7H)-yl)ethyl)piperazine-1-carboxylate as a yellow oil (2.40 g) which was used in the next step without further purification.

Step 5

To a solution of tert-butyl 4-(2-(6-(2-chloro-3,5-dimethoxyphenyl)-2-(methylamino)-7-oxopyrido[2,3-d]pyrimidin-8(7H)-yl)ethyl)piperazine-1-carboxylate (2.4 g, 4.3 mmol) in dichloromethane (10 mL) was added TFA (4 mL) and the mixture was stirred at ambient temperature overnight before evaporating under vacuum. The residue was diluted with dichloromethane (200 mL) and isopropanol (100 mL), and the resultant organic phase washed with sat. sodium bicarbonate aqueous solution. The organic layer was dried over anhydrous sodium sulfate, filtered, evaporated under vacuum to get 6-(2-chloro-3,5-dimethoxyphenyl)-2-(methylamino)-8-(2-(piperazin-1-yl)ethyl)pyrido[2,3-d]pyrimidin-7(8H)-one as a gray solid (1.2 g, 70%) after purification by flash chromatography (silica gel, dichloromethane/methanol/ammonium hydroxide=200:10:1).

Step 6

To a solution of 6-(2-chloro-3,5-dimethoxyphenyl)-2-(methylamino)-8-(2-(piperazin-1-yl)ethyl)pyrido[2,3-d]pyrimidin-7(8H)-one (230 mg, 0.5 mmol) in DMF (5 mL) was added DIPEA (258 mg, 2 mmol), HBTU (380 mg, 1 mmol) and 2-cyano-4,4-dimethylpent-2-enoic acid (153 mg, 1.0 mmol). The mixture was stirred at ambient temperature for 2 h before eluting with ethyl acetate (100 mL). The resulting mixture was washed with brine (3×50 mL), the organic layer was dried over anhydrous sodium sulfate, filtered, evaporated under vacuum to afford 2-(4-(2-(6-(2-chloro-3,5-dimethoxyphenyl)-2-(methylamino)-7-oxopyrido[2,3-d]pyrimidin-8(7H)-yl)ethyl)piperazine-1-carbonyl)-4,4-dimethylpent-2-enenitrile as a white solid (60 mg, 20%). MS (pos. ion) m/z: 594 (M+1).

Example 9

Synthesis of N-(1-(2-(6-(2-chloro-3,5-dimethoxyphenyl)-2-(methylamino)-7-oxopyrido[2,3-d]pyrimidin-8(7H)-yl)ethyl)piperidin-4-yl)-2-cyano-4,4-dimethylpent-2-enamide

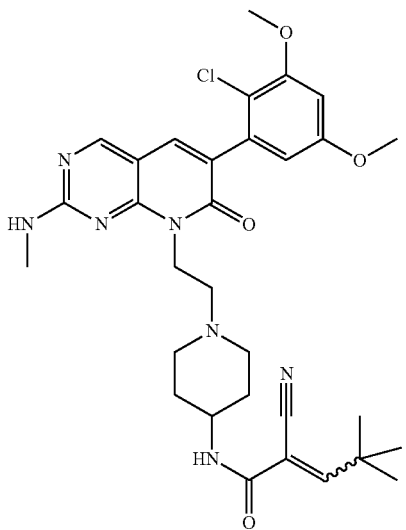

Step 1

To a solution of tert-butyl piperidin-4-ylcarbamate (2.5 g, 12.5 mmol) in methanol (25 mL) was added potassium carbonate (6.9 g, 50 mmol) and 2-bromoethanol (3.1 g, 25 mmol). The mixture was stirred at ambient temperature overnight before evaporating under vacuum. The residue was diluted with water and extracted with ethyl acetate. The organic layer was dried over anhydrous sodium sulfate, filtered, and evaporated under vacuum to tert-butyl (1-(2-hydroxyethyl)piperidin-4-yl)carbamate as a light yellow oil (1.9 g, 61%) after purification by flash chromatography (silica gel, petroleum ether/ethyl acetate=5:1).

Step 2

To a solution of tert-butyl (1-(2-hydroxyethyl)piperidin-4-yl)carbamate (1.8 g, 7.5 mmol) in dichloromethane (10 mL) was added DIPEA (1.9 g, 15 mmol), MsCl (1.2 g, 10 mmol) at 0° C., then the mixture was stirred at ambient temperature for 1 h before quenching with water (50 mL). The mixture was diluted with dichloromethane and washed with aqueous sodium bicarbonate and brine. The organic layer was dried over anhydrous sodium sulfate, filtered, and evaporated under vacuum to obtain 2-(4-((tert-butoxycarbonyl)amino)piperidin-1-yl)ethyl methanesulfonate as a yellow solid (2.40 g, crude) which was used for the next step.

Steps 3-6

Proceeding as in steps 2-5 in example 8, but replacing tert-butyl 4-(2-((methylsulfonyl)-oxy)ethyl)piperazine-1-carboxylate with 2-(4-((tert-butoxycarbonyl)amino)piperidin-1-yl)ethyl methanesulfonate affords 8-(2-(4-aminopiperidin-1-yl)ethyl)-6-(2-chloro-3,5-dimethoxyphenyl)-2-(methylamino)pyrido[2,3-d]pyrimidin-7(8H)-one as a pale oil.

Step 7

To a solution of 8-(2-(4-aminopiperidin-1-yl)ethyl)-6-(2-chloro-3,5-dimethoxyphenyl)-2-(methylamino)pyrido[2,3-d]pyrimidin-7(8H)-one (200 mg, 0.42 mmol) in DMF (5 mL) was added (E)-2-cyano-4,4-dimethylpent-2-enoic acid (130 mg, 0.85 mmol), DIPEA (163 mg, 1.26 mmol), T3P (540 mg, 0.85 mmol), and the resultant mixture was stirred at ambient temperature for 4 h. The mixture was poured into water, exacted with ethyl acetate, and the organic layer was dried over anhydrous sodium sulfate, filtered, and evaporated under vacuum to obtain N-(1-(2-(6-(2-chloro-3,5-dimethoxyphenyl)-2-(methylamino)-7-oxopyrido[2,3-d]pyrimidin-8(7H)-yl)ethyl)-piperidin-4-yl)-2-cyano-4,4-dimethylpent-2-enamide as a white solid (60 mg, 24%) after purification by prep-HPLC. MS (pos. ion) m/z: 608 (M+1).

Example 10

Synthesis of 2-(4-(3-(6-(2-chloro-3,5-dimethoxyphenyl)-2-(methylamino)-7-oxopyrido[2,3-d]pyrimidin-8(7H)-yl)propyl)piperazine-1-carbonyl)-4,4-dimethylpent-2-enenitrile

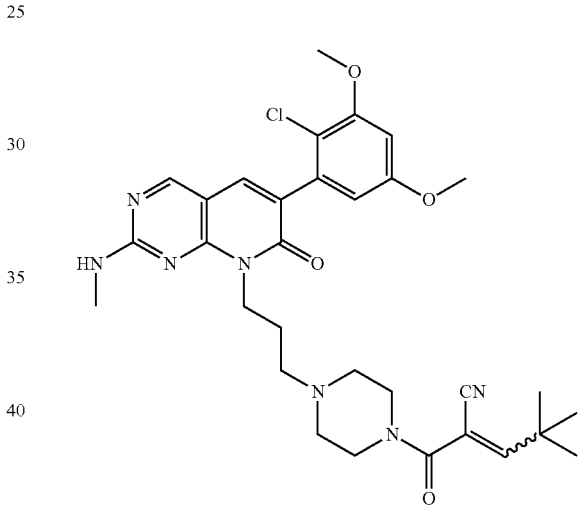

Step 1

A mixture of 3-(piperazin-1-yl)propan-1-ol (1.44 g, 10 mmol), Boc$_2$O (3.3 g, 15 mmol) and DIPEA (1.80 g, 15 mmol) in DCM (100 mL) was stirred at room temperature until the starting material was consumed. Additional DCM was added and the organic layer was washed with brine, dried over anhydrous sodium sulfate, filtered, and evaporated under vacuum to give a residue which was purified by column chromatography (silica gel, DCM:MeOH=20:1) to give tert-butyl 4-(3-hydroxypropyl)piperazine-1-carboxylate (2.4 g, 97%) as a colorless oil.

Step 2

A mixture of tert-butyl 4-(3-hydroxypropyl)piperazine-1-carboxylate (1.52 g, 6.2 mmol), Ph$_3$P (2.46 g, 9.4 mmol), I$_2$ (2.40 g, 9.4 mmol) and imidazole (1.28 g, 18.6 mmol) in DCM (100 mL) was stirred at room temperature for 5 h. The mixture was diluted with DCM and the organic layer was washed with brine, dried over anhydrous sodium sulfate, filtered, and evaporated under vacuum to give a residue which was purified by column chromatography (silica gel, PE:EtOAc=5:1) to afford tert-butyl 4-(3-iodopropyl)piperazine-1-carboxylate (1.10 g, 50%) as a colorless oil.

Step 3

A mixture of tert-butyl 4-(3-iodopropyl)piperazine-1-carboxylate (0.93 g, 2.64 mmol), 6-(2-chloro-3,5-dimethoxyphenyl)-2-(methylthio)pyrido[2,3-d]pyrimidin-7(8H)-one (0.80 g, 2.2 mmol), and K₂CO₃ (0.61 g, 4.4 mmol) in DMF (10 mL) was stirred at 80° C. for 1 h before cooling down to room temperature. Ethyl acetate was added and the organic layer was washed with brine, dried over anhydrous sodium sulfate, filtered, and evaporated under vacuum to give tert-butyl 4-(3-(6-(2-chloro-3,5-dimethoxyphenyl)-2-(methylthio)-7-oxopyrido[2,3-d]pyrimidin-8(7H)-yl)propyl)piperazine-1-carboxylate (1.30 g) as a yellow oil which was used without further purification.

Step 4

A mixture of tert-butyl 4-(3-(6-(2-chloro-3,5-dimethoxyphenyl)-2-(methylthio)-7-oxopyrido[2,3-d]pyrimidin-8(7H)-yl)propyl)piperazine-1-carboxylate (1.30 g, 2.2 mmol) and m-CPBA (0.62 g, 6.6 mmol) in DCM (50 mL) was stirred at room temperature for 30 min. Additional DCM was added (200 mL) and the organic layer was washed with brine, dried over anhydrous sodium sulfate, filtered, and evaporated under vacuum to give 4-(tert-butoxycarbonyl)-1-(3-(6-(2-chloro-3,5-dimethoxyphenyl)-2-(methylsulfinyl)-7-oxopyrido[2,3-d]pyrimidin-8(7H)-yl)propyl)piperazine 1-oxide (1.33 g) as a yellow oil which was used without further purification.

Step 5

A mixture of 4-(tert-butoxycarbonyl)-1-(3-(6-(2-chloro-3,5-dimethoxyphenyl)-2-(methylsulfinyl)-7-oxopyrido[2,3-d]pyrimidin-8(7H)-yl)propyl)piperazine 1-oxide (1.33 g, 2.2 mmol), MeNH₂.HCl (300 mg, 5.4 mmol), DIPEA (851 mg, 6.6 mmol) in DMSO (10 mL) was stirred at 85° C. for 1 h before cooling to room temperature. EtOAc (200 mL) was added and the organic layer was washed with brine, dried over anhydrous sodium sulfate, filtered and evaporated under vacuum to give tert-butyl 4-(3-(6-(2-chloro-3,5-dimethoxyphenyl)-2-(methylamino)-7-oxopyrido[2,3-d]pyrimidin-8(7H)-yl)propyl)piperazine-1-carboxylate (1.26 g) as a yellow oil which was used without further purification.

Step 6-7

Proceeding as in Ex 8, steps 5 and 6 but replacing tert-butyl 4-(2-(6-(2-chloro-3,5-dimethoxyphenyl)-2-(methylamino)-7-oxopyrido[2,3-d]pyrimidin-8(7H)-yl)ethyl)piperazine-1-carboxylate with tert-butyl 4-(3-(6-(2-chloro-3,5-dimethoxyphenyl)-2-(methylamino)-7-oxopyrido[2,3-d]pyrimidin-8(7H)-yl)propyl)piperazine-1-carboxylate afforded 2-(4-(3-(6-(2-chloro-3,5-dimethoxyphenyl)-2-(methylamino)-7-oxopyrido[2,3-d]pyrimidin-8(7H)-yl)propyl)piperazine-1-carbonyl)-4,4-dimethylpent-2-enenitrile as a colorless solid. MS (pos. ion) m/z: 608 (M+1).

Example 11

Synthesis of 2-((3aR,6aS)-5-(2-(6-(2-chloro-3,5-dimethoxyphenyl)-2-(methylamino)-7-oxopyrido[2,3-d]pyrimidin-8(7H)-yl)ethyl)octahydropyrrolo[3,4-c]pyrrole-2-carbonyl)-4,4-dimethylpent-2-enenitrile

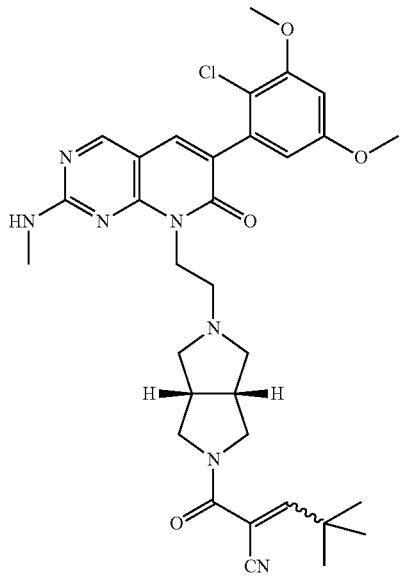

Step 1

To a solution of 1H-pyrrole-2,5-dione (12.6 g, 130 mmol) in dichloromethane (150 mL) was added TFA (1.1 mL) and a solution of N-benzyl-1-methoxy-N-((trimethylsilyl)methyl)-methanamine (33.9 g, 143 mmol) in dichloromethane (50 mL) at 0° C. dropwise. The mixture was stirred at ambient temperature for 35 h. The organic layer was washed with sat. sodium bicarbonate aqueous solution, washed with brine. The organic layer was dried over anhydrous sodium sulfate, filtered, and evaporated under vacuum. The residue was stirred at ethyl acetate/heptane (1/9, 150 mL) overnight. The solid was collected and Methanol/NH2OH (aq. 50%) (2.1 mL) was added. The mixture was stirred at ambient temperature overnight. The solvent was removed and the residue was diluted with ethyl acetate and filtered to remove some insoluble materials. The filtrated was concentrated to give the (3aR,6aS)-5-benzyltetrahydropyrrolo[3,4-c]pyrrole-1,3(2H,3aH)-dione as a light yellow solid (13 g, 39%).

Step 2

To a suspension of LiAlH4 (4.3 g, 113 mmol) in tetrahydrofuran (50 mL) was added a solution of (3aR,6aS)-5-benzyltetrahydropyrrolo[3,4-c]pyrrole-1,3(2H,3aH)-dione (13 g, 56.5 mmol) in tetrahydrofuran (150 mL) at 0° C. After addition, the mixture was stirred at 0° C. for 0.5 h and refluxed for 3 h before cooling to ambient temperature. The mixture was quenched by NaOH aqueous solution (15%) (5.2 mL), filtered, the filtrated was evaporated under vacuum to afford (3aR,6aS)-2-benzyloctahydropyrrolo[3,4-c]pyrrole as a yellow oil (10 g, 88%).

Step 3

To a solution of (3aR,6aS)-2-benzyloctahydropyrrolo[3,4-c]pyrrole (10 g, 49.5 mmol) in tetrahydrofuran (100 mL) was added DIPEA (12.8 g, 99 mmol) and Boc₂O (10.8 g, 49.5 mmol). The mixture was stirred at ambient temperature for 5 h before diluting with ethyl acetate (200 mL). The mixture was washed with sodium bicarbonate aqueous solution and then washed with brine. The organic layer was dried over anhydrous sodium sulfate, filtered, evaporated under vacuum to yield (3aR,6aS)-tert-butyl 5-benzylhexahydropyrrolo[3,4-c]pyrrole-2(1H)-carboxylate as a yellow oil (12 g, 80%).

Step 4

To a solution of (3aR,6aS)-tert-butyl 5-benzylhexahydropyrrolo[3,4-c]pyrrole-2(1H)-carboxylate (5 g, 16.5 mmol) in methanol (50 mL) was added Pd(OH)$_2$/C (10%) (0.5 g). The mixture was stirred at 60° C. overnight under hydrogen atmosphere at 60 psi before cooling to ambient temperature. The reaction mixture was filtered by celite. The filtrated solution was evaporated under vacuum to obtain (3aR,6aS)-tert-butyl hexahydropyrrolo[3,4-c]pyrrole-2(1H)-carboxylate as a colorless oil (2.3 g, 66%).

Step 5

To a solution of (3aR,6aS)-tert-butyl hexahydropyrrolo[3,4-c]pyrrole-2(1H)-carboxylate (2.3 g, 10.8 mmol) in DMF (30 mL) was added potassium carbonate (3 g, 21.6 mmol) and 2-bromoethanol (2.0 g, 16.2 mmol). The mixture was stirred at ambient temperature for 8 h before exacted with ethyl acetate (50 mL). The mixture was washed with water (3×60 mL). The organic layer was dried over anhydrous sodium sulfate, filtered, evaporated under vacuum to get (3aS,6aR)-tert-Butyl 5-(2-hydroxyethyl)-hexahydropyrrolo[3,4-c]pyrrole-2(1H)-carboxylate as a yellow oil (1.7 g, 61%).

Step 6-11

Proceeding as in example 8, (3aS,6aR)-tert-Butyl 5-(2-hydroxyethyl)-hexahydropyrrolo-[3,4-c]pyrrole-2(1H)-carboxylate was reacted with MSCl and the resultant material reacted as in steps 2-6 to afford 2-((3aR,6a5)-5-(2-(6-(2-chloro-3,5-dimethoxyphenyl)-2-(methylamino)-7-oxopyrido[2,3-d]pyrimidin-8(7H)-yl)ethyl)octahydropyrrolo[3,4-c]pyrrole-2-carbonyl)-4,4-dimethylpent-2-enenitrile. MS (pos. ion) m/z: 619.7 (M+1).

Example 12

Synthesis of 2-(4-(2-(6-(2,6-dichloro-3,5-dimethoxyphenyl)-2-(methylamino)-7-oxopyrido[2,3-d]pyrimidin-8(7H)-yl)ethyl)piperazine-1-carbonyl)-4,4-dimethylpent-2-enenitrile

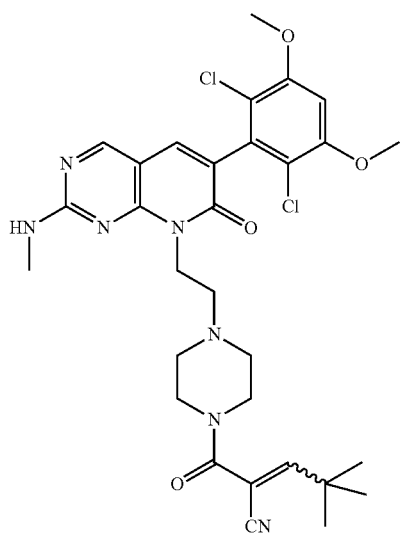

Proceeding as in example 8 but substituting 6-(2-chloro-3,5-dimethoxyphenyl)-2-(methylthio)pyrido[2,3-d]pyrimidin-7(8H)-one with 6-(2,6-dichloro-3,5-dimethoxyphenyl)-2-(methylthio)pyrido[2,3-d]pyrimidin-7(8H)-one afforded 2-(4-(2-(6-(2,6-dichloro-3,5-dimethoxyphenyl)-2-(methylamino)-7-oxopyrido[2,3-d]pyrimidin-8(7H)-yl)ethyl)piperazine-1-carbonyl)-4,4-dimethylpent-2-enenitrile. MS (pos. ion) m/z: 628 (M+1).

Example 13

Synthesis of 2-(4-(3-(6-(2,6-dichloro-3,5-dimethoxyphenyl)-2-(methylamino)-7-oxopyrido[2,3-d]pyrimidin-8(7H)-yl)propyl)piperazine-1-carbonyl)-4,4-dimethylpent-2-enenitrile

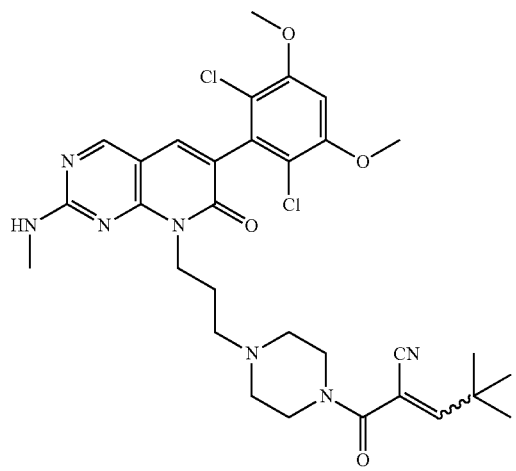

Step 1

Into a 100-mL round-bottom flask, was placed a solution of tert-butyl 4-(3-hydroxypropyl)piperazine-1-carboxylate (1.48 g, 6.06 mmol, 1.00 equiv) in dichloromethane (60 mL), imidazole (620 mg), triphenylphosphane (2.38 g, 9.07 mmol, 1.50 equiv), iodine (2.31 g, 9.10 mmol, 1.50 equiv). The resulting solution was stirred for 2 h at room temperature. The resulting mixture was concentrated under vacuum. The residue was applied onto a silica gel column with dichloromethane/methanol (50:1). This resulted in 1.65 g (77%) of tert-butyl 4-(3-iodopropyl)piperazine-1-carboxylate as yellow oil.

Step 2

Into a 100-mL round-bottom flask, was placed a solution of 6-(2,6-dichloro-3,5-dimethoxyphenyl)-2-(methylsulfanyl)-7H,8H-pyrido[2,3-d]pyrimidin-7-one (600 mg, 1.51 mmol, 1.00 equiv) in acetone (50 mL), potassium carbonate (630 mg), tert-butyl 4-(3-iodopropyl)-piperazine-1-carboxylate (640 mg, 1.81 mmol, 1.20 equiv). The resulting solution was heated to reflux for 3 h. The solids were filtered out. The residue was applied onto a silica gel column with dichloromethane/ethyl acetate (2:1). This resulted in 720 mg (77%) of tert-butyl 4-[3-[6-(2,6-dichloro-3,5-dimethoxyphenyl)-2-(methylsulfanyl)-7-oxo-7H,8H-pyrido[2,3-d]pyrimidin-8-yl]-propyl]piperazine-1-carboxylate as a yellow solid.

Step 3

Into a 100-mL round-bottom flask, was placed tert-butyl 4-[3-[6-(2,6-dichloro-3,5-dimethoxyphenyl)-2-(methylsulfanyl)-7-oxo-7H,8H-pyrido[2,3-d]pyrimidin-8-yl]propyl]- piperazine-1-carboxylate (720 mg, 1.15 mmol, 1.00 equiv), trichloromethane (50 mL), mCPBA (600 mg). The resulting solution was stirred overnight at room temperature. The reaction was then quenched by the addition of 50 mL of saturated sodium bicarbonate. The resulting solution was extracted with 2×80 mL of DCM/MeOH(10:1) and the organic layers combined and concentrated under vacuum. This resulted in 750 mg (97%) of 4-[(tert-butoxy)carbonyl]-1-[3-[6-(2,6-dichloro-3,5-dimethoxyphenyl)-2-methanesulfonyl-7-oxo-7H,8H-pyrido[2,3-d]pyrimidin-8-yl]propyl]-piperazin-1-ium-1-olate as a yellow solid.

Step 4

Into a 250-mL round-bottom flask, was placed a solution of 4-[(tert-butoxy)carbonyl]-1-[3-[6-(2,6-dichloro-3,5-dimethoxyphenyl)-2-(methylamino)-7-oxo-7H,8H-pyrido[2,3-d]-pyrimidin-8-yl]propyl]piperazin-1-ium-1-olate (680 mg, 1.09 mmol, 1.00 equiv) in methanol (100 mL), Zn (1 g), NH4Cl (sat) (4 mL). The resulting solution was stirred overnight at room temperature. The solids were filtered out. The residue was applied onto a silica gel column with dichloromethane/methanol (35:1). This resulted in 650 mg (98%) of tert-butyl 4-[3-[6-(2,6-dichloro-3,5-dimethoxyphenyl)-2-(methylamino)-7-oxo-7H,8H-pyrido[2,3-d]pyrimidin-8-yl]-propyl]-piperazine-1-carboxylate as a yellow solid.

Step 5-6

Proceeding as in example 8 steps 5 and 6, 2-(4-(3-(6-(2,6-dichloro-3,5-dimethoxyphenyl)-2-(methylamino)-7-oxopyrido[2,3-d]pyrimidin-8(7H)-yl)propyl)piperazine-1-carbonyl)-4,4-dimethylpent-2-enenitrile was obtained. MS (pos. ion) m/z: 642 (M+1).

Example 14

Synthesis of 2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4,4-dimethylpent-2-enenitrile

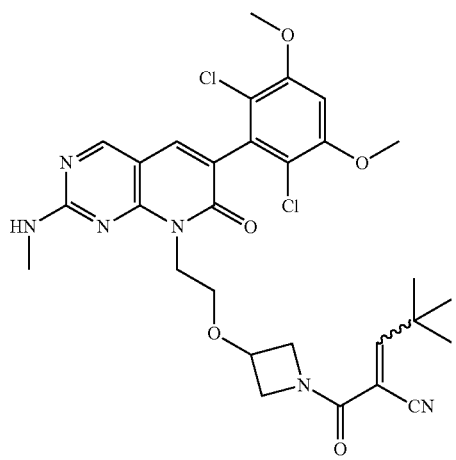

Step 1

Into a 100-mL 3-necked round-bottom flask, was placed tert-butyl 3-hydroxyazetidine-1-carboxylate (2 g, 11.55 mmol, 1.00 equiv), sodium hydride (460 mg, 11.50 mmol, 1.00 equiv), tetrahydrofuran (20 mL). This was followed by the addition of a solution of methyl 2-bromoacetate (1.52 g, 9.94 mmol, 1.00 equiv) in tetrahydrofuran (10 mL) dropwise with stirring in 2 min. The resulting solution was stirred for 2 h at room temperature. The reaction was then quenched by the addition of 2 mL of H2O. The resulting solution was diluted with 20 mL of H2O. The resulting solution was extracted with 3×40 mL of ethyl acetate and the organic layers combined. The resulting mixture was washed with 3×40 mL of sodium chloride(sat.). The mixture was dried over anhydrous sodium sulfate and concentrated under vacuum. This resulted in 1 g (35%) of tert-butyl 3-(2-methoxy-2-oxoethoxy)azetidine-1-carboxylate as yellow oil which was used without further purification.

Step 2

Into a 100-mL 3-necked round-bottom flask, was placed tert-butyl 3-(2-methoxy-2-oxoethoxy)azetidine-1-carboxylate (2.2 g, 8.97 mmol, 1.00 equiv), tetrahydrofuran (20 mL). This was followed by the addition of LAH (400 mg, 10.54 mmol, 1.20 equiv), in 3 portions at 0° C. in 30 min. The resulting solution was stirred for 2 h at room temperature. The reaction was then quenched by the addition of 0.4 mL of H2O, 0.4 mL of sodium hydroxide(15%), 1.2 mL of H2O. The solids were filtered out. The resulting mixture was concentrated under vacuum. This resulted in 1.5 g (77%) of tert-butyl 3-(2-hydroxyethoxy)azetidine-1-carboxylate as light yellow oil which was used without further purification.

Step 3

Into a 100-mL round-bottom flask, was placed tert-butyl 3-(2-hydroxyethoxy)azetidine-1-carboxylate (1.4 g, 6.44 mmol, 1.00 equiv), I2 (2.45 g, 1.50 equiv), Imidazole (0.71 g, 1.60 equiv), dichloromethane (20 mL), PPh3 (2.54 g, 9.68 mmol, 1.50 equiv). The resulting solution was stirred for 2 h at room temperature. The solids were filtered out. The resulting mixture was concentrated under vacuum. The residue was purified by chromatography to afford 1.1 g (52%) of tert-butyl 3-(2-iodoethoxy)azetidine-1-carboxylate as a yellow oil.

Step 4

Into a 100-mL round-bottom flask, was placed 6-(2,6-dichloro-3,5-dimethoxyphenyl)-2-(methylsulfanyl)-7H,8H-pyrido[2,3-d]pyrimidin-7-one (1 g, 2.51 mmol, 1.00 equiv), tert-butyl 3-(2-iodoethoxy)azetidine-1-carboxylate (980 mg, 3.00 mmol, 1.20 equiv), potassium carbonate (1 g, 7.24 mmol, 3.00 equiv), ACN (40 mL). The resulting solution was stirred overnight at 70° C. in an oil bath. The solids were filtered out. The resulting mixture was concentrated under vacuum. The residue was applied onto a silica gel column with dichloromethane/methanol (20:1). This resulted in 1.4 g (93%) of tert-butyl 3-[2-[6-(2,6-dichloro-3,5-dimethoxyphenyl)-2-(methylsulfanyl)-7-oxo-7H,8H-pyrido[2,3-d]pyrimidin-8-yl]ethoxy]azetidine-1-carboxylate as a yellow solid.

Steps 5-8

Proceeding as in example 8, afforded 2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4,4-dimethylpent-2-enenitrile. MS (pos. ion) m/z: 615 (M+1).

Example 15

Synthesis of 2-(3-(2-(6-(2,6-dichloro-3,5-dimethoxyphenyl)-2-(methylamino)-7-oxo-pyrido[2,3-d]pyrimidin-8(7H)-yl)ethoxy)piperidine-1-carbonyl)-4,4-dimethylpent-2-enenitrile

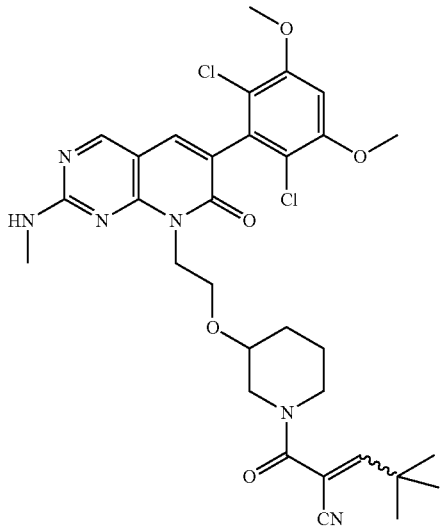

Proceeding as in example 14 but substituting tert-butyl 3-hydroxyazetidine-1-carboxylate with tert-butyl 3-hydroxypiperidine-1-carboxylate, afforded 2-(3-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4,4-dimethylpent-2-enenitrile. MS (pos. ion) m/z: 643 (M+1).

Example 16

Synthesis of 2-(3-(2-(6-(2,6-dichloro-3,5-dimethoxyphenyl)-2-(methylamino)-7-oxo-pyrido[2,3-d]pyrimidin-8(7H)-yl)ethoxy)pyrrolidine-1-carbonyl)-4,4-dimethylpent-2-enenitrile

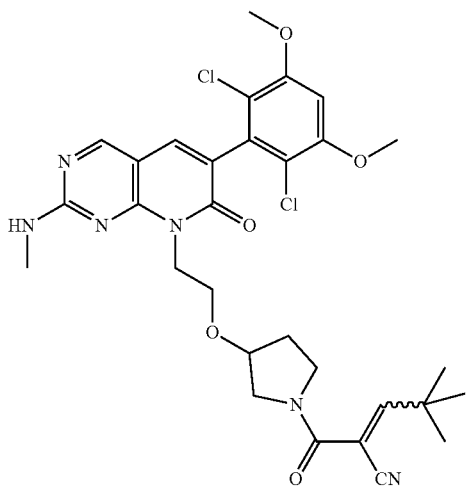

Proceeding as in example 14 but substituting tert-butyl 3-hydroxyazetidine-1-carboxylate with tert-butyl 3-hydroxypyrrolidine-1-carboxylate, afforded 2-(3-(2-(6-(2,6-dichloro-3,5-dimethoxyphenyl)-2-(methylamino)-7-oxopyrido[2,3-d]pyrimidin-8(7H)-yl)ethoxy)pyrrolidine-1-carbonyl)-4,4-dimethylpent-2-enenitrile. MS (pos. ion) m/z: 629 (M+1).

Example 17

Synthesis of 2-(3-(2-(6-(2,6-dichloro-3,5-dimethoxyphenyl)-2-((4-(diethylamino)butyl-)-amino)-7-oxopyrido[2,3-d]pyrimidin-8(7H)-yl)ethyl)piperidine-1-carbonyl)-4-methylpent-2-enenitrile

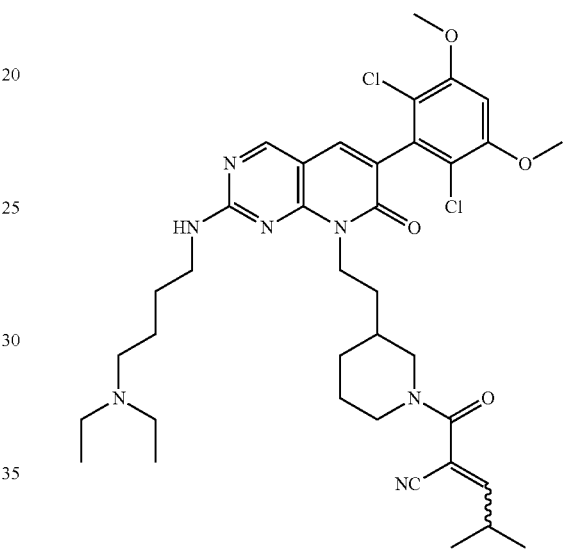

Step 1

To a mixture of 6-(2-chlorophenyl)-2-(methylthio) pyrido[2,3-d]pyrimidin-7(8H)-one (3.03 g, 10 mmol, 1.0 equiv), tert-butyl 3-(2-hydroxyethyl)piperidine-1-carboxylate (2.52 g, 11 mmol, 1.1 equiv) and PPh3 (5.24 g, 20 mmol, 2.0 equiv) in DMF (30 mL) was added dropwise DIAD (4.04 g, 20 mmol, 2.0 equiv) at 0° C. under N2. The mixture was stirred at rt overnight. The resulting mixture was poured into water and extracted with EA, washed with water, dried over anhydrous sodium sulfate and concentrated under vacuum. The residue was purified by column chromatography using PE/EA (10/1 to 3/1). This resulted in 5.15 g (60%) of tert-butyl 3-(2-(6-(2-chlorophenyl)-2-(methylthio)-7-oxopyrido[2,3-d]pyrimidin-8(7H)-yl)ethyl)piperidine-1-carboxylate as a white solid.

Step 2

To a mixture of tert-butyl 3-(2-(6-(2-chlorophenyl)-2-(methylthio)-7-oxopyrido[2,3-d]pyrimidin-8(7H)-yl)ethyl)piperidine-1-carboxylate (3.09 g, 6 mmol, 1 equiv) in CHCl3 (150 mL) was added slowly portionwise mCPBA (85%, 3.65 g, 18 mmol, 3.0 equiv). The reaction was stirred at rt overnight. The mixture was washed with sat. NaHCO3 solution and brine, dried over anhydrous sodium sulfate. The solids were filtered and concentrated under vacuum. This resulted in 4.1 g of tert-butyl 3-(2-(6-(2-chlorophenyl)-2-(methylsulfonyl)-7-oxopyrido[2,3-d]pyrimidin-8(7H)-yl)ethyl)piperidine-1-carboxylate as a brown oil which was used without further purification.

Step 3

A solution of tert-butyl 3-(2-(6-(2-chlorophenyl)-2-(methylsulfonyl)-7-oxopyrido[2,3-d]pyrimidin-8(7H)-yl)ethyl)piperidine-1-carboxylate (3.27 g, 6 mmol, 1.0 equiv) and N1, N1-diethylbutane-1,4-diamine (2.6 g, 18 mmol, 3.0 equiv) in Py (20 mL) was heated to 80° C. for 2 hours. The mixture was poured into water and extracted with EA. The organic layer was washed with brine, dried over anhydrous sodium sulfate. The solids were filtered and concentrated under vacuum. The residue was purified by column chromatography using EA/MeOH (30/1 to 5/1). This resulted in 2.2 g (60%) of tert-butyl 3-(2-(6-(2-chlorophenyl)-2-(4-(diethylamino)butylamino)-7-oxopyrido[2,3-d]pyrimidin-8(7H)-yl)ethyl)piperidine-1-carboxylate as a brown solid.

Step 4

To a mixture of tert-butyl 3-(2-(6-(2-chlorophenyl)-2-(4-(diethylamino)butylamino)-7-oxopyrido[2,3-d]pyrimidin-8(7H)-yl)ethyl)piperidine-1-carboxylate (0.8 g, 1.3 mmol, 1.0 equiv) in DCM (8 mL) was added TFA (2 mL). The reaction was stirred overnight at rt. The solution was concentrated. To the residue was added sat.Na2CO3 solution. The resulting mixture was extracted with ethyl acetate. The organic layer was washed with brine, dried over anhydrous sodium sulfate and concentrated under vacuum. This resulted in 0.62 g (93%) of 6-(2-chlorophenyl)-2-(4-(diethylamino)butylamino)-8-(2-(piperidin-3-yl)ethyl)pyrido[2,3-d]pyrimidin-7(8H)-one as a brown solid.

Step 5

To a solution of 6-(2-chlorophenyl)-2-(4-(diethylamino)butylamino)-8-(2-(piperidin-3-yl) ethyl)pyrido[2,3-d]pyrimidin-7(8H)-one (511 mg, 1 mmol, 1.0 eq) in DMF (20 mL) was added 2-cyanoacetic acid (128 mg, 1.5 mmol, 1.5 eq), HATU (570 mg, 1.5 mmol, 1.5 eq), and Et3N (505 mg, 5 mmol, 5 eq) at room temperature. Then the reaction was stirred overnight at room temperature under N2 atmosphere. Then the reaction was quenched with H2O (50 mL), extracted with EA (50 mL×3), washed with brine (50 mL×1), dried over Na2SO4, concentrated and purified with silica gel column (EA/MeOH=20/1) to give 480 mg (83%) of 3-(3-(2-(2-(4-(diethylamino)-butylamino)-6-(2-chlorophenyl)-7-oxopyrido[2,3-d]pyrimidin-8(7H)-yl)ethyl)piperidin-1-yl)-3-oxopropanenitrile as a yellow solid.

Step 6

To a solution of 3-(3-(2-(2-(4-(diethylamino)butylamino)-6-(2-chlorophenyl)-7-oxopyrido-[2,3-d]pyrimidin-8(7H)-yl)ethyl)piperidin-1-yl)-3-oxopropanenitrile (193 mg, 0.33 mmol, 1 eq) in EtOH (15 mL) was added isobutyraldehyde (120 mg, 1.67 mmol, 5 eq), piperidine (56 mg, 0.66 mmol, 2 eq) at room temperature. Then the reaction was stirred for 2 h at room temperature. Then the reaction was concentrated. The crude product was purified by prep-HPLC with the following conditions (IntelFlash-1): Column, C18 silica gel; mobile phase, CH3CN/H2O (0.05% TFA)=5/100 increasing to CH3CN/H2O (0.05% TFA)=20/100 within 30 min; Detector, UV 254 nm. After removing MeCN, the pH of the aqueous phase was adjusted to 9, then it was extracted with DCM. The organic layers were combined, washed with brine, dried over sodium sulfate, filtrate and concentrated. This resulted in 20.0 mg (9.6%) of 2-(3-(2-(6-(2,6-dichloro-3,5-dimethoxyphenyl)-2-((4-(diethylamino)butyl)amino)-7-oxopyrido[2,3-d]pyrimidin-8(7H)-yl)ethyl)piperidine-1-carbonyl)-4-methylpent-2-enenitrile as a white solid. MS (pos. ion) m/z: 632 (M+1).

BIOLOGICAL EXAMPLES

Example 1

FGFR Family Enzymatic Activity Assay

A Caliper-based kinase assay (Caliper Life Sciences, Hopkinton, Mass.) was used to measure inhibition of FGFR family (FGFR1, FGFR2, FGFR3, FGFR4) kinase activity of a compound of Formula (I). Serial dilutions of test compounds were incubated with either human recombinant FGFR1 (0.5 nM), FGFR2 (0.1 nM, FGFR3 (0.9 nM), or FGFR4 (2 nM), ATP (FGFR1: 100 μM; FGFR2: 75 μM; FGFR3: 120 μM; FGFR4: 250 μM) and a phosphoacceptor peptide substrate FAM-KKKKEEIYFFF-CONH$_2$ (1 μM) at room temperature for 3 h. The reaction was then terminated with EDTA, final concentration 20 mM and the phosphorylated reaction product was quantified on a Caliper LabChip 3000. Percent inhibition was calculated for each compound dilution and the concentration that produced 50% inhibition was calculated. This value is presented as the IC$_{50}$. The IC$_{50}$ values IC$_{50}$ values (uM) for a representative no. of compounds of the disclosure are provided below.

| Cpd No. (see Cpd table 1 above) | FGFR1 in (uM) | Cpd No. (see Cpd 1 table above) | FGFR1 in (uM) | Cpd No. (see Cpd table 1 above) | FGFR1 in (uM) |
|---|---|---|---|---|---|
| 1 | 0.3311 | 5 | 0.005 | 9 | 0.0015 |
| 2 | 0.0226 | 6 | 0.0465 | 10 | 0.0048 |
| 3 | 0.0076 | 7 | 0.0007 | | |
| 4 | 0.0342 | 8 | 0.0006 | | |

| Cpd No. (see Cpd table 2 above) | FGFR1 in (uM) | Cpd No. (see Cpd table above) | FGFR1 in (uM) | Cpd No. (see Cpd table 2 above) | FGFR1 in (uM) |
|---|---|---|---|---|---|
| 2 | 0.3311 | 16 | 0.0138 | 31 | 0.0029 |
| 3 | 0.1259 | 17 | 0.0007 | 39 | 0.01 |
| 4 | 0.0015 | 20 | 0.002 | 43 | 0.0049 |
| 5 | 0.0019 | 21 | 0.0014 | 50 | 0.0071 |
| 7 | 0.0061 | 26 | 0.0045 | 52 | 0.0207 |
| 10 | 0.1222 | 27 | 0.0049 | 53 | 0.0046 |
| 11 | 0.0086 | 29 | 0.0036 | 58 | 1.2854 |
| 59 | 4.9987 | 65 | 0.1462 | 71 | 0.0093 |
| 60 | 0.0019 | 67 | 0.258 | 75 | 0.047 |
| 61 | 0.0038 | 68 | 0.0146 | 79 | 0.0082 |

Example 2

Inhibition of FGFR2-Dependent Cell Growth

The cell-based effects of FGFR inhibitors were determined by measuring inhibition of FGFR-dependent cell line growth. The cell lines SNU-16 was used for these assays. SNU-16 cells were seeded in a 96-well plate at 5,000 cells per well in RPMI 1640 high glucose medium with 10% fetal bovine serum (FBS. Cells were incubated at 37° C. for 24 hrs. in 5% CO$_2$. Compound dilutions were added to cells starting at a concentration of 30 uM and decreasing in tripling dilutions. The final DMSO concentration was 0.1%. The concentration range was adjusted as needed for compounds of different potencies. The cells treated with compounds were incubated for 72 hrs. at 37° C. in 5% CO$_2$. At the end of the 72 hour incubation period, cell viability was determined using the Cell-titer Glo Luminescence assay from Promega. Percent inhibition of cell growth was calculated as a percentage of untreated cell viability. The percent inhibition was plotted as a function of log compound concentration. The $IC_{50}$ was then calculated for each compound using Prism software from GraphPad. The $IC_{50}$ values (uM) for a representative no. of compounds of the disclosure are provided below.

| Cpd No. (see Cpd table 1 above) | SNU16 $IC_{50}$ values (uM) | Cpd No. (see Cpd table 2 above) | SNU16 $IC_{50}$ values (uM) |
|---|---|---|---|
| 2 | 0.0508 | 7 | 0.0087 |
| 3 | 0.034 | 8 | 0.0186 |
| 5 | 0.0272 | 9 | 0.0297 |
| 6 | 0.649 | 10 | 0.0185 |

| Cpd No. (see Cpd table 2 above) | SNU16 $IC_{50}$ values (uM) | Cpd No. (see Cpd table above) | SNU16 $IC_{50}$ values (uM) | Cpd No. (see Cpd table 2 above) | SNU16 $IC_{50}$ values (uM) |
|---|---|---|---|---|---|
| 4 | 0.0053 | 16 | 0.0439 | 39 | 0.0402 |
| 5 | 0.0015 | 17 | 0.0081 | 43 | 0.0024 |
| 7 | 0.0034 | 20 | 0.0914 | 50 | 0.0046 |
| 10 | 0.1108 | 21 | 0.0331 | 52 | 0.0157 |
| 11 | 0.0734 | 26 | 0.056 | 53 | 0.0051 |
| 60 | 0.0056 | 27 | 0.0042 | 71 | 0.0796 |
| 61 | 0.0043 | 29 | 0.0014 | 75 | 0.0872 |
| 68 | 0.0355 | 67 | 0.9365 | | |

Example 3

FGFR1 Cell-Based Activity Assay Utilizing IL3-Dependent BA/F3 Cells

An engineered, cell-based assay was utilized to test the potency of FGFR1 inhibitors in a cellular context. In this system, IL3-dependent Ba/F3 cells were modified to express an activated form of FGFR1 kinase domain. Following removal of IL3 from the culture media, the modified cells were dependent on the activity of the recombinant kinase for proliferation and survival. In these studies, Ba/F3 cells were transformed by inducting TEL fusions using viral vectors. If the compound of interest specifically blocked the activity of FGFR1, the modified cells underwent programmed cell death. The amount of cell survival was quantified using CellTiter-Glo, a well-established luminescent cell viability method. Compounds were evaluated at multiple doses using a maximum compound concentration of 5 uM and a 3-fold dilution series from this concentration.

Example 4

Tumor Xenograft Models for Assessing Efficacy of FGFR Inhibitors

Human Gastric Tumor Model:

SNU-16 human gastric cancer cell line can be used to generate a xenograft model to determine the effects of a FGFR inhibitor of the present disclosure (test compound) as a single agent treatment to target FGFR-dependent tumor growth. SNU-16 cells are grown in tissue culture as described in Example 2 above. For tumor inoculation, approximately $1 \times 10^7$ cells are mixed with Matrigel (1:1) and are implanted into the rear flank of immuno compromised Balb/c nu/nu mice. Tumor-bearing mice are monitored twice weekly in two dimensions using a caliper and the volume expressed in $mm^3$ using the formula: $V=0.5\ a \times b^2$ where a and b are the long and short diameters of the tumor respectively. Once tumor volume reaches a mean average of 175 $mm^3$ mice are randomized into 3 groups (n=8-10 per group) receiving either vehicle control (0.5% methyl cellulose w/w) or the test compound by oral gavage. Dosing continues for 5-21 days with tumor volumes measured daily or every other day. It is expected that tumor growth will be inhibited in animals treated with the test compound. In addition to anti-tumor response study, SNU-16 xenograft model can be used to access in vivo pharmacodynamics activity of a disclosure compound. Inhibition of FGFR pathway can be assessed by detection of FGFR auto phosphorylation activity. Once the tumors reach approximately 300 $mm^3$, tumor bearing mice (n=4 per group) are dosed with a compound of the disclosure. Tumor samples are collected at 8 h or 12 h post the last dosing and FGFR auto phosphorylation activity is determined. It is expected that compounds of present disclosure will inhibit FGFR auto phosphorylation activity.

Human Bladder Tumor Model:

An RT4 human bladder tumor model can be used to determine the effect of a FGFR inhibitor of the present disclosure (test compound) as a single agent on human bladder cancer. Each mouse is inoculated subcutaneously at the upper right back with RT4 tumor cells ($1 \times 10^7$) mixed with Matrigel at a 1:1 ratio. The treatments are started at day 7 after tumor inoculation. Animals are randomized into 5 treatment groups (n=7 per group). Group 1 receives the vehicle control (0.5% methyl cellulose). Group 2-5 receive different doses of the test compound and tumor sizes are measured after 29 days. It is expected that tumor growth will be inhibited in animals treated with the test compound.

Example 5

Recovery of Kinase Activity Upon Dialysis

Standard experimental methods to establish reversibility are known in the art. Protein dialysis is one such method. A solution containing a protein kinase that is inhibited by a compound of Formula I may be subjected to extensive dialysis to establish if the kinase inhibitor is reversible. Partial or complete recovery of protein kinase activity over time during dialysis is indicative of reversibility.

Method:

A compound of Formula I and/or a pharmaceutically acceptable salt thereof described herein (1 uM) is added to a solution of protein kinase (50 nM, pre-activated if necessary) in a buffer containing 20 mM Hepes [pH 8.0], 10 mM $MgCl_2$, 2.5 mM tris(2-carboxyethyl)phosphine (TCEP), 0.25 mg/mL BSA, and 100 uM ATP. After 60 min at rt, the reactions is transferred to a dialysis cassette (0.1-0.5 mL Slide-A-Lyzer, MWCO 10 kDa, Pierce) and dialyzed against 2 L of buffer (20 mM Hepes [pH 8.0], 10 mM $MgCl_2$, 1 mM DTT) at 4° C. The dialysis buffer is exchanged after 2 h, and then is exchanged every 24 h until the end of the experiment. Aliquots are removed from the dialysis cassettes every 24 h, flash frozen in liquid nitrogen, and subsequently analyzed for protein kinase activity in triplicate. Kinase activity for each sample is normalized to the DMSO control for that time point and expressed as the mean±SD.

Results: Kinase activity recovers from inhibition by reversible kinase inhibitors upon dialysis. Upon extensive dialysis at 4° C. or at room temperature, kinase activity partially or completely recovers in a time-dependent manner from inhibition by an excess (20 equiv, 1.0 uM) of reversible kinase inhibitor.

Example 6

Reversibility of Binding

The following approach was developed to differentiate compounds that form irreversible bonds with their targets, such as acrylamide compounds, from compound that bind reversibly such as reversible covalent inhibitors. Reactions were prepared with the protein target at a higher concentration than the compounds of interest. Irreversible and reversible compounds bind the target and become depleted from solution. The reactions were then treated with perturbations including both denaturation with 5 M guanidine hydrochloride and digestion with trypsin, disrupting proper folding of the target. It was found that the perturbation returns reversible compounds to solution due to dissociation from the target while irreversible compounds remained bound to the target. The concentration of compound in solution was assessed both preceding and following perturbation using high performance liquid chromatography (HPLC) coupled to tandem mass spectrometry. Compounds of the present disclosure that are reversible covalent inhibitors of FGFR1 depleted from solution in the native state and were present in solution in the perturbed state indicating that they are reversible.

Example 7

Mass Spectral Analysis

A protein kinase that is inhibited by compound of Formula I and/or a pharmaceutically acceptable salt thereof may be subjected to mass spectral analysis to assess the formation of permanent, irreversible covalent adducts. Suitable analytical methods to examine intact full protein or peptide fragments generated upon tryptic cleavage of the protein kinase are generally known in the art. Such methods identify permanent, irreversible covalent protein adducts by observing a mass peak that corresponds to the mass of a control sample plus the mass of an irreversible adduct. Two such methods are described below.

Mass Spectral Analysis of Intact Full Kinase
Method:

A protein kinase (5 uM) is incubated with a compound of Formula I and/or a pharmaceutically acceptable salt thereof (25 uM, 5 equiv) for 1 h at room temperature in buffer (20 mM Hepes [pH 8.0], 100 mM NaCl, 10 mM MgCl2). A control sample is also prepared which does not have a compound of Formula I. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software.

Results: High-resolution intact mass spectrometry analysis of a kinase that is inhibited by a compound of Formula I and/or a pharmaceutically acceptable salt thereof will reveal a spectrum similar to the kinase in the absence of inhibitor (e.g. control sample). There will be no formation of a new peak in the mass spectrum corresponding to the molecular mass of the kinase plus the molecular mass of the compound of Formula I. On the basis of this experiment no permanent, irreversible protein adduct will be apparent to one skilled in the art.

Mass Spectral Analysis of Kinase Tryptic Digest
Method:

A protein (10-100 pmols) is incubated with a compound of Formula I and/or a pharmaceutically acceptable salt thereof (100-1000 pmols, 10 equiv) for 3 hrs prior to tryptic digestion. Iodoacetamide may be used as the alkylating agent after compound incubation. A control sample is also prepared which does not the compound of Formula I. For tryptic digests a 1 ul aliquot (3.3 pmols) is diluted with 10 ul of 0.1% TFA prior to micro C18 Zip Tipping directly onto the MALDI target using alpha cyano-4-hydroxy cinnamic acid as the desorption matrix (5 mg/mol in 0.1% TFA: Acetonitrile 50:50) or Sinapinic acid as the desorption matrix (10 mg/mol in 0.1% TFA:Acetonitrile 50:50).

Results: High-resolution mass spectrometry analysis of the tryptic fragments of a kinase that is inhibited by a compound of Formula I and/or a pharmaceutically acceptable salt thereof will reveal a spectrum similar to the kinase in the absence of inhibitor (e.g. control sample). There will be no evidence of any modified peptides that are not present in the control sample. On the basis of this experiment, no permanent, irreversible protein adducts will be apparent to one skilled in the art.

Example 8

Potency of Compounds in Cells

FGFR Cell-Based Activity Assay Utilizing HUVECs Cells

The data herein demonstrate the use of human umbilical vein endothelial cells (HUVECs) to determine compound potency to FGFR pathway activity. Extracellular-signal-regulated kinases (ERKs) activity, effectors of FGFR pathway, was utilized to develop a FGFR-targeted assay to determine compound potency. Human umbilical vein endothelial cells (HUVECs) cell-based effects of FGFR inhibitors were determined by measuring inhibition of compounds on FGF-induced MAP kinases activation, (phosphorylation of p44 and p42 MAP Kinase or phospho-Erk1/2) using PerkinElmer pERK SureFire Kit. Approximately 30,000 HUVECs were seeded per well in a 96-well cell culture plate at 37° C. overnight. Cells were incubated in recommended HUVECs media with 10% fetal bovine serum (Cells were incubated at 37° C. for 24 hrs. in 5% CO2). After 24 h, media were removed and replaced by serum free media for 1 hr prior to compound treatment. Compound dilutions were added to cells starting at a concentration of 1 uM and decreasing in tripling dilutions to a final concentration of 0.05 nM. The cells treated with compounds of the present disclosure were incubated for 1 hr at 37° C. in 5% $CO_2$. At the end of the 1 h incubation period, cells were stimulated with 50 ng/ml of FGF2 for 10 mins. The reaction was stopped with 100 ul of ice cold PBS and washed once with cold PBS. After washing, cells were lysed with 50 uL of 1× lysis buffer from pERK SureFire kit (Perkin Elmer). Lysates were incubated in a pERK SureFire reaction mixture for a total of 4 hrs. At the end of the incubation period, pERK activity was measured using an Envision multilabel reader (Perkin Elmer). The raw signals for pERK activity were used to calculate IC$_{50}$ inhibition value as a function of log compound concentration for each compound using Prism software from GraphPad.

Example 9

Determination of Drug-Kinase Residence Time for FGFR1

The following is a protocol to distinguish whether a compound displays a slow or non-existent dissociation rate from FGFR1, such as typically would occur if a covalent bond is formed between the compound and the target. The read-out for slow dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM MgCl2, 0.01% Triton X-100, and 1 mM EGTA.

The first step of the procedure was incubation of 500 nM FGFR1 (Invitrogen Cat. #PV3146) with 1.5 uM of a compound of Formula (I) for 60 minutes in a volume of 10 uL. The mixture was then diluted 40-fold by mixture of 2 uL FGFR1/cmpd with 78 uL buffer. A 10 uL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For FGFR1, the competition solution contained 8 uM Tracer 236 (Invitrogen Cat. #PV5592), which is a proprietary high affinity ligand for FGFR1 coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in FGFR1.

After addition of 10 uL of the competition solution to the Greiner plate, the mixture was incubated for one hour or greater to allow time for dissociation of non-covalent inhibitors and binding of the high affinity tracer. It was expected that covalent and slow dissociating inhibitors will block binding of the tracer while rapidly dissociating non-covalent inhibitors will not. Binding of the tracer to FGFR1 was detected using TR-FRET between the Europium moiety of the Anti-histidine antibody and the AlexaFluor 647 group of Tracer 236. Binding was evaluated using a Perkin Elmer Envision instrument (Model 2101) equipped with filters and mirrors compatible with LANCE-type TR-FRET experiments. Data were plotted at percentage of signal obtained in the absence of competitor compound. The background signal was obtained by omission of FGFR1 from the reaction. If the compound is a reversible covalent inhibitor, the tracer will bind the target as the compound dissociates from the target.

Example 10

Durability of Binding in Cells

The durability of binding of a reversible covalent inhibitor can be assessed in FGFR containing cells. A system to test the durability of binding in cells involves treating SNU16 gastric carcinoma cells that have been incubated with the protein synthesis inhibitor cycloheximide at 5 ug/ml with compound for a time period adequate for complete binding to occur (e.g., one hour), followed by removal of the compound from the cell culture medium by extensive washing. Then at 4 h after washing away the compound, the FGFR2-containing SNU16 cells are examined for FGFR2 occupancy of the test compound using an FGFR specific fluorescence occupancy probe or by monitoring a downstream readout of FGFR signaling such as phosphoFGFR or phosphoERK. Cellular durability 4 h post-washout can be a property of reversible covalent inhibitors that bind FGFR2 in SNU16 cells.

Example 11

PHEX Mutant Mouse Study to Evaluate Efficacy of FGFR Inhibitors for Treatment of X-Linked Hypophosphatemic Rickets A murine model of XLH can be used to determine effects of a FGFR inhibitor of the present disclosure (test compound) as a single agent treatment to target aberrant FGF23 signaling, thus alleviating the hypophosphatemic conditions of the mice, which can lead to enhanced bone growth. The XLH murine model exhibits a nonsense mutation (K496X) in exon 14 of the Phex gene and mimics the human disease XLH (Owen et al., 2012. A novel Phex mutation in a new mouse model of hypophosphatemic rickets. *J Biochem Chem* 113(7): 2432-41). Mice are dosed with test compounds and once dosing schedule is completed, mice are anesthetized with a ketamine/xylazine mix and blood drawn by cardiac puncture. Serum alkaline phosphatase, blood urine nitrogen (BUN), calcium, creatinine and phosphorus can be measured using Roche COBAS Mira S (Roche Diagnostics, Indianapolis, Ind., USA). Phosphate levels are also be determined using a contract research company (IDEXX Preclinical Research Services). Intact FGF23 levels can be measured using an FGF-23 ELISA kit which detects only intact FGF23 (Kainos Laboratories Inc, Japan). Serum concentrations of 1,25(OH)$_2$D$_3$ can be determined using 1,25-dihydroxy Vitamin D EIA kit (Immunodiagnostic Systems Ltd., Fountain Hills, Ariz., USA). Parathyroid hormone (Pth) can be measured using PTH 1-84 ELISA kit (Immunotopics). After blood draw, kidneys and femurs are collected and stored in RNA later RNA Stabilization Reagant (Qiagen Inc, Valencia, Calif., USA). Total RNA are extracted from whole femurs and kidneys, using TRIzol Plus RNA Purification System (Invitrogen, Carlsbad, Calif., USA) and used for first-strand cDNA synthesis, using High Capacity cDNA Reverse Transcription Kit (Applied Biosystems, Foster City, Calif., USA). The cDNA are subsequently used for quantification of FGF23, Slc34a1, Slc34a3, Kl, Cyp27b1 and Cyp24a1 expression by probe-based quantitative PCR, using TaqMan Gene Expression Master Mix in 7900HT Fast Real-Time PCR System (Applied Biosystems). GADPH can also be determined as a housekeeping gene to normalize gene expression. Femurs are harvested from mice and fixed in 10% neutral-buffered formalin for 2 days. A real bone mineral density (BMD) and bone mineral content (BMC) are measured using a PIXImus2 densitometer (LUNAR Corp, Madison, Wis.). Radiographs of femur and tibia can be used for quantification of femoral and tibial length. μCT scan of femoral cortex (sub-growth plate metaphyseal area) can also be conducted for quantification of relative cortical bone volume and average cortex thickness.

Results: Inhibition of FGFR signaling by test compounds will lead to increases in phosphate, FGF23 and 1,25(OH)$_2$D$_3$ levels, increases in gene expression of FGF23, Cyp27b1, Cyp24a1 and enhanced bone growth as determined by femoral and tibial length and cortex integrity of the femoral bones.

FORMULATION EXAMPLES

The following are representative pharmaceutical formulations containing a compound of the present disclosure.

Tablet Formulation

The following ingredients are mixed intimately and pressed into single scored tablets.

| Ingredient | Quantity per tablet mg |
| --- | --- |
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
| --- | --- |
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 ul of spray for each application.

What is claimed is:
1. A compound of Formula (I):

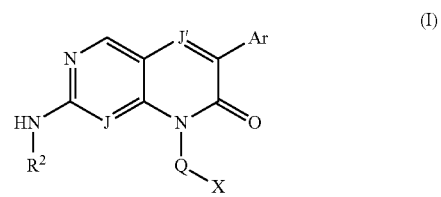

wherein:
J is N or CH;
J' is N or $CR^1$ where $R^1$ is hydrogen, halo, alkyl, or cycloalkyl;
Ar is phenyl or heteroaryl, each ring optionally substituted with one, two, three, or four substituents independently selected from alkyl, cycloalkyl, hydroxy, alkoxy, halo, haloalkyl, alkyl sulfonyl, haloalkoxy, and cyano;
$R^2$ is hydrogen, alkyl, alkynyl, acyl, alkoxycarbonyl, haloalkyl, cycloalkyl optionally substituted with amino, alkylamino, dialkylamino, or hydroxyl, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, alkoxy, hydroxyalkyl, alkoxyalkyl, alkoxyalkyloxy, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, hydroxy, alkoxy, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where phenyl, phenyl ring in aralkyl, heteroaryl ring in heteroaralkyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl, or optionally substituted heterocyclyl); and
(i) Q is alkylene and X is $-NR^b-Y-C(CN)=CHR^c$; or
(ii) Q is alkylene, substituted alkylene, heteroalkylene, substituted heteroalkylene, or alkylene-cycloalkylene-alkylene; and X is a group of formula (a), (b), (c), or (d):

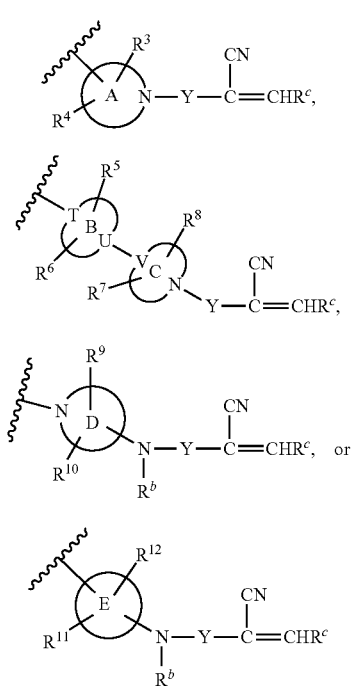

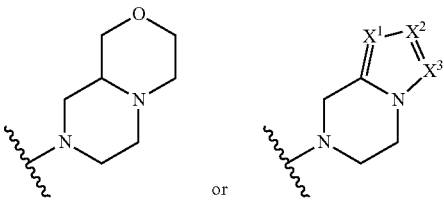

wherein:
T, U, and V, are independently N or CH provided that at least one of T and U is nitrogen;
ring A is heterocycloamino; bridged heterocycloamino, or spiroheterocycloamino;
rings B and C are independently azetidinyl, pyrrolidinyl, piperidinyl, homopiperidinyl, piperazinyl, or imidazolidine;
ring D is azetidinyl, pyrrolidinyl, piperidinyl, bridged heterocycloamino, or spiro heterocycloamino;
ring E is 5- or 6-membered cycloalkylene, phenylene, or 5- or 6-membered heteroarylene;
$R^3$, $R^4$, $R^5$, $R^6$, $R^7$, $R^8$, $R^9$, and $R^{10}$ are independently hydrogen, alkyl, hydroxy, alkoxy, or halo; and
$R^{11}$ is hydrogen, alkyl, hydroxy, alkoxy, halo, haloalkyl, haloalkoxy, or cyano;
$R^{12}$ is hydrogen, alkyl, cycloalkyl, hydroxy, alkoxy, halo, haloalkyl, haloalkoxy, or cyano;
each Y is —CO— or —SO$_2$—;
each $R^b$ is hydrogen or alkyl; and
each $R^c$ is alkyl, alkoxyalkyloxyalkyl, cycloalkyl (optionally substituted with alkyl), 1-aminocycloalk-1-yl, substituted alkyl, heterocyclylalkyl, heterocyclyl (wherein the heterocyclyl in heterocyclylalkyl and heterocyclyl are each independently optionally substituted with one, two, or three substituents where two of the optional substituents are independently selected from alkyl, alkoxy, hydroxy, halo, amino, and oxo, and one of the optional substituent is alkyl, hydroxyalkyl, alkoxyalkyl, acyl, haloalkyl, alkylsulfonyl, alkoxycarbonyl, or heterocyclyl wherein the heterocyclyl is optionally substituted with one or two substitutents independently selected from alkyl, halo, hydroxy, or alkoxy), heteroaralkyl (wherein the heteroaryl ring is optionally substituted with one or two substituents independently selected from alkyl, amino, alkylamino, or dialkylamino), bridged heterocycloaminoalkyl or spiroheterocycloaminoalkyl (wherein each of the aforementioned ring is optionally substituted with one or two alkyl and further wherein the alkylene chain in bridged heterocycloaminoalkyl or spiroheterocycloaminoalkyl is attached to the nitrogen atom of the bridged heterocycloamino and spiroheterocycloamino group), or -(alkylene)-NR$^{13}$R$^{14}$ where R$^{13}$ and R$^{14}$ together with the nitrogen atom to which they are attached form

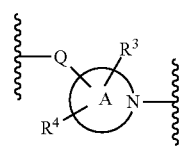

where one or two of $X^1$, $X^2$ and $X^3$ are nitrogen and the rest are carbon and the ring is optionally substituted with one or two substituents independently selected from alkyl, haloalkyl, and halo;
and/or a pharmaceutically acceptable salt thereof;
provided that: (1) when (i) ring E is 6-membered cycloalkylene, phenylene, or 6-membered heteroarylene or (ii) ring D is piperidinyl, then Q and —NR$^b$—Y—C(CN)=CHR$^c$ are meta or para to each other; (2) when ring A is piperidinyl, then Q and —Y—C(CN)=CR$^c$R$^d$ are meta or para to each other; (3) when ring A is piperazinyl, then Q and —Y—C(CN)=CHR$^c$ are para to each other; and (4) when rings A and D are pyrrolidinyl or azetidinyl, then Q and —NR$^b$—Y—C(CN)=CHR$^c$ or Q and —Y—C(CN)=CHR$^c$ are (1,3) to each other.

2. The compound of claim 1 or a pharmaceutically acceptable salt thereof, wherein J is CH.

3. The compound of claim 1 or a pharmaceutically acceptable salt thereof, wherein J is N.

4. The compound of claim 1 or a pharmaceutically acceptable salt thereof, wherein J' is —CR$^1$, wherein R$^1$ is hydrogen, methyl, chloro, or fluoro.

5. The compound of claim 1 or a pharmaceutically acceptable salt thereof, wherein Ar is phenyl optionally substituted with one, two, three, or four substituents independently selected from alkyl, hydroxy, alkoxy, halo, haloalkyl, haloalkoxy, and cyano.

6. The compound of claim 5 or a pharmaceutically acceptable salt thereof, wherein Ar is 3-methoxyphenyl, 2-halo-3-methoxyphenyl, 2-halo-5-methoxyphenyl, 2-halo-3,5-dimethoxyphenyl, 2,6-dihalo-3,5-dimethoxyphenyl, 3,5-dimethoxyphenyl, 2-halophenyl, or 2,6-dihalophenyl.

7. The compound of claim 1 or a pharmaceutically acceptable salt thereof, wherein X is a group of formula (a) or (b), wherein in formula (a) is
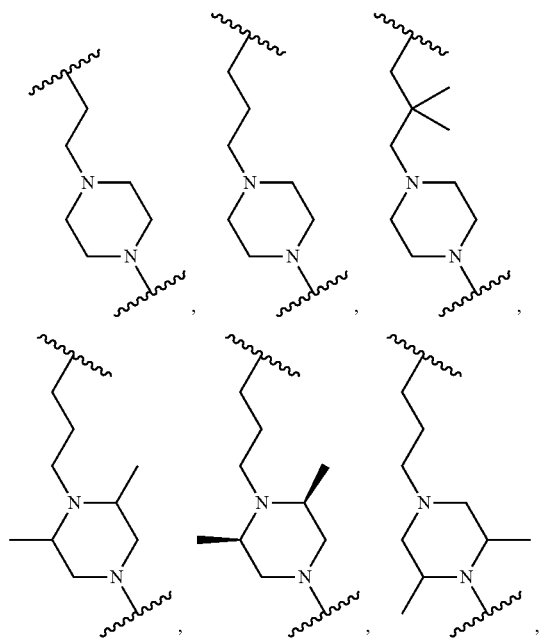
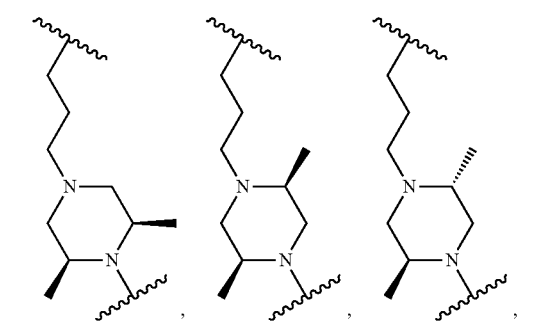
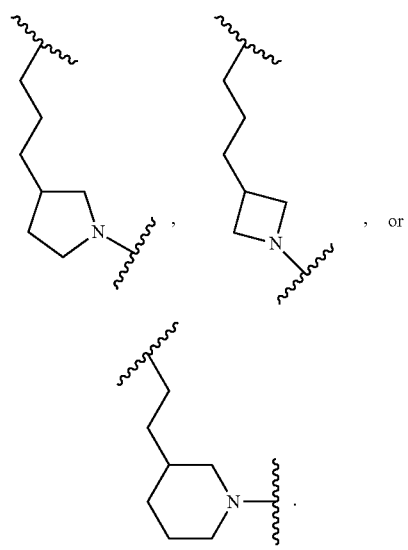
8. The compound of claim 7 or a pharmaceutically acceptable salt thereof, wherein Q is -alkylene.
9. The compound of claim 7 or a pharmaceutically acceptable salt thereof, wherein Q is heteroalkylene.
10. The compound of claim 1 or a pharmaceutically acceptable salt thereof, wherein X is a group of formula (a) wherein
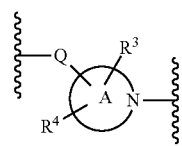
in formula (a) is:
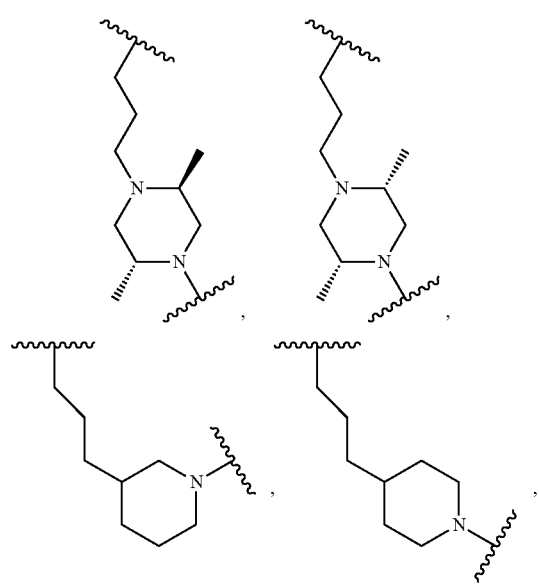
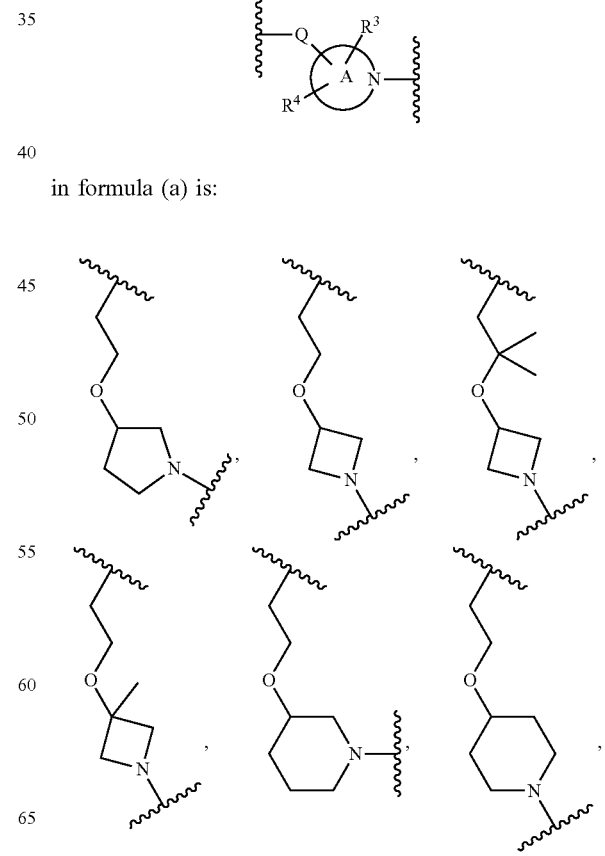

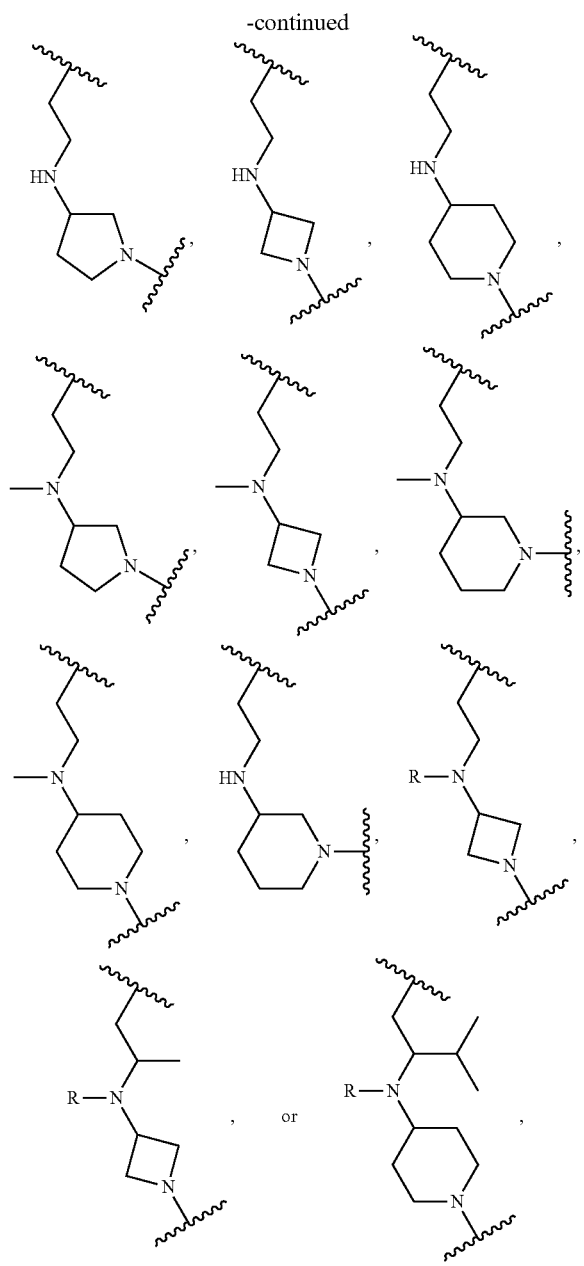

wherein each R independently is methyl, ethyl, isopropyl, 2-hydroxyethyl, or 2-alkoxyethyl.

11. The compound of claim 1 or a pharmaceutically acceptable salt thereof, wherein X is a group of formula (c) or (d).

12. The compound of claim 11 or a pharmaceutically acceptable salt thereof, wherein ring D is piperidin-1-yl, pyrrolidinyl, or azetidin-1-yl.

13. The compound of claim 12 or a pharmaceutically acceptable salt thereof, wherein $R^b$ is hydrogen.

14. The compound of claim 1 or a pharmaceutically acceptable salt thereof, wherein $R^2$ is hydrogen, alkyl, alkynyl, acyl, alkoxycarbonyl, haloalkyl, cycloalkyl optionally substituted with hydroxy, cycloalkylalkyl, hydroxyalkyl, alkoxyalkyl, alkoxyalkyloxyalkyl, aminoalkyl, heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, alkoxyalkyl, aminoalkyl, optionally substituted aryl, optionally substituted heteroaryl, and optionally substituted heterocyclyl), aralkyl, heteroaralkyl, phenyl, or heteroaryl (where the phenyl ring in aralkyl, the heteroaryl ring in heteroaralkyl, phenyl and heteroaryl are optionally substituted with one, two, or three substituents where two of the optional substituents are independently selected from alkyl, hydroxy, alkoxy, halo, haloalkyl, haloalkoxy, and cyano and one of the optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl).

15. The compound of claim 14, or a pharmaceutically acceptable salt thereof wherein $R^2$ is:
alkyl, selected from methyl, ethyl, isopropyl, and 2,2-dimethylpropyl;
cycloalkyl optionally substituted with alkyl, wherein said optionally substituted cycloalkyl is selected from cyclopropyl, cyclobutyl, cyclopentyl, 1-methylcyclopropylene, 1-methylcyclobutylene, and 1-methylcyclopentylene;
hydroxyalkyl, selected from 2-hydroxyethyl, 3-hydroxyprop-2-yl, 2,3-dihydroxypropyl, 2,2-dimethyl-3-hydroxypropyl, 2-hydroxy-2-methylpropyl, 2-methyl-3-hydroxyprop-2-yl, 1-hydroxy-2-hydroxymethylprop-2-yl, 1,3-dihydroxyprop-2-yl, and 3-hydroxy-2-hydroxymethylbut-2-yl
alkoxyalkyl or alkoxyalkoxyalkyl, selected from 2-isopropoxyethyl, 3-methoxyprop-2-yl, 2-ethoxyethyl, 1-3-dimethoxyprop-2-yl, 3-ethoxyprop-2-yl, 2-methoxyethyl, and 2-methoxy ethoxy ethyl;
heterocyclylalkyl (wherein the heterocyclyl ring in heterocyclylalkyl is optionally substituted with one, two, or three substituents independently selected from alkyl, halo, acyl, alkoxycarbonyl, hydroxyalkyl, aminoalkyl, optionally substituted aryl, optionally substituted heteroaryl, and optionally substituted heterocyclyl), selected from 2-methyl-2-morpholin-4-ylpropyl, 2-(4-isopropylpiperazin-1-yl)ethyl, morpholin-4yl-ethyl, 2-(4-methylpiperazin-1-yl)ethyl, 3-morpholin-4-ylpropyl, 2,6-dimethylmorpholino-4-ethyl, 4,4-difluoropiperidin-1-ylethyl, tetrahydropyran-4-ylmethyl, 4-acetylpiperazin-1-ylethyl, 1,1-dimethyl-2-morpholin-4-ylethyl, 1,4-dimethylpiperidin-4-ylmethyl, 3-pyrrolidin-1-ylpropyl, (1-oxopyrrolidin-1-yl)ethyl, 3-(1-oxopyrrolidin-1-yl)propyl, (4-(2-hydroxy-2-methylpropyl)piperazin-1-ylethyl, 3-(4-methylpiperazin-1-yl)propyl, tetrahyrofuran-2-ylmethyl, 1-ethylpiperidin-4-ylmethyl, 2-(1,1,-dioxothiomorpholin-4-yl)ethyl, 4-(oxetan-3-yl)piperazin-1-ylethyl, piperidin-1-ylethyl, 1-methylpiperidin-4-ylmethyl, 4-ethylpiperazin-1-ylethyl, pyrrolidin-1-ylethyl, 2,6-dimethylpiperazin-1-ylethyl, 3,5-dimethylpiperazin-1-ylethyl, 1-methyl-4-hydroxypiperidin-4-ylmethyl, and 3-(4-ethylpiperazin-1-yl)propyl;
heterocyclyl (wherein heterocyclyl is optionally substituted with one, two, or three substituents independently selected from alkyl, halo, hydroxy, hydroxyalkyl, alkoxyalkyl, aminoalkyl, optionally substituted aryl, optionally substituted heteroaryl, and optionally substituted heterocyclyl), heteroaralkyl, phenyl, or heteroaryl (where phenyl and heteroaryl are optionally substituted with one, two, or three substituents where two of the optional substituents are independently selected from alkyl, hydroxy, alkoxy, halo, haloalkyl, haloalkoxy, and cyano and the third optional substituent is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl), wherein said heterocyclyl, heteroarylkyl, or heteroaryl is selected from pyridin-2-yl, imidazol-1-ylethyl, oxetan-3-yl, 1-methylpiperidin-4-yl, 1-methylpiperazin-4-yl, tetrahydrofuran-3-yl, and tetrahydropyran-4-yl; or aminoalkyl, selected from 3-dimethylaminopropyl, 4-diethylaminobutyl, 3-diethylaminopropyl, 2-diethylaminoethyl, and 2-dimethylaminoethyl.

16. The compound of claim 1 or a pharmaceutically acceptable salt thereof, wherein Y is —CO—.

17. The compound of claim 1 or a pharmaceutically acceptable salt thereof, wherein $R^c$ is:

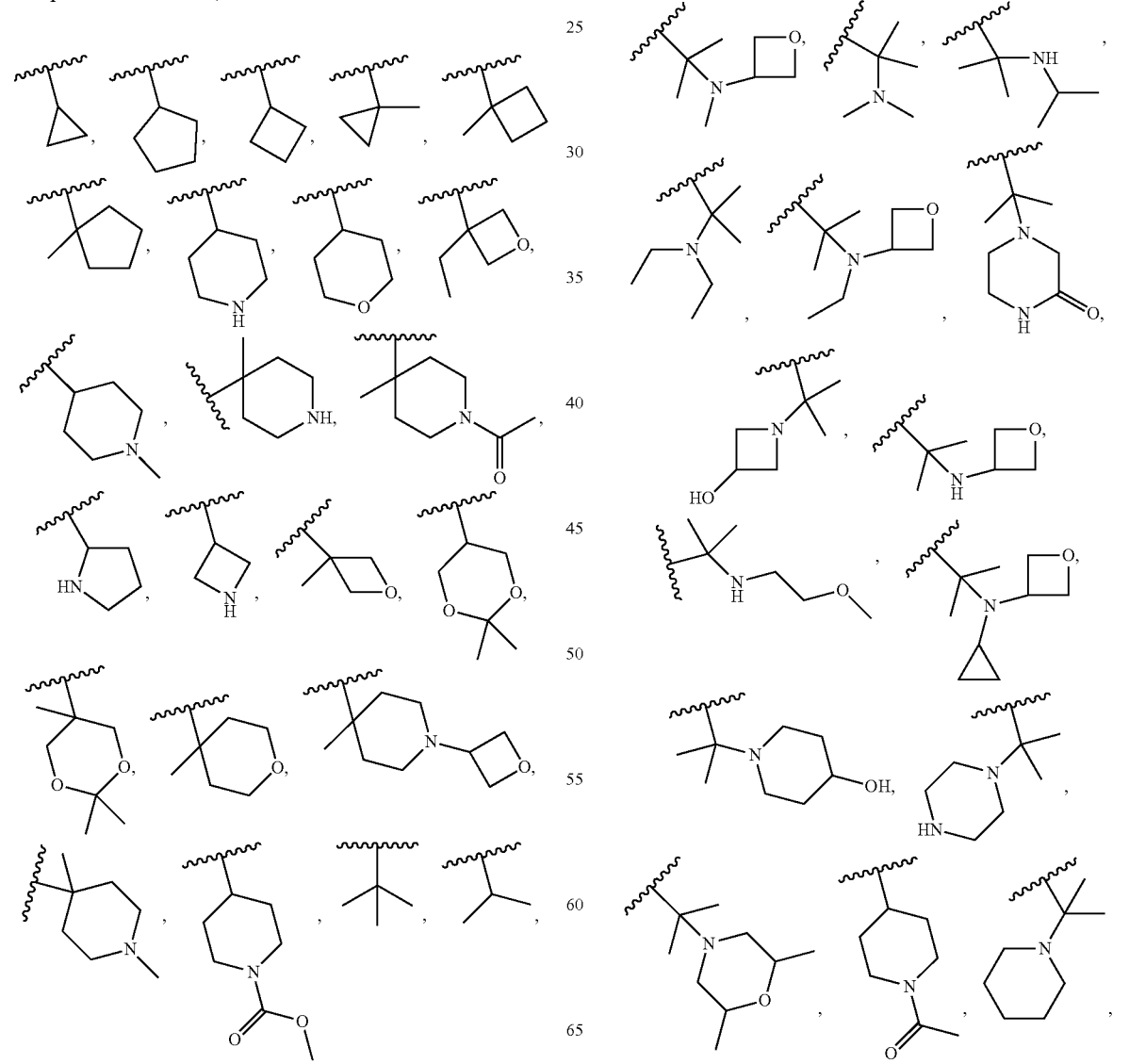

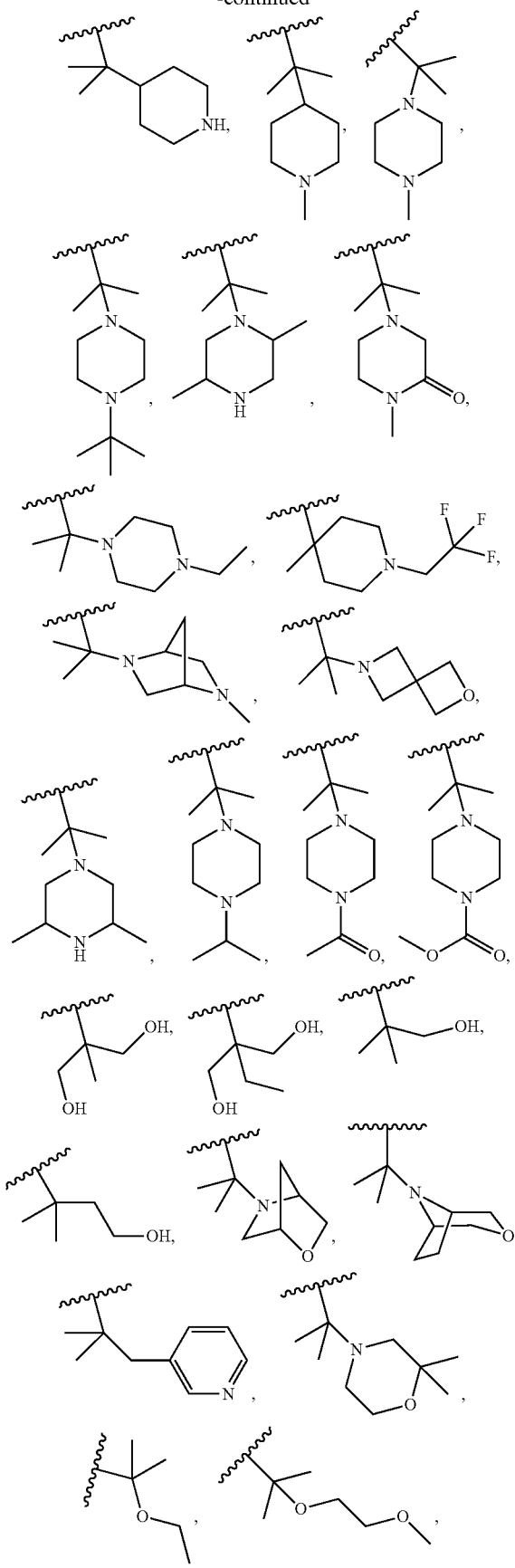
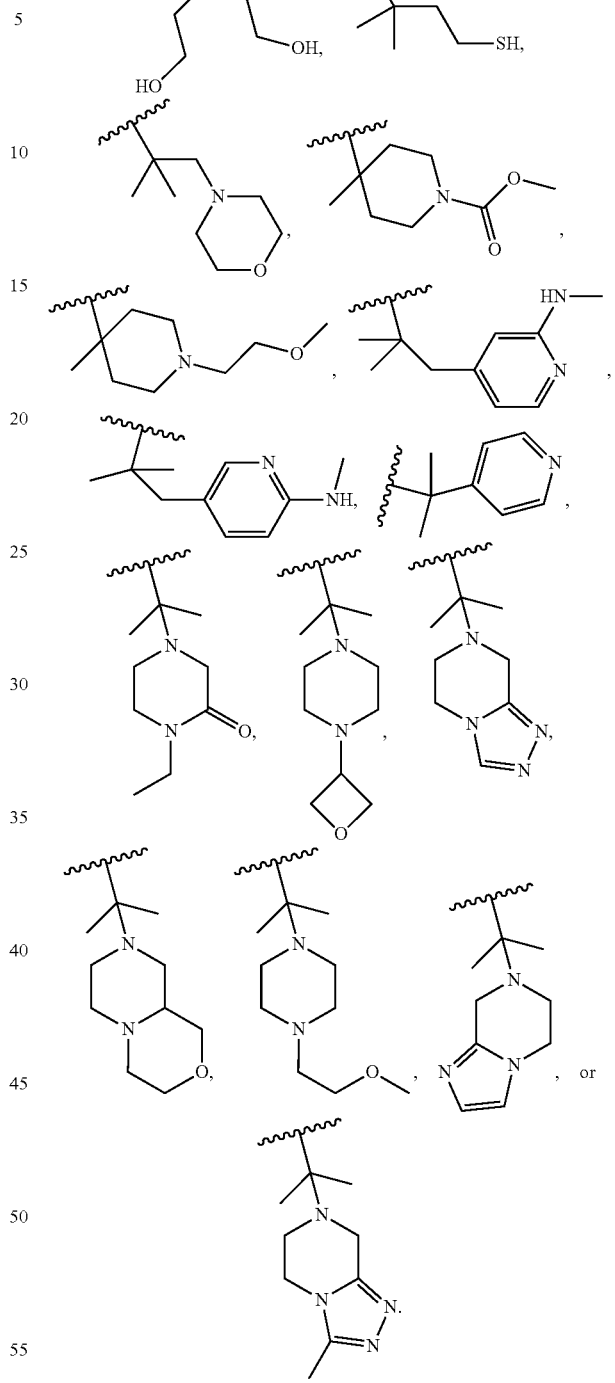

18. The compound of claim 1 or a pharmaceutically acceptable salt thereof, wherein $R^c$ is:

alkyl, selected from isopropyl and tert-butyl;

alkyl substituted with —NRR', wherein said alkyl substituted with —NRR' is selected from 2-methyl-3-amino-prop-2-yl, 2-methyl-3-dimethylamino-prop-2-yl, and —C(CH$_3$)$_2$—NRR' where R is hydrogen, methyl, ethyl, or cyclopropyl and R' is hydrogen, methyl, ethyl, isopropyl, oxetan-3-yl, 2-ethoxyethyl, or cyclopropyl;

alkyoxyalkyloxy or alkyl substituted with one to two hydroxy or alkoxy, wherein said alkyloxyalkyloxy or substituted alkyl is selected from 4-hydroxy-2-methylbut-2-yl, 1,5-dihydroxypent-3-yl, 2-ethoxyprop-2-yl, 1-hydroxy-2-hydroxymethylbut-2-yl, 1-hydroxy-2-hydroxymethylprop-2-yl, 2-hydroxymethylprop-2-yl, and 2-methoxyethyloxyprop-2-yl;

cycloalkyl optionally substituted with alkyl, wherein said cycloalkyl is selected from cyclopropyl, cyclobutyl, cyclopentyl, 1-methylcyclopropylene, 1-methylcyclobutylene, and 1-methylcyclopentylene;

optionally substituted heterocyclyl selected from pyrrolidin-2-yl, 3-methyloxetan-3-yl,1-methoxycarbonylpiperidin-4-yl, 4-methylpiperidin-4-yl, 1-methycarbonyl-4-methylpiperidin-4-yl, 4-methyltetrahydropyran-4-yl, azetidin-3-yl, 1,4-dimethylpiperidin-4-yl, 1-methylpiperidin-4-yl, 4-methyl-1-(2,2,2-trifluoroethyl)piperidin-4-yl, 4-methyl-1-(2-methoxyethyl)piperidin-4-yl, 1-methylcarbonylpiperidin-4-yl, piperidin-4-yl, tetrahydropyran-4-yl, 1-methoxycarbonyl-4-methyl-piperidin-4-yl, 1-oxetan-3-yl-4-methylpiperidin-4-yl, and 3-ethyloxetan-3-yl;

optionally substituted heterocyclylalkyl, wherein said optionally substituted heterocyclylalkyl is —C(CH$_3$)$_2$—R$^a$ where R$^a$ is pyrrolidin-1-yl, 4-methoxycarbonylpiperazin-1-yl, azetidin-1-yl, 1-methylpiperidin-4-yl, 4-(2-methoxyethyl)piperazin-1-yl, piperidin-4-yl, piperidin-1-yl, morpholino-4-yl, morpholino-4-ylmethyl, 2,2-dimethylmorpholin-4-yl, 3-hydroxyazetidin-1-yl, 4-hydroxypiperidin-1-yl, 3-oxopiperazin-1-yl, 4-methyl-3-oxopiperazin-1-yl, 4-ethyl-3-oxopiperazin-1-yl, 4-methylpiperazin-1-yl, piperazin-1-yl, 3,5-dimethylpiperazin-1-yl, 2,6-dimethyl-morpholino-4-yl, 1,2,6-trimethylpiperazin-4-yl, 4-ethylpiperazin-1-yl, 4-isopropylpiperazin-1-yl, 4-tert-butylpiperazin-1-yl, 2,5-dimethylpiperazin-1-yl, 4-methylcarbonylpiperazin-1-yl, 1-oxetan-3-yl-piperazin-4-yl, or 3,3-difluoroazetidin-1-yl.

19. A compound selected from the group consisting of:
2-(3-(2-(6-(2-chlorophenyl)-2-((4-(diethylamino)butyl)amino)-7-oxopyrido[2,3-d]pyrimidin-8(7H)-yl)ethyl)piperidine-1-carbonyl)-4-methylpent-2-enenitrile;
2-(4-(2-(6-(2-chloro-3,5-dimethoxyphenyl)-2-(methylamino)-7-oxopyrido[2,3-d]pyrimidin-8(7H)-yl)ethyl)piperazine-1-carbonyl)-4,4-dimethylpent-2-enenitrile;
2-(4-(2-(6-(2,6-dichloro-3,5-dimethoxyphenyl)-2-(methylamino)-7-oxopyrido[2,3-d]pyrimidin-8(7H)-yl)ethyl)piperazine-1-carbonyl)-4,4-dimethylpent-2-enenitrile;
N-(1-(2-(6-(2-chloro-3,5-dimethoxyphenyl)-2-(methylamino)-7-oxopyrido[2,3-d]pyrimidin-8(7H)-yl)ethyl)piperidin-4-yl)-2-cyano-4,4-dimethylpent-2-enamide;
2-(4-(3-(6-(2-chloro-3,5-dimethoxyphenyl)-2-(methylamino)-7-oxopyrido[2,3-d]pyrimidin-8(7H)-yl)propyl)piperazine-1-carbonyl)-4,4-dimethylpent-2-enenitrile;
2-((3aR,6aS)-5-(2-(6-(2-chloro-3,5-dimethoxyphenyl)-2-(methylamino)-7-oxopyrido[2,3-d]pyrimidin-8(7H)-yl)ethyl)octahydropyrrolo[3,4-c]pyrrole-2-carbonyl)-4,4-dimethylpent-2-enenitrile;
2-(4-(3-(6-(2,6-dichloro-3,5-dimethoxyphenyl)-2-(methylamino)-7-oxopyrido[2,3-d]pyrimidin-8(7H)-yl)propyl)piperazine-1-carbonyl)-4,4-dimethylpent-2-enenitrile;
2-(3-(2-(6-(2,6-dichloro-3,5-dimethoxyphenyl)-2-(methylamino)-7-oxopyrido[2,3-d]pyrimidin-8(7H)-yl)ethoxy)azetidine-1-carbonyl)-4,4-dimethylpent-2-enenitrile;
2-(3-(2-(6-(2,6-dichloro-3,5-dimethoxyphenyl)-2-(methylamino)-7-oxopyrido[2,3-d]pyrimidin-8(7H)-yl)ethoxy)piperidine-1-carbonyl)-4,4-dimethylpent-2-enenitrile;
2-(3-(2-(6-(2,6-dichloro-3,5-dimethoxyphenyl)-2-(methylamino)-7-oxopyrido[2,3-d]pyrimidin-8(7H)-yl)ethoxy)pyrrolidine-1-carbonyl)-4,4-dimethylpent-2-enenitrile;
N-(4-(2-(6-(2-chlorophenyl)-2-((4-(diethylamino)butyl)amino)-7-oxopyrido[2,3-d]pyrimidin-8(7H)-yl)ethyl)phenyl)-2-cyano-4-methylpent-2-enamide;
2-(3-(2-(6-(2-chlorophenyl)-2-((4-(diethylamino)butyl)amino)-7-oxopyrido[2,3-d]pyrimidin-8(7H)-yl)ethyl)piperidine-1-carbonyl)-4-methylpent-2-enenitrile;
N-(3-(2-(6-(2-chlorophenyl)-2-((4-(diethylamino)butyl)amino)-7-oxopyrido[2,3-d]pyrimidin-8(7H)-yl)ethyl)phenyl)-2-cyano-4-methylpent-2-enamide;
2-cyano-N-(4-(2-(6-(2,6-dichloro-3,5-dimethoxyphenyl)-2-((4-(diethylamino)butyl)amino)-7-oxopyrido[2,3-d]pyrimidin-8(7H)-yl)ethyl)phenyl)-4-methylpent-2-enamide;
2-cyano-N-(3-((6-(2,6-dichloro-3,5-dimethoxyphenyl)-2-((4-(diethylamino)butyl)amino)-7-oxopyrido[2,3-d]pyrimidin-8(7H)-yl)methyl)phenyl)-4-methylpent-2-enamide;
2-cyano-N-(3-(2-(6-(2,6-dichloro-3,5-dimethoxyphenyl)-2-((4-(diethylamino)butyl)amino)-7-oxopyrido[2,3-d]pyrimidin-8(7H)-yl)ethyl)phenyl)-4-methylpent-2-enamide;
2-cyano-N-(3-(2-(6-(2,6-dichloro-3,5-dimethoxyphenyl)-2-(methylamino)-7-oxopyrido[2,3-d]pyrimidin-8(7H)-yl)ethyl)phenyl)-4-methylpent-2-enamide;
2-cyano-N-(4-(2-(6-(3,5-dimethoxyphenyl)-2-(methylamino)-7-oxopyrido[2,3-d]pyrimidin-8(7H)-yl)ethyl)phenyl)-4,4-dimethylpent-2-enamide;
4-amino-2-cyano-N-(4-(2-(6-(3,5-dimethoxyphenyl)-2-(methylamino)-7-oxopyrido[2,3-d]pyrimidin-8(7H)-yl)ethyl)phenyl)-4-methylpent-2-enamide;
2-cyano-N-(3-(2-(6-(3,5-dimethoxyphenyl)-2-(methylamino)-7-oxopyrido[2,3-d]pyrimidin-8(7H)-yl)ethyl)phenyl)-4,4-dimethylpent-2-enamide;
4-amino-2-cyano-N-(3-(2-(6-(3,5-dimethoxyphenyl)-2-(methylamino)-7-oxopyrido[2,3-d]pyrimidin-8(7H)-yl)ethyl)phenyl)-4-methylpent-2-enamide;
N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4,4-dimethylpent-2-enamide;
4-amino-N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methylpent-2-enamide;
N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4,4-dimethylpent-2-enamide;
4-amino-N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methylpent-2-enamide;
N-(6-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4,4-dimethylpent-2-enamide;
4-amino-N-(6-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4-methylpent-2-enamide;
4-amino-2-cyano-N-(4-(2-(6-(3,5-dimethoxyphenyl)-2-(methylamino)-7-oxopyrido[2,3-d]pyrimidin-8(7H)-yl)ethyl)pyridin-2-yl)-4-methylpent-2-enamide;

2-cyano-N-(6-(2-(6-(3,5-dimethoxyphenyl)-2-(methylamino)-7-oxopyrido[2,3-d]pyrimidin-8(7H)-yl)ethyl)pyridin-2-yl)-4,4-dimethylpent-2-enamide;

4-amino-N-(4-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4-methylpent-2-enamide;

4-amino-N-(5-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4-methylpent-2-enamide;

4-amino-2-cyano-N-(6-(2-(6-(3,5-dimethoxyphenyl)-2-(methylamino)-7-oxopyrido[2,3-d]pyrimidin-8(7H)-yl)ethyl)pyridin-2-yl)-4-methylpent-2-enamide;

N-(4-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4,4-dimethylpent-2-enamide;

2-cyano-N-(4-(2-(6-(3,5-dimethoxyphenyl)-2-(methylamino)-7-oxopyrido[2,3-d]pyrimidin-8(7H)-yl)ethyl)pyridin-2-yl)-4,4-dimethylpent-2-enamide;

4-amino-2-cyano-N-(5-(2-(6-(3,5-dimethoxyphenyl)-2-(methylamino)-7-oxopyrido[2,3-d]pyrimidin-8(7H)-yl)ethyl)pyridin-2-yl)-4-methylpent-2-enamide;

4-amino-N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-N,4-dimethylpent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-ethoxy-4-methylpent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-morpholinopent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(methyl(oxetan-3-yl)amino)pent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(4-ethylpiperazin-1-yl)-4-methylpent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(2-oxa-6-azaspiro[3.3]heptan-6-yl)pent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(4-methylpiperazin-1-yl)pent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(methylamino)pent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(dimethylamino)-4-methylpent-2-enamide;

4-amino-N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-N,4-dimethylpent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-N,4-dimethyl-4-(methylamino)pent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(dimethylamino)-N,4-dimethylpent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-N,4-dimethyl-4-(methylamino)pent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(dimethylamino)-N,4-dimethylpent-2-enamide;

2-cyano-N-(5-(2-(6-(3,5-dimethoxyphenyl)-2-(methylamino)-7-oxopyrido[2,3-d]pyrimidin-8(7H)-yl)ethyl)pyridin-2-yl)-4,4-dimethylpent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-ethoxy-4-methylpent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-morpholinopent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(methyl(oxetan-3-yl)amino)pent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(2-oxa-6-azaspiro[3.3]heptan-6-yl)pent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(4-methylpiperazin-1-yl)pent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(4-ethylpiperazin-1-yl)-4-methylpent-2-enamide;

N-(5-(2-(6-(2-chloro-3,5-dimethoxyphenyl)-2-(methylamino)-7-oxopyrido[2,3-d]pyrimidin-8(7H)-yl)ethyl)pyridin-2-yl)-2-cyano-4,4-dimethylpent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(methylamino)pent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(dimethylamino)-4-methylpent-2-enamide;

N-(3-(2-(2-amino-6-(2-chloro-3, 5-dimethoxyphenyl)-7-oxopyrido[2,3-d]pyrimidin-8(7H)-yl)ethyl)phenyl)-2-cyano-4,4-dimethylpent-2-enamide;

N-(3-(2-(6-(2-chloro-3,5-dimethoxyphenyl)-2-(ethylamino)-7-oxopyrido[2,3-d]pyrimidin-8(7H)-yl)ethyl)phenyl)-2-cyano-4,4-dimethylpent-2-enamide;

N-(3-(2-(6-(2-chloro-3,5-dimethoxyphenyl)-2-((2-hydroxy-2-methylpropyl)amino)-7-oxopyrido[2, 3-d]pyrimidin-8(7H)-yl)ethyl)phenyl)-2-cyano-4,4-dimethylpent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(4-hydroxypiperidin-1-yl)-4-methylpent-2-enamide;

N-(3-((6-(2-chloro-3,5-dimethoxyphenyl)-2-(methylamino)-7-oxopyrido[2,3-d]pyrimidin-8(7H)-yl)methyl)phenyl)-2-cyano-4,4-dimethylpent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4,4-dimethylpentanamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-(4-hydroxypiperidin-1-yl)-4-methylpent-2-enamide;

N-(3-(2-(6-(2-chloro-5-methoxyphenyl)-2-(methylamino)-7-oxopyrido[2,3-d]pyrimidin-8(7H)-yl)ethyl)phenyl)-2-cyano-4,4-dimethylpent-2-enamide;

2-cyano-N-(3-(2-(6-(2,4-dichlorophenyl)-2-(methylamino)-7-oxopyrido[2, 3-d]pyrimidin-8(7H)-yl)ethyl)phenyl)-4,4-dimethylpent-2-enamide;

2-cyano-N-(3-(2-(6-(2, 5-dimethylphenyl)-2-(methylamino)-7-oxopyrido[2,3-d]pyrimidin-8(7H)-yl)ethyl)phenyl)-4,4-dimethylpent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-((3 S,5R)-3,4,5-trimethylpiperazin-1-yl)pent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(4-(oxetan-3-yl)piperazin-1-yl)pent-2-enamide;

N-(3-(2-(6-(2-chloro-3,5-dimethoxyphenyl)-2-(methylamino)-7-oxopyrido[2,3-d]pyrimidin-8(7H)-yl)ethyl)phenyl)-2-cyano-4-methyl-4-(4-(oxetan-3-yl)piperazin-1-yl)pent-2-enamide;

N-(3-(2-(6-(5-chloro-2-methoxyphenyl)-2-(methylamino)-7-oxopyrido[2,3-d]pyrimidin-8(7H)-yl)ethyl)phenyl)-2-cyano-4,4-dimethylpent-2-enamide;

2-cyano-4,4-dimethyl-N-(3-(2-(2-(methylamino)-7-oxo-6-(o-tolyl)pyrido [2,3-d]pyrimidin-8(7H)-yl)ethyl)phenyl)pent-2-enamide;

2-cyano-N-(3-(2-(6-(2-fluoro-3-methoxyphenyl)-2-(methylamino)-7-oxopyrido[2,3-d]pyrimidin-8(7H)-yl)ethyl)phenyl)-4,4-dimethylpent-2-enamide;

2-cyano-N-(3-(2-(6-(2-fluoro-5-methoxyphenyl)-2-(methylamino)-7-oxopyrido[2,3-d]pyrimidin-8(7H)-yl)ethyl)phenyl)-4,4-dimethylpent-2-enamide;

N-(4-(2-(6-(2-chloro-3,5-dimethoxyphenyl)-2-(methylamino)-7-oxopyrido[2,3-d]pyrimidin-8(7H)-yl)ethyl)thiazol-2-yl)-2-cyano-4,4-dimethylpent-2-enamide;

N-(4-(2-(6-(2-chloro-3,5-dimethoxyphenyl)-2-((2-morpholinoethyl)amino)-7-oxopyrido[2, 3-d]pyrimidin-8(7H)-yl)ethyl)phenyl)-2-cyano-4,4-dimethylpent-2-enamide;

N-(6-(2-(6-(2-chloro-3,5-dimethoxyphenyl)-2-((2-morpholinoethyl)amino)-7-oxopyrido[2,3-d]pyrimidin-8(7H)-yl)ethyl)pyridin-3-yl)-2-cyano-4,4-dimethylpent-2-enamide;

N-(4-(2-(6-(2-chloro-3,5-dimethoxyphenyl)-2-(methylamino)-7-oxopyrido[2,3-d]pyrimidin-8(7H)-yl)ethyl)phenyl)-2-cyano-3-methylbut-2-enamide;

N-(5-(2-(6-(2-chloro-3,5-dimethoxyphenyl)-2-(methylamino)-7-oxopyrido[2,3-d]pyrimidin-8(7H)-yl)ethyl)pyrazin-2-yl)-2-cyano-4,4-dimethylpent-2-enamide;

N-(tert-butyl)-3-(4-(2-(6-(2-chloro-3,5-dimethoxyphenyl)-2-(methylamino)-7-oxopyrido[2,3-d]pyrimidin-8(7H)-yl)ethyl)phenyl)-2-cyanoacrylamide;

N-(tert-butyl)-3-(3-(2-(6-(2-chloro-3,5-dimethoxyphenyl)-2-(methylamino)-7-oxopyrido[2,3-d]pyrimidin-8(7H)-yl)ethyl)phenyl)-2-cyanoacrylamide;

2-cyano-N-(4-(2-(6-(2-fluoro-3,5-dimethoxyphenyl)-2-((2-morpholinoethyl)amino)-7-oxopyrido[2,3-d]pyrimidin-8(7H)-yl)ethyl)phenyl)-4,4-dimethylpent-2-enamide;

N-(tert-butyl)-3-(4-(3-(6-(2-chloro-3,5-dimethoxyphenyl)-2-(methylamino)-7-oxopyrido[2,3-d]pyrimidin-8(7H)-yl)propyl)phenyl)-2-cyanoacrylamide;

N-(tert-butyl)-3-(3-(3-(6-(2-chloro-3,5-dimethoxyphenyl)-2-(methylamino)-7-oxopyrido[2,3-d]pyrimidin-8(7H)-yl)propyl)phenyl)-2-cyanoacrylamide;

N-(2-chloro-4-(2-(6-(2-chloro-3,5-dimethoxyphenyl)-2-((2-morpholinoethyl)amino)-7-oxopyrido[2,3-d]pyrimidin-8(7H)-yl)ethyl)phenyl)-2-cyano-4,4-dimethylpent-2-enamide;

N-(4-(2-(6-(2-chloro-3,5-dimethoxyphenyl)-2-((2-morpholinoethyl)amino)-7-oxopyrido[2,3-d]pyrimidin-8(7H)-yl)ethyl)-3-fluorophenyl)-2-cyano-4,4-dimethylpent-2-enamide; and N-(4-(2-(6-(2-chloro-3,5-dimethoxyphenyl)-2-((2-morpholinoethyl)amino)-7-oxopyrido[2,3-d]pyrimidin-8(7H)-yl)ethyl)-2-fluorophenyl)-2-cyano-4,4-dimethylpent-2-enamide;

an individual (E) or (Z) isomer thereof;

or a pharmaceutically acceptable salt of any of the above compounds including the individual (E) or (Z) isomer.

20. A pharmaceutical composition comprising a compound of claim 1 and/or a pharmaceutically acceptable salt thereof; and a pharmaceutically acceptable excipient.

21. A pharmaceutical composition comprising a compound of claim 19 and/or a pharmaceutically acceptable salt thereof; and a pharmaceutically acceptable excipient.

22. A method of inhibiting FGFR in a patient which method comprises administering to the patient in recognized need thereof, a pharmaceutical composition comprising a compound of claim 1 and/or a pharmaceutically acceptable salt thereof, and a pharmaceutically acceptable excipient.

23. A method of inhibiting FGFR in a patient which method comprises administering to the patient a pharmaceutical composition comprising a compound of claim 19 and/or a pharmaceutically acceptable salt thereof, and a pharmaceutically acceptable excipient.

* * * * *